United States Patent
Li et al.

(10) Patent No.: US 10,106,783 B2
(45) Date of Patent: Oct. 23, 2018

(54) HCV CULTURE SYSTEMS AND DIRECT-ACTING ANTIVIRAL SENSITIVITY

(71) Applicant: Hvidovre Hospital, Hvidovre (DK)

(72) Inventors: Yiping Li, Hvidovre (DK); Santseharay Ramirez Almeida, Hvidovre (DK); Daryl Grant Humes, Copenhagen Ø (DK); Judith M. Gottwein, Frederiksberg C (DK); Jens Bukh, Præstø (DK)

(73) Assignee: HVIDOVRE HOSPITAL, Hvidovre (DK)

( * ) Notice: Subject to any disclaimer, the term of this patent is extended or adjusted under 35 U.S.C. 154(b) by 0 days.

(21) Appl. No.: 15/025,833

(22) PCT Filed: Oct. 21, 2014

(86) PCT No.: PCT/DK2014/050343
§ 371 (c)(1),
(2) Date: Mar. 29, 2016

(87) PCT Pub. No.: WO2015/058772
PCT Pub. Date: Apr. 30, 2015

(65) Prior Publication Data
US 2016/0244729 A1    Aug. 25, 2016

(30) Foreign Application Priority Data
Oct. 22, 2013   (DK) .................. 2013 70607

(51) Int. Cl.
*C12N 7/00* (2006.01)
*C12Q 1/02* (2006.01)

(52) U.S. Cl.
CPC .............. *C12N 7/00* (2013.01); *C12Q 1/025* (2013.01); *C12N 2770/24221* (2013.01); *C12N 2770/24234* (2013.01); *C12N 2770/24251* (2013.01); *C12N 2770/24252* (2013.01)

(58) Field of Classification Search
None
See application file for complete search history.

(56) References Cited

U.S. PATENT DOCUMENTS

| | | |
|---|---|---|
| 8,454,974 B2 | 6/2013 | Scheel et al. |
| 8,506,969 B2 | 8/2013 | Gottwein et al. |
| 8,563,706 B2 | 10/2013 | Scheel et al. |
| 8,569,472 B2 | 10/2013 | Gottwein et al. |
| 8,618,275 B2 | 12/2013 | Jensen et al. |
| 8,663,653 B2 | 3/2014 | Gottwein et al. |
| 8,772,022 B2 | 7/2014 | Gottwein et al. |
| 8,846,891 B2 | 9/2014 | Prento et al. |
| 9,382,517 B2 | 7/2016 | Li et al. |
| 9,388,389 B2 | 7/2016 | Scheel et al. |
| 2009/0252755 A1 | 10/2009 | Bukh et al. |
| 2010/0093841 A1 | 4/2010 | Gottwein et al. |
| 2016/0244729 A1 | 8/2016 | Li et al. |

FOREIGN PATENT DOCUMENTS

| | | |
|---|---|---|
| WO | WO 2006/096459 A2 | 9/2006 |
| WO | WO 2008/125119 A1 | 10/2008 |
| WO | WO 2010/017818 A1 | 2/2010 |
| WO | WO 2010/022727 A1 | 3/2010 |
| WO | WO 2011/038737 A1 | 4/2011 |
| WO | WO 2013/139339 A1 | 9/2013 |
| WO | WO 2013/139340 A1 | 9/2013 |
| WO | WO 2015/014369 A1 | 2/2015 |
| WO | WO 2015/058772 A2 | 4/2015 |
| WO | WO 2015/158353 A1 | 10/2015 |
| WO | WO 2015/179204 A1 | 11/2015 |

OTHER PUBLICATIONS

GenBank: GU814266.1, Synthetic construct Hepatitis C virus ED43 polyprotein gene, complete cds. 2010.*
Kolykhalov, Alexander A. et al., "Transmission of Hepatitis C by Intrahepatic Inoculation with Transcribed RNA" Science, Jul. 25, 1997, pp. 570-574, vol. 277.
Li, Yi-Ping et al., "Differential Sensitivity of 5'UTR-NS5A Recombinants of Hepatitis C Virus Genotypes 1-6 to Protease and NS5A Inhibitors" Gastroenterology, 2014, pp. 812-821, vol. 146.
Li, Yi-Ping et al., "Highly efficient full-length hepatitis C virus genotype 1 (strain TN) infectious culture system" PNAS, Nov. 27, 2012, pp. 19757-19762, vol. 109, No. 48.
Li, Yi-Ping et al., "Robust full-length hepatitis C virus genotype 2a and 2b infectious cultures using mutations identified by a systematic approach applicable to patient strains" PNAS, Mar. 30, 2012, pp. E1101-E1110, www.pnas.org/cgi/doi/10.1073/pnas.1203829109.
International Search Report for PCT/DK2014/050343 dated Apr. 15, 2015.
Akazawa, Daisuke et al., "Production and characterization of HCV particles from serum-free culture" Vaccine, 2011, pp. 4821-4828, vol. 29.
Akazawa, Daisuke et al., "Neutralizing Antibodies Induced by Cell Culture-Derived Hepatitis C Virus Protect Against Infection in Mice" Gastroenterology, 2013, pp. 447-455, vol. 145.
Altschul, Stephen F. et al., "Basic Local Alignment Search Tool" J. Mol. Biol., 1990, pp. 403-410, vol. 215.
Altschul, Stephen F. et al., "Protein database searches for multiple alignments" Proc. Natl. Acad. Sci, Jul. 1990, pp. 5509-5513, vol. 87.
Bukh, Jens et al., "A milestone for hepatitis C virus research: A virus generated in cell culture is fully viable in vivo" PNAS, Mar. 2006, pp. 3500-3501, vol. 103, No. 10.
Bukh, Jens et al., "Challenge Pools of Hepatitis C Virus Genotypes 1-6 Prototype Strains: Replication Fitness and Pathogenicity in Chimpanzees and Human Liver-Chimeric Mouse Models" J Infect Dis., May 2010, pp. 1381-1389, vol. 201, No. 9.

(Continued)

*Primary Examiner* — Michelle S Horning
(74) *Attorney, Agent, or Firm* — Knobbe, Martens, Olson & Bear LLP

(57) ABSTRACT

The present invention relates to hepatitis C virus (HCV) culture systems of genotypes 1a, 3a, 4a, 5a, and 6a that directly contribute to HCV drug and vaccine development, to HCV basic research and better-individualized treatment of HCV infected patients.

9 Claims, 12 Drawing Sheets
Specification includes a Sequence Listing.

(56) References Cited

OTHER PUBLICATIONS

Chen, N. et al., "Oxymatrine inhibits target cell infection in the HCVcc system" Chinese Journal of Hepatology, Jan. 2016, pp. 40-45, vol. 24, No. 1—Abstract.
Date, Tomoko et al., "Novel Cell Culture-Adapted Genotype 2a Hepatitis C Virus Infectious Clone" Journal of Virology, Oct. 2012, pp. 10805-10820, vol. 86, No. 19.
Engle, Ronald E. et al., "Development of a TaqMan Assay for the Six Major Genotypes of Hepatitis C Virus: Comparison With Commercial Assays" Journal of Medical Virology, 2008, pp. 72-79, vol. 80.
Gottwein, Judith M., et al., "Development and Characterization of Hepatitis C Virus Genotype 1-7 Cell Culture Systems: Role of CD81 and Scavenger Receptor Class B Type I and Effect of Antiviral Drugs" Hepatology, 2009, pp. 364-377, vol. 49, No. 2.
Gottwein, Judith M. et al., "Combination Treatment with Hepatitis C Virus Protease and NS5A Inhibitors Is Effective against Recombinant Genotype 1a, 2a, and 3a Viruses" Antimicrobial Agents and Chemotherapy, Mar. 2013, pp. 1291-1303, vol. 57, No. 3.
Houghton, Michael et al., "An Inactivated Hepatitis C Virus Vaccine on the Horizon?" Editorials, 2013, pp. 285-288.
Kuiken, Carla et al., "A Comprehensive System for Consistent Numbering of HCV Sequences, Proteins and Epitopes" Hepatology, Nov. 2006, pp. 1355-1361, vol. 44, No. 5.
Li, Yi-Ping et al., "Protease inhibitors differentially inhibit novel HCV 5'UTR-NS5A genotype 3-6 recombinants" Article intended for submission to Gastroenterology.
Li, Yi-Ping et al., "MicroRNA-122 antagonism against hepatitis C virus genotypes 1-6 and reduced efficacy by host RNA insertion or mutations in the HCV 5' UTR" PNAS, Mar. 2011, pp. 4991-4996, vol. 108, No. 12.
Li, Yi-Ping et al., "Non-genotype-specific role of the hepatitis C virus 5' untranslated region in virus production and in inhibition by interferon" Virology, 2011, pp. 222-234, vol. 421.
Li, Yi-Ping et al., "Efficient infectious cell culture systems of the hepatitis C virus prototype strains HCV-1 and H77" JVI-02877-14R1, Oct. 2014.
Lindenbach, Brett D. et al., "Complete Replication of Hepatitis C Virus in Cell Culture" Science, Jul. 2005, pp. 623-626; vol. 309.
Mathiesen, Christian K. et al., "Production and characterization of high-titer serum-free cell culture grown hepatitis C virus particles of genotype 1-6" Virology, 2014, pp. 190-208, vol. 458-459.
Morris, David L. et al., "Adipose Tissue Macrophages Function as Antigen-Presenting Cells and Regulate Adipose Tissue CD4+ T Cells in Mice" Diabetes, Aug. 2013, pp. 2762-2772, vol. 62.
Murayama, Asako et al., "The NS3 Helicase and NS5B-to-3 X Regions Are Important for Efficient Hepatitis C Virus Strain JFH-1 Replication in Huh7 Cells" Journal of Virology, Aug. 2007, pp. 8030-8040, vol. 81, No. 15.
Murayama, Asako et al., "RNA Polymerase Activity and Specific RNA Structure Are Required for Efficient HCV Replication in Cultured Cells" PLoS Pathogens, Apr. 2010, pp. 1-11, vol. 6, Issue 4, e1000885.
Okamoto, Hiroaki et al., "Nucleotide sequence of the genomic RNA of hepatitis C virus isolated from a human carrier: comparison with reported isolates for conserved and divergent regions" Journal of General Virology, 1991, pp. 2697-2704, vol. 71.
Okamoto, Hiroaki et al., "Full-Length Sequence of a Hepatitis C Virus Genome Having Poor Homology to Reported Isolates: Comparative Study of Four Distinct Genotypes" Virology, 1992, pp. 331-341, vol. 188.
Ramirez, Santseharay et al., "Highly Efficient Infectious Cell Culture of Three HCV Genotype 2b Strains and Sensitivity to Lead Protease, NS5A, and Polymerase Inhibitors" submitted to Hepatology on Jun. 12, 2013.
Ramirez, Santseharay et al., "Highly Efficient Infectious Cell Culture of Three Hepatitis C Virus Genotype 2b Strains and Sensitivity to Lead Protease, Nonstructural Protein 5A, and Polymerase Inhibitors" Hepatology, Feb. 2014, pp. 395-407, vol. 59, No. 2.
Scheel, Troels K.H. et al., "Recombinant HCV Variants With NS5A From Genotypes 1-7 Have Different Sensitivities to an NS5A Inhibitor but Not Interferon-α" Gastroenterology, 2011, pp. 1032-1042, vol. 140.
Shiokawa, Mai et al., "Novel Permissive Cell Lines for Complete Propagation of Hepatitis C Virus" Journal of Virology, May 2014, pp. 5578-5594, vol. 88, No. 10.
Wakita, Takaji et al., "Production of infectious hepatitis C virus in tissue culture from a cloned viral genome" Nat Med., Jul. 2005, pp. 791-796, vol. 11, No. 7.
Yanagi, Masayuki et al., "Hepatitis C Virus: An Infectious Molecular Clone of a Second Major Genotype (2a) and Lack of Viability of Intertypic 1a and 2a Chimeras" Virology, 1999, pp. 250-263, vol. 262.
Yao, Xiangjie et al., "Baculovirus Mediated Production of Infectious Hepatitis C Virus in Human Hepatoma Cells Stably Expressing T7 RNA Polymerase" Mol Biotechnol, 2008, pp. 186-194, vol. 40.
Database UniParc, Nov. 28, 2012, XP-002699169.
Murayama, Asako et al., "Production of Infectious Chimeric Hepatitis C Virus Genotype 2b Harboring Minimal Regions of JFH-1" Journal of Virology, Feb. 2012, pp. 2143-2152, vol. 86, No. 4.
Scheel, Troels K.H. et al., "Development of JFH1-based cell culture systems for hepatitis C virus genotype 4a and evidence for cross-genotype neutralization" PNAS, Jan. 2008, pp. 997-1002, vol. 105, No. 3.
GenBank: AF009606.1, "Hepatitis C virus subtype 1a polyprotein gene, complete cds.", Jun. 18, 2009.
GenBank: BAD73984.1, "polyprotein, Partial [Hepatitis C virus subtype 1 B]", Oct. 17, 2008.

* cited by examiner

| Genotype(isolate) UTR-NS5A recombinant | Mutations engineered[a] | Transfection | | Second-passage | |
|---|---|---|---|---|---|
| | | Day with ≥80% cells infected | Peak log₁₀(FFU/ml) (day)[b] | Peak log₁₀(FFU/ml) (day)[b] | Peak log₁₀(IU/ml)[c] |
| 1a(TN) | LSG/A1226G/Q1773H[**] | 4 | 3.9 (8) | 4.8 (7) | 8.1 |
| 1a(H77) | LSG/A1226G/Q1773H[*] | 8 | 2.4 (13) | 4.3 (11) | 8.6 |
| 1a(S52) | LSG | 41[f] | 2.5 (44) | 4.5 (5,7,10)[z] | 7.7 |
| | LSG/D871G/H1819R | 13 | 3.3 (13) | 3.7 (8) | 8.9 |
| | LSG/H1819R | 22 | 3.5 (25) | n.d. | n.d. |
| | LSG/D871G/V1612E/H1819R/V2417A, exp. 1 | 11 | 3.6 (15) | 4.1 (14) | 8.5 |
| | LSG/D871G/V1612E/H1819R/V2417A, exp. 2 | 7 | 4.0 (11) | 4.3 (12) | 7.2 |
| 3a(ED43) | LSG | 50[f] | 2.4 (32) | 3.9 (11,13)[z,#] | 7.9[#] |
| | LSR/R781W/A1309P/A1786V, exp. 1 | 7 | 3.8 (7) | 3.2 (15) | 8.1 |
| | LSR/R781W/A1309P/A1786V, exp. 2 | 7 | 3.2 (7) | 3.1 (15) | 8.2 |
| 3a(SA13) | LSG, exp. 1 | 8 | 3.2 (13) | 4.8 (5) | n.d. |
| | LSG, exp. 2 | 7 | 2.8 (11) | 5.1 (7,9,12)[z] | 8.1 |
| | LSG/S2946/C1551F, exp. 1 | 3 | 4.5 (6) | 4.9 (9) | 7.9 |
| | LSG/S2946/C1551F, exp. 2 | 3 | 4.5 (6) | 4.9 (9) | 8.1 |
| 6a(HK6a) | LSG | 64 | 2.5 (70) | 3.8 (14,18)[z] | 7.4 |
| | LSG/T387F/S872P/V1550L/L1790M/S2218P, exp. 1 | 9 | 3.3 (9) | 3.8 (22) | 8.4 |
| | LSG/T387F/S872P/V1550L/L1790M/S2218P, exp. 2 | 7 | 3.4 (7) | 3.6 (26) | 8.3 |

Fig. 3

| | NS3/NS4A protease inhibitors<sup>a</sup> | | | | | | | | | | | | NS5A inhibitor<sup>a</sup> | |
|---|---|---|---|---|---|---|---|---|---|---|---|---|---|---|
| | Licensed for clinical use | | | | Phase III trials | | | | | | Phase II trials | | Phase III trials | |
| | Telaprevir (VX-950) | | Boceprevir (SCH503034) | | Asunaprevir (BMS-650032) | | Simeprevir (TMC435350) | | Vaniprevir (MK-7009) | | Faldaprevir (BI201335) | | MK-5172 | | Daclatasvir (BMS-790052) | |
| 5'UTR-NS5A recombinant | EC₅₀ (nM) | Fold to J6/JFH1 | EC₅₀ (nM) | Fold to J6/JFH1 | EC₅₀ (nM) | Fold to J6/JFH1 | EC₅₀ (nM) | Fold to J6/JFH1 | EC₅₀ (nM) | Fold to J6/JFH1 | EC₅₀ (nM) | Fold to J6/JFH1 | EC₅₀ (nM) | Fold to J6/JFH1 | EC₅₀ (nM) | Fold to J6/JFH1 |
| 1a(TN) | 265 | 0.5 | 203 | 0.3 | 64 | 0.4 | 45 | 0.5 | 21 | 0.2 | 22 | 0.3 | 3 | 1.9 | 0.06 | 0.7 |
| 1a(H77) | 456 | 0.9 | 425 | 0.7 | 31 | 0.2 | 10 | 0.1 | 15 | 0.2 | 7 | 0.1 | 3 | 1.9 | 0.05 | 0.5 |
| 2a(J6/JFH1)<sup>b</sup> | 493 | - | 589 | - | 159 | - | 91 | - | 88 | - | 87 | - | 1.6 | - | 0.09 | - |
| 3a(S52) | 2000 | 4.1 | 1215 | 2.1 | 2143 | 13.5 | 2476 | 27.2 | 1900 | 21.6 | 1512 | 17.4 | 20 | 12.5 | 0.54 | 6.0 |
| 4a(ED43) | 1949 | 4.0 | 1387 | 2.4 | 37 | 0.2 | 5 | 0.1 | 10 | 0.1 | 2 | 0.0 | 1 | 0.6 | 0.02 | 0.2 |
| 5a(SA13) | 539 | 1.1 | 403 | 0.7 | 82 | 0.5 | 109 | 1.2 | 26 | 0.3 | 11 | 0.1 | 3 | 1.9 | 0.03 | 0.3 |
| 6a(HK6a) | 124 | 0.3 | 141 | 0.2 | 55 | 0.3 | 56 | 0.6 | 17 | 0.2 | 21 | 0.2 | 2 | 1.3 | 0.07 | 0.8 |

Fig. 4

| HCV | Passage (day) | E2 | p7 | NS2 | NS3 | NS3 | NS3 | NS4A | NS4B | NS5A | NS5B |
|---|---|---|---|---|---|---|---|---|---|---|---|
| Nucleotide position | | | | | | | | | | | |
| Recombinant specific | | 2494 | 2584 | 3006 | 4018 | 4443 | 4731 | 5355 | 5660 | 6279 | 9277 |
| H77 reference (AF009606) | | 2494 | 2584 | 3006 | 4018 | 4443 | 4731 | 5355 | 5660 | 6279 | 9277 |
| Recombinant nucleotide | | A | T | A | C | T | T | G | A | A | A |
| 1a(IN)_LSG/A1226G/Q1773H | 1st (3, 5, 7)ᵃ | . | t/C | A/G | G | . | C | . | C | . | G |
| 1a(H77)_LSG/A1226G/Q1773H | 1st (10) | . | . | . | G | T/C | C | T | C | . | G |
| | 1st (16, 18)ᵃ | A/G | . | . | G | T/C | C | T | C | a/G | G |
| Amino acid position | | | | | | | | | | | |
| Recombinant specific | | 718 | 748 | 889 | 1226 | 1368 | 1464 | 1672 | 1773 | 1980 | 2979 |
| H77 reference (AF009606) | | 718 | 748 | 889 | 1226 | 1368 | 1464 | 1672 | 1773 | 1980 | 2979 |
| Amino acid change | | T-C | L-S | T-A | A-G | S-P | F-L | A-S | Q-H | I-V | D-G |

| HCV | Passage (day) | p7 | NS2 | NS2 | NS3 | NS3 | NS4A | NS4B | NS4B | NS5A | NS5A | NS5B | NS5B |
|---|---|---|---|---|---|---|---|---|---|---|---|---|---|
| Nucleotide position | | | | | | | | | | | | | |
| Recombinant specific | | 2681 | 2819 | 2946 | 4265 | 4730 | 5354 | 5697 | 5729 | 6431 | 7134 | 9267 | |
| H77 reference (AF009606) | | 2682 | 2820 | 2947 | 4266 | 4731 | 5355 | 5698 | 5730 | 6432 | 7144 | 9277 | |
| Recombinant nucleotide | | C | A | C | G | T | G | C | G | T | T | A | |
| 4a(ED43) | | | | | | | | | | | | | |
| +LSG | 1st (13) | C/T | A/g | C/T | C | C | | T | G/a | T/c | T/C | A/g | |
| | 2nd (11, 13)ᵉ | C/T | A/g | C/T | C | C | | T | G/A | T/C | T/C | . | |
| | 2nd (14, 16, 18)ᶠ | C/T | a/G | C/T | C | C | | T | G/A | . | T/C | . | |
| +LS/R781W/A1309P/A1786V, exp. 1 | 2nd (13) | T | . | . | C | C | | T | . | . | . | . | |
| Amino acid position | | | | | | | | | | | | | |
| Recombinant specific | | 781 | 827 | 869 | 1309 | 1464 | 1672 | 1786 | 1797 | 2031 | 2265 | 2976 | |
| H77 reference (AF009606) | | 781 | 827 | 869 | 1309 | 1464 | 1672 | 1786 | 1797 | 2031 | 2268 | 2979 | |
| Amino acid change | | R-W | T-A | P-L | A-P | P-L | A-S | A-V | V-I | C-R | V-A | D-G | |

Fig. 7

| HCV | Passage (day) | E1 | | NS2 | | NS3 | | | NS4A | | NS5B | |
|---|---|---|---|---|---|---|---|---|---|---|---|---|
| Nucleotide position | | | | | | | | | | | | |
| Recombinant specific | | 1219 | | 2828 | | 4732 | | 4994 | 5356 | | 9284 | |
| H77 reference (AF009606) | | 1221 | | 2827 | | 4731 | | 4993 | 5355 | | 9277 | |
| Recombinant nucleotide | | A | | T | | T | | G | G | | A | |
| 5a(SA13) | | | | | | | | | | | | |
| +LSG, exp. 1 | 1st (15) | A/g | | T/c | | C | | . | T | | C | |
| | 2nd (5) | A/g | | T/C | | C | | . | T | | C | |
| +LSG, exp. 2 | 1st (10) | A/g | | . | | C | | G/t | T | | C | |
| | 2nd (7, 9, 12) | a/G | | . | | C | | T | T | | C | |
| +LSG/S294G/C1551F, exp. 1 | 2nd (5) | G | | . | | C | | T | T | | C | |
| Amino acid position | | | | | | | | | | | | |
| Recombinant specific | | 294 | | 830 | | 1465 | | 1552 | 1673 | | 2982 | |
| H77 reference (AF009606) | | 294 | | 829 | | 1464 | | 1551 | 1672 | | 2979 | |
| Amino acid change | | S-G | | F-S | | F-L | | C-F | A-S | | D-G | |

Fig. 8

| HCV | Passage (day) | E1 | E1 | E2 | NS2 | NS2 | NS3 | NS3 | NS3 | NS4A | NS4B | NS4B | NS5A | NS5B |
|---|---|---|---|---|---|---|---|---|---|---|---|---|---|---|
| Nucleotide position | | | | | | | | | | | | | | |
| Recombinant specific | | 1389 | 1502 | 2974 | 3139 | | 4750 | 5008 | 5374 | 5503 | 5728 | 7012 | 9305 | |
| H77 reference (AF009606) | | 1385 | 1501 | 2955 | 3120 | | 4731 | 4989 | 5355 | 5484 | 5709 | 6993 | 9277 | |
| Recombinant nucleotide | | A | C | T | A | | T | G | A | T | A | T | A | |
| 6a(HK6a) | | | | | | | | | | | | | | |
| +LSG | 1st (42) | . | . | c/T | C | . | C | T | T | . | A | C | G | |
| | 2nd (14,18)ᵃ | . | . | T | C | . | C | T | T | . | A | C | G | |
| +LSG/T387I/S872P/V1550L/L1790M/S2218P.exp.1 | 2nd (22) | G | T | T | C | a/G | C | T | T | T | A | C | G | |
| Amino acid position | | | | | | | | | | | | | | |
| Recombinant specific | | 349 | 387 | 878 | 933 | | 1470 | 1556 | 1678 | 1721 | 1796 | 2224 | 2988 | |
| H77 reference (AF009606) | | 348 | 387 | 872 | 927 | | 1464 | 1550 | 1672 | 1715 | 1790 | 2218 | 2979 | |
| Amino acid change | | I-M | T-I | S-P | R-G | | F-L | V-L | A-S | I-F | L-M | S-P | D-G | |

Fig. 9

| 5'UTR-NS5A recombinant | EC₅₀ (95% confidence interval) | | | | | | NS5A inhibitor |
|---|---|---|---|---|---|---|---|
| | NS3/NS4A Protease inhibitors | | | | | | |
| | Telaprevir (VX-950) | Boceprevir (SCH503034) | Asunaprevir (BMS-650032) | Simeprevir (TMC435350) | Vaniprevir (MK-7009) | Faldaprevir (BI201335) | MK-5172 | Daclatasvir (BMS-790052) |
| 1a(TN) | 265 (243-289) | 203 (177-233) | 64 (53-78) | 45 (42-49) | 21 (17-24) | 22 (17-29) | 2.8 (2.6-2.9) | 0.061 (0.049-0.076) |
| 1a(H77) | 456 (396-525) | 425 (349-517) | 31 (28-35) | 10 (9.9-10.9) | 15 (12-19) | 7 (6-9) | 2.8 (2.7-2.9) | 0.045 (0.037-0.054) |
| 2a(J6/JFH1)ᶜ | 493 (398-611) | 589 (494-703) | 159 (85-296) | 91 (76-109) | 88 (55-140) | 87 (33-234) | 1.6 (0.4-6) | 0.088 (0.063-0.123) |
| 3a(S52) | 2000 (1817-2200) | 1215 (1096-1346) | 2143 (1933-2376) | 2476 (1572-3901) | 1900 (1499-2409) | 1512 (1106-2066) | 20.0 (15-27) | 0.538 (0.374-0.779) |
| 4a(ED43) | 1949 (1737-2183) | 1387 (1186-1623) | 37 (34-42) | 5 (4-5) | 10 (9-11) | 2 (2-3) | 1.0 (0.9-1) | 0.017 (0.013-0.022) |
| 5a(SA13) | 539 (458-633) | 403 (294-552) | 82 (67-99) | 109 (96-123) | 26 (22-31) | 11 (8-14) | 3.4 (3-3.8) | 0.026 (0.020-0.034) |
| 6a(HK6a) | 124 (108-143) | 141 (131-152) | 55 (46-65) | 56 (51-62) | 17 (15-20) | 21 (16-26) | 1.7 (1.5-2) | 0.068 (0.053-0.086) |

Fig. 10

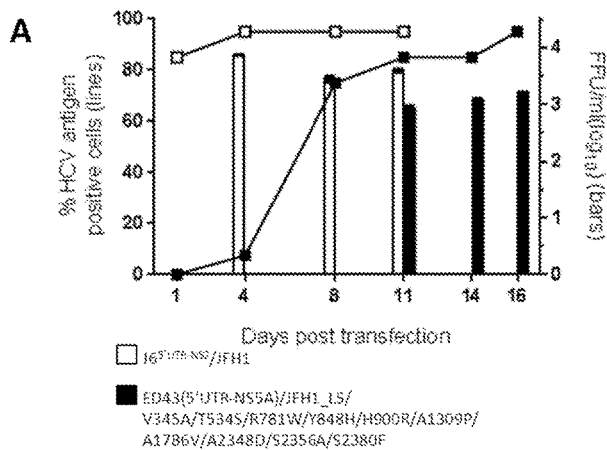
Fig. 11 A and B

Fig. 11 C

HCV CULTURE SYSTEMS AND DIRECT-ACTING ANTIVIRAL SENSITIVITY

CROSS REFERENCE TO RELATED APPLICATIONS

This application is a U.S. National Phase Application of PCT International Application Number PCT/DK2014/050343, filed on Oct. 21, 2014, designating the United States of America and published in the English language, which is an International Application of and claims the benefit of priority to Danish Patent Application No. PA 2013 70607, filed on Oct. 22, 2013. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-PLOUG36-009APC.txt, the date of creation of the ASCII text file is Mar. 22, 2016, and the size of the ASCII text file is 269 KB.

TECHNICAL FIELD OF THE INVENTION

The present invention relates to hepatitis C virus (HCV) culture systems of genotypes 1a, 3a, 4a, 5a, and 6a that directly contribute to HCV drug and vaccine development, to HCV basic research and to better-individualized treatment of HCV infected patients.

BACKGROUND OF THE INVENTION

Approximately 2-3% of the world population is chronically infected with hepatitis C virus (HCV), which can lead to liver cirrhosis and cancer.

The HCV genome is a positive-sense single-stranded RNA (~9600 bases) consisting of a single open reading frame (ORF), flanked by 5' and 3' untranslated regions (UTR). The ORF is translated and processed into 10 viral proteins, including structural proteins Core, E1, and E2, and nonstructural (NS) proteins p7, NS2, NS3, NS4A, NS4B, NS5A, and NS5B.

Clinical HCV isolates have been classified into seven major genotypes and numerous subtypes. Viral isolates from different genotypes and subtypes are highly diverse, and differ in their genomic sequence by ~30% and ~20%, respectively. Moreover, isolates from different genotypes, from different subtypes and even isolates within the same sub-type respond differently to current interferon-based treatment, and to newly released drugs that disrupt the function of important viral proteins. The inability to culture patient isolates representing HCV genotypes 1-7 has hampered antiviral drug and vaccine development.

To date, only a cloned strain, JFH1 (genotype 2a), has been able to spontaneously replicate in cultured Huh7 and Huh7.5 human hepatoma cells.

Using the replication capacity of the JFH1, the present inventors have previously developed JFH1-based HCV recombinants expressing various genomic regions of different genotypes.

These genotype recombinants have directly contributed to HCV basic research and antiviral drug development.

However, development of the direct-acting antivirals (DAAs) and the host-targeting drugs demands infectious culture systems expressing additional major drug targets that perform the entirety of the viral replication cycle.

SUMMARY OF THE INVENTION

The present invention relates to an isolated nucleic acid molecule which encodes a human hepatitis C virus wherein the hepatitis C virus comprises a 5'UTR-NS5A region derived from the group consisting of genotype 1a strains H77 (GenBank accession number AF009606) and TN (EF621489), genotype 3a strain S52 (GU814263), genotype 4a strain ED43 (GU814265), genotype 5a strain SA13 (AF064490), genotype 6a strain HK6a (KF589889), and further comprising the mutations F1468L in the NS3 Helicase and A1676S in NS4A.

F1468L in the NS3 Helicase corresponds to F1464L according to the H77 sequence (GenBank accession number AF009606) and A1676S in NS4A corresponds to A1672S according to the H77 sequence (GenBank accession number AF009606). One embodiment of the present invention relates to the isolated nucleic acid molecule according, wherein the genotype is genotype 1a, strain H77 and further comprises one or more of the adaptive mutations selected from the group consisting of D3001G, A1226G and Q1773H.

D3001G in NS5B corresponds to D2979G according to the H77 sequence (GenBank accession number AF009606).

A further embodiment of the present invention relates to the isolated nucleic acid molecule, wherein the genotype is genotype 1a, strain TN and further comprises one or more of the adaptive mutations selected from the group consisting of D3001G (D2979G in H77 sequence), A1226G and Q1773H.

Another embodiment of the present invention relates to the isolated nucleic acid molecule, wherein the genotype is genotype 3a, strain S52 and further comprises one or more of the adaptive mutations selected from the group consisting of D3001G (D2979G in H77 sequence), D871G, V1612E, H1819R and V2417A.

Another embodiment of the present invention relates to the isolated nucleic acid molecule, wherein the genotype is genotype 4a, strain ED43 and further comprises one or more of the adaptive mutations selected from the group consisting of R781W, A1309P and A1786V.

Another embodiment of the present invention relates to the isolated nucleic acid molecule, wherein the genotype is genotype 5a, strain SA13 and further comprises one or more of the adaptive mutations selected from the group consisting of D3001G (D2979G in H77 sequence), S294G and C1551F.

Another embodiment of the present invention relates to the isolated nucleic acid molecule, wherein the genotype is genotype 6a, strain HK6a and further comprises one or more of the adaptive mutations selected from the group consisting of D3001G (D2979G in H77 sequence), T387I, S872P, V1550L, L1790M and S2218P.

Another embodiment of the present invention relates to the isolated nucleic acid molecule, wherein the NS5B and the 3'UTR is from strain JFH1.

A further embodiment of the present invention relates to a composition comprising a nucleic acid molecule of the present invention suspended in a suitable amount of a pharmaceutical acceptable diluent or excipient.

Another embodiment of the present invention relates to a cassette vector for cloning viral genomes, comprising, inserted therein, the nucleic acid sequence of the present invention and having an active promoter upstream thereof.

Another embodiment of the present invention relates to a cell comprising the nucleic acid according to the present invention, the composition of the present invention or the cassette vector of the present invention.

Another embodiment of the present invention relates to a method for producing a hepatitis C virus particle, comprising culturing a cell according the present invention to allow the cell to produce the virus.

A further embodiment of the present invention relates to a hepatitis C virus particle obtainable by the method according to the present invention.

Another embodiment of the present invention relates to a hepatitis C vaccine comprising a hepatitis C virus particle according to the present invention or a part thereof.

A further embodiment of the present invention relates to a method for producing a hepatitis C virus vaccine comprising using a hepatitis C virus particle obtained from a method according to the present invention as an antigen.

Another embodiment of the present invention relates to an antibody against the hepatitis C virus particle according to the present invention.

A further embodiment of the present invention relates to a method for producing a cell, which replicates human hepatitis C virus and produces a virus particle comprising introducing a nucleic acid molecule into a cell, wherein said nucleic acid molecule is selected from the nucleic acids according to the present invention.

Another embodiment of the present invention relates to a cell obtainable by the method according to the present invention.

Another embodiment of the present invention relates to a method for producing a hepatitis C virus particle, comprising culturing a cell according to the present invention to allow the cell to produce the virus.

A further embodiment of the present invention relates to a method for in vitro producing a hepatitis C virus-infected cell comprising culturing a cell according to the present invention and infecting other cells with the produced virus particle in the culture.

Another embodiment of the present invention relates to a method for screening an anti-hepatitis C virus substance, comprising culturing at least one selected from the group consisting of a cell expressing the nucleic acids of the present invention, a cell according to the present invention and the hepatitis C virus particle obtainable from the method of the present invention together with a hepatitis C virus permissive cell, and detecting the replicating RNA or the virus particles in the resulting culture.

A further embodiment of the present invention relates to a method according to the present invention, wherein the substance is a protease inhibitor and/or a NS5A inhibitor.

BRIEF DESCRIPTION OF THE FIGURES

FIG. 3 shows characteristics of the HCV genotype-specific 5'UTR-NS5A recombinants in Huh7.5 cell cultures. a, all genotype(isolate) 5'UTR-NS5A specific recombinants contained NS5B-3'UTR from JFH1 (FIG. 1A). The final adapted recombinants showed efficient virus spread in transfection cultures (FIG. 1B). Sequence analysis of the passage-recovered viruses is shown in FIGS. 5-9. b, all amino acid positions are according to genotype 1a strain H77 (GenBank accession number AF009606). LSG indicates F1464L in NS3 helicase, A1672S in NS4A and D2929G in NS5B. c, peak representative HCV infectivity titers determined on filtered cell-culture supernatant collected on the indicated day post-transfection or post-infection; HCV RNA titers in passaged viruses were from the day with peak FFU titer.d, GenBank accession number KF134006. e, first-passage viruses collected from day 3, 5, and 7 (4.9 log 10 FFU/ml) for 1a(TN) and from day 16 and 18 (4.1 log 10 FFU/ml) for 1a(H77) 5-5A viruses were used for treatment assays shown in FIG. 2. f, HCV positive cells emerged at day 4 post transfection. g, infectivity titer was determined from the virus pool collected at the days indicated, and these viruses were used for drug treatment assays shown in FIG. 2. h, in a separate second-passage experiment, the virus pool from days 14, 16 and 18 had infectivity titer of 3.9 log 10 FFU/ml and RNA titer of 8.3 log 10 IU/ml. n.d., not determined.

FIG. 4 shows the EC50s of lead NS3/NS4A protease and NS5A inhibitors against HCV recombinants with 5'UTR-NS5A of genotype 1-6. a, all genotype 5'UTR-NS5A specific recombinants have NS5B and the 3'UTR from JFH1 (FIG. 1A). The concentration-response curves of each virus for the indicated inhibitors are shown in FIG. 2. The characteristics and sequences of the viruses are shown in FIG. 3 and FIGS. 5-9, respectively. b, The median effective concentration (EC50) was calculated from the concentration-response curves in the experiment (FIG. 2). Fold differences from J6/JFH1 for each inhibitor were calculated by dividing the EC50 of the respective recombinant by the EC50 of J6/JFH1. The 95% confidence interval of the EC50 is shown in FIG. 10. c, the ORF of the J6/JFH1 stock virus was sequenced and no mutations were identified.

FIG. 5 shows sequence analysis of the 1a(H77) and 1a(TN) 5'UTR-NS5A recombinant viruses. One milliliter of transfection-derived virus was passaged to naïve Huh7.5 cells (~4×$10^5$ cells), and filtered culture supernatant collected after peak infection (≥80% culture cells infected) was subjected to ORF sequence analysis. Primers used for RT-

Figure 2:
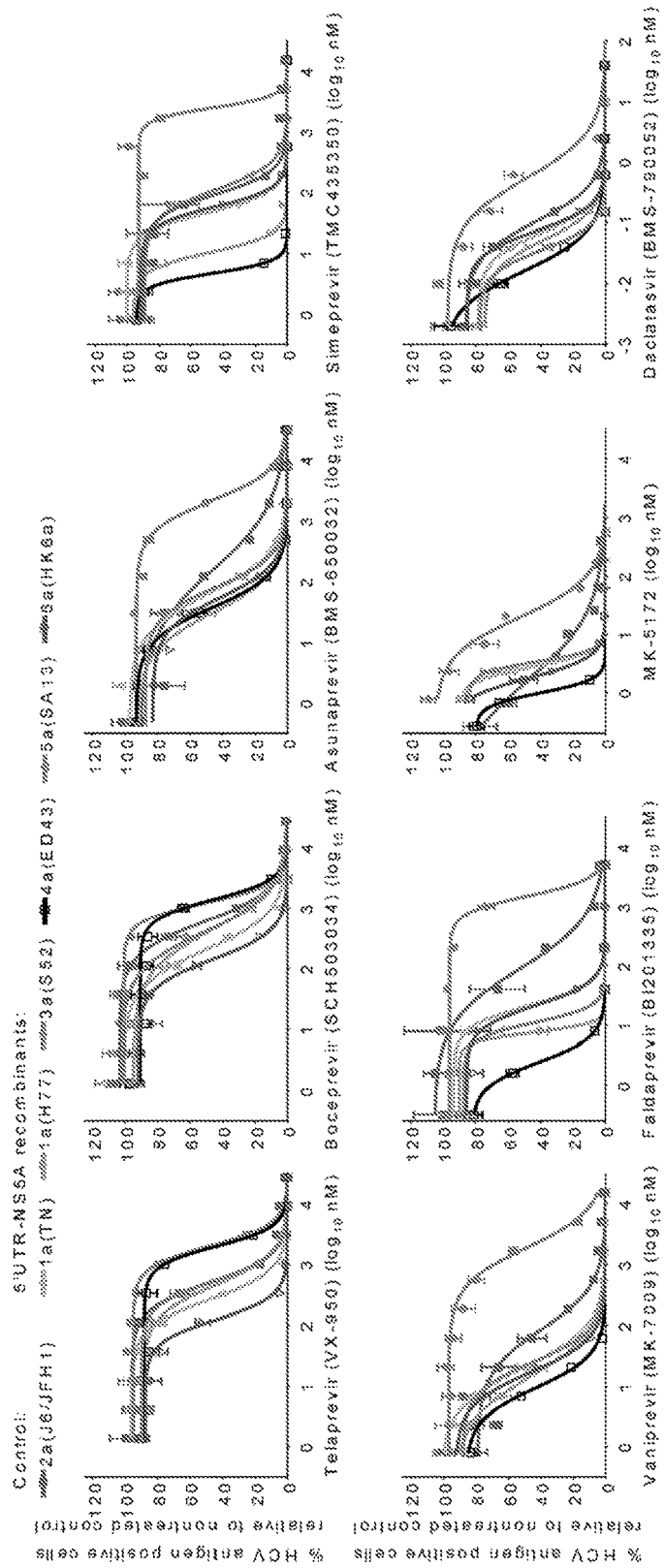
FIG. 2 shows that HCV genotype 1-6 specific 5'UTR-NS5A recombinants showed differential sensitivity to lead NS3/NS4A protease and NS5A inhibitors. Huh7.5 cells in 96-well culture plates were infected with 5'UTR-NS5A specific genotype(isolate) recombinants. For details on the 5-5A virus stocks see FIG. 3. J6/JFH1 was a first-passage stock with no mutations in the ORF. Cultures were treated with seven protease inhibitors and the NS5A inhibitor daclatasvir. Values are means of triplicates in the experiment with ±SEM. EC50 values for each drug and the different genotype viruses are shown in FIG. 4.

PCR were previously described. Nucleotide and amino acid positions of the specific recombinant with mutations are listed; the corresponding position of genotype 1a strain H77 (GenBank accession number AF009606) is given. Shading indicates the engineered mutations; the J6-derived LSG (F1464L, A1672S, and D2979G) mutations are shown in dark shading and the passaged recombinant-derived mutations are shown in light shading. Coding mutations identified in direct sequencing are listed; two capital letters separated by a slash indicates a nucleotide quasispecies (50/50), while a capital letter separated from a lowercase letter indicates a dominant/minor ratio. Dots indicate identity with original sequence. Peak viral infectivity titers and associated RNA titers of the passage viruses are shown in FIG. 3. a, viruses collected from first-passage culture supernatants at the indicated days were pooled and used for antiviral treatment (FIG. 2).

Figure 6:
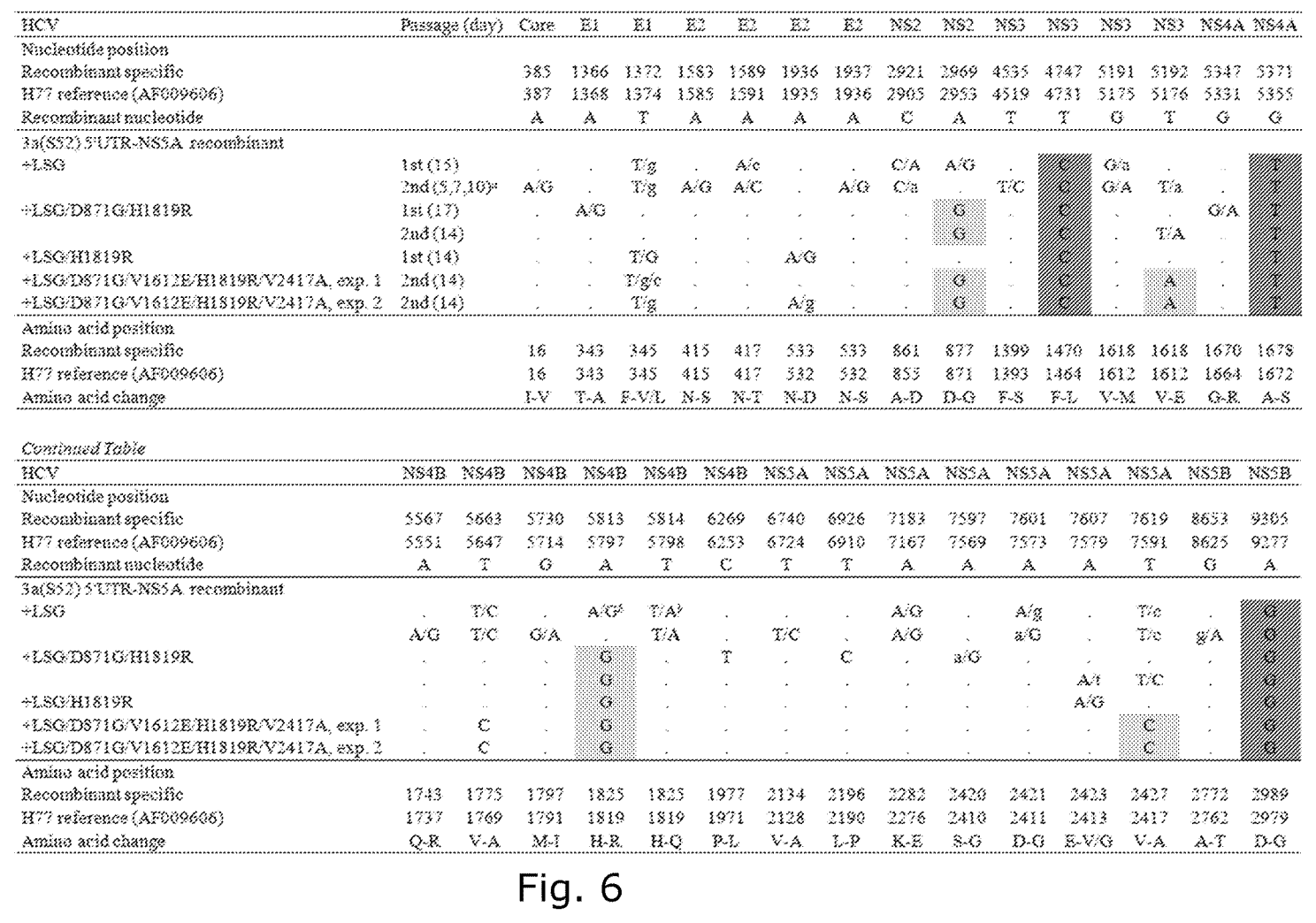

FIG. 6 shows sequence analysis of the passage-recovered 3a(S52) 5'UTR-NS5A recombinant viruses. For details, see legend of FIG. 5. One milliliter of transfection- or first passage-derived virus was passaged to naïve Huh7.5 cells (~4×10$^5$ cells). Primers used for RT-PCR were previously described. Peak viral infectivity titers and associated RNA titers of the passage viruses are shown in FIG. 3. a, a virus stock made from second-passage supernatants collected at days 5, 6, and 10 was used for antiviral treatment (FIG. 2). b, cloning analysis of PCR products (8 clones) showed that these mutations did not co-exist.

FIG. 7 shows sequence analysis of the 4a(ED43) 5'UTR-NS5A recombinant viruses. For details, see legend of FIG. 5. One milliliter of transfection- or first passage-derived virus was passaged to naïve Huh7.5 cells (~4×10$^5$ cells). Primers used for RT-PCR were previously described. Peak viral infectivity titers and associated RNA titers of the passage viruses are shown in FIG. 3. a, the engineered mutation G was partially changed (50/50) to wild-type nucleotide A. b, a virus stock made from a second-passage supernatants collected at days 11 and 13 (FIG. 3) was used for antiviral treatment (FIG. 2). c, a virus stock made from a separate second-passage experiment; supernatants were collected at days 14, 16 and 18 (FIG. 3 legend).

FIG. 8 shows sequence analysis of the 5a(SA13) 5'UTR-NS5A recombinant viruses. For details, see legend of FIG. 5. One milliliter of transfection- or first passage-derived virus was passaged to naïve Huh7.5 cells (~4×10$^5$ cells). Primers used for RT-PCR were previously described (6-8). Peak viral infectivity titers and associated RNA titers of the passage viruses were shown in FIG. 3. a, a virus stock made from second-passage supernatants collected at days 7, 9, and 12 was used for antiviral treatment (FIG. 2).

FIG. 9 shows sequence analysis of the 6a(HK6a) 5'UTR-NS5A recombinant viruses. For details, see legend of FIG. 5. One milliliter of transfection- or first passage-derived virus was passaged to naïve Huh7.5 cells (~4×10$^5$ cells). Primers used for RT-PCR were previously described. Peak viral infectivity titers and associated RNA titers of the passage viruses were shown in FIG. 3. a, a virus stock made from second-passage supernatants collected at days 14 and 18 was used for antiviral treatment (FIG. 2).

Figure 1:
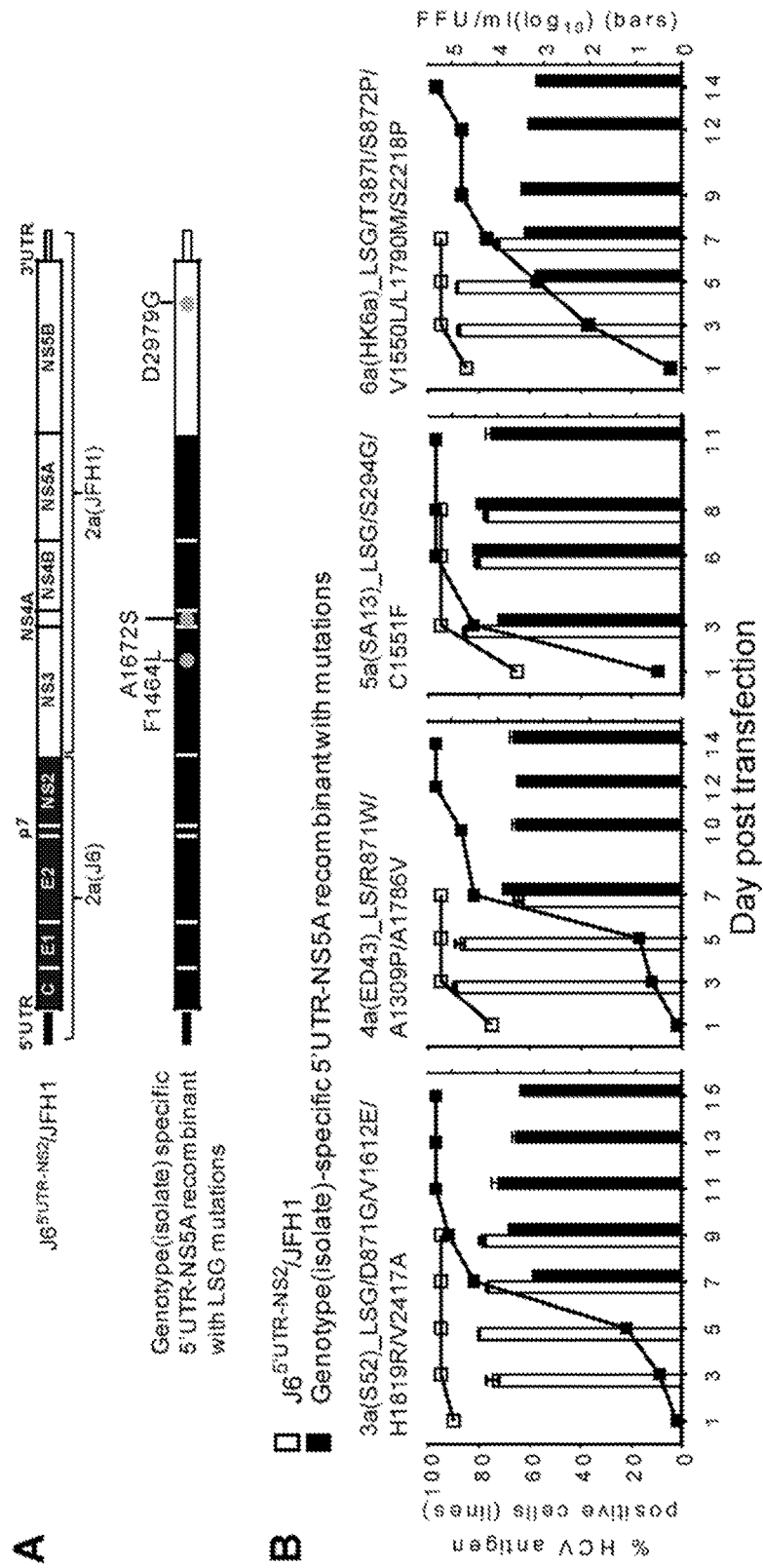
FIG. 1 shows replication characteristics of HCV recombinants with 5'UTR-NS5A of genotypes 3a, 4a, 5a, and 6a in transfected Huh7.5 cells. (A) Schematic diagram of J65'UTR-NS2/JFH1 and HCV recombinants with genotype (isolate)-specific 5'UTR-NS5A (5-5A) and JFH1 NS5B-3'UTR. Mutations LSG (F1464L, A1672S, and D2979G) used to adapt the 5-5A recombinants are indicated. (B) In vitro generated RNA transcripts of genotype(isolate)-specific 5-5A recombinants with engineered mutations (aa positions corresponding to the genotype 1a strain H77) were transfected into Huh7.5 cells, the HCV Core and/or NS5A antigens were detected by immunostaining, and the percentage of positive cells was estimated using fluorescence microscopy (left y-axis; lines). HCV infectivity titers in supernatants at peak of infection (≥80% HCV positive culture cells) were determined by FFU assay (mean of triplicate infections ±SEM, right y-axis; bar graphs). J65'UTR-NS2/JFH1 was used as a transfection control. Duplicate transfection experiments were performed for these recombinants with similar results. Details on transfection and second-passage experiments for these and additional recombinants are shown in FIG. 3.

FIG. 10 shows the EC50 of lead NS3/NS4A protease and NS5A inhibitors against HCV recombinants with 5'UTR-NS5A of genotype 1-6. a, all genotype 5'UTR-NS5A specific recombinants have NS5B and the 3'UTR from JFH1 (FIG. 1). The dose-response curves of each virus against the indicated inhibitor are shown in FIG. 2. The characteristics and sequences of the viruses are shown in FIG. 3 and FIGS. 5-9, respectively. b, the J6/JFH1 stock virus was sequenced and no mutations were identified.

Figure 11C:
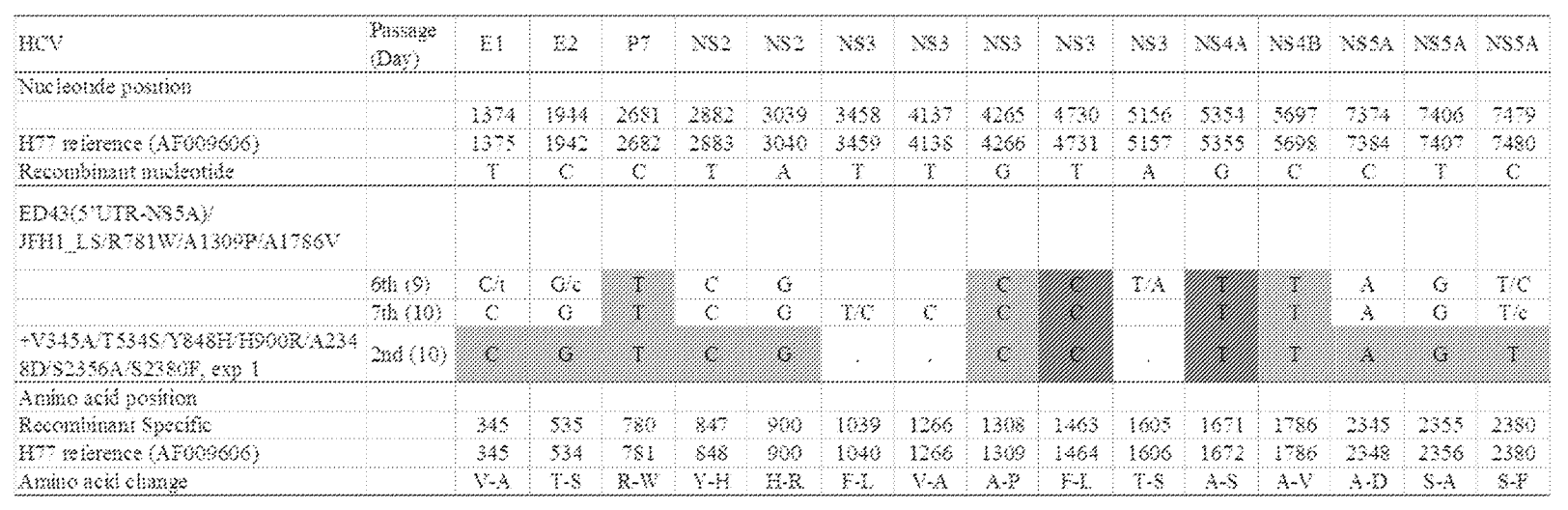

FIG. 11 shows the growth characteristics and sequence analysis of the further passaged 4a(ED43) 5'UTR-NS5A recombinant. A, In vitro generated RNA transcripts of the 4a(ED43) 5'UTR-NS5A recombinant with engineered mutations (aa positions corresponding to the genotype 1a strain H77) were transfected into Huh7.5 cells, the HCV Core and/or NS5A antigens were detected by immunostaining, and the percentage of positive cells was estimated using fluorescence microscopy (left y-axis; lines). HCV infectivity titers in supernatants at peak of infection (≥80% HCV positive culture cells) were determined by FFU assay (mean of triplicate infections ±SEM, right y-axis; bar graphs). J65'UTR-NS2/JFH1 was used as a transfection control. Duplicate transfection experiments were performed for these recombinants with similar results. B, Additional details on transfection and second-passage experiments of ED43 (5'UTR-NS5A)/JFH1_LS/V345A/T534S/R781W/Y848H/H900R/A1309P/A1786V/A2348D/S 2356A/S2380F. C, Sequence analysis of the further passaged 4a(ED43) 5'UTR-NS5A recombinant virus.

DETAILED DESCRIPTION OF THE INVENTION

Recently, the present inventors identified three amino acid changes F1464L in NS3 helicase, A1672S in NS4A and D2979G in NS5B, designated the LSG mutations.

Positions of mutations are according to the reference strain H77 (GenBank accession number AF009606).

The LSG mutations have permitted the development of full-length HCV infectious culture systems of genotypes 1a (strain TN), 2a (J6), and 2b (J8, DH8, and DH10).

Recombinants based on the NS5B and 3'UTR from JFH1 contributed to the development of these full-length culture systems.

Here, the present inventors constructed novel JFH1-based HCV recombinants expressing the regions spanning the 5'UTR, Core, E1, E2, p7, NS2, NS3, NS4A, NS4B, and NS5A (designated 5'UTR-NS5A) of genotypes 1a (strains TN and H77), 3a (strain S52), 4a (ED43), 5a (SA13), and 6a(HK6a), with only the NS5B and 3'UTR from JFH1 (see examples).

These recombinant constructs were engineered with the LSG mutations.

The 5'UTR-NS5A recombinants with LSG mutations initially replicated to low levels in RNA-transfected cell cultures.

Through long-term follow up of the transfection cultures, the present inventors recovered viruses that could be passaged to naïve Huh7.5 cells.

After first- and second-passages, the present inventors sequenced the open reading frame of the recovered viruses and identified additional mutations.

By engineering the passage-derived mutations back to the parental genome, the present inventors were able to generate 5'UTR-NS5A recombinants of genotype 1a, 3a, 4a, 5a, and 6a with efficient growth in cultured Huh7.5 cells.

The final recombinants the present inventors have developed are as listed below:

Genotype 3a virus, strain S52(5'UTR-NS5A)/JFH1_LSG/D871G/V1612E/H1819R/V2417A (SEQ ID NOs 3 and 9)

Genotype 4a virus, strain virus, ED43(5'UTR-NS5A)/JFH1_LS/R781W/A1309P/A1786V (SEQ ID NOs 4 and 10)

Genotype 5a virus, strain SA13(5'UTR-NS5A)/JFH1_LSG/S294G/C1551F (SEQ ID NOs 5 and 11)

Genotype 6a virus, strain HK6a(5'UTR-NS5A)/JFH1_LSG/T387I/S872P/V1550L/L1790M/S2218P (SEQ ID NOs 6 and 12)

In addition, the present inventors found that mutations previously identified for adaption of LSG-based TN 5'UTR-NS5A recombinant were able to adapt another genotype 1a clone H77 5'UTR-NS5A recombinant that contained the LSG mutations.

Thus, these two 1a 5'UTR-NS5A recombinant viruses were included in this study:

Genotype 1a virus, strain H77(5'UTR-NS5A)/JFH1_LSG/A1226G/Q1773H (SEQ ID NOs 1 and 7)

Genotype 1a virus, strain TN(5'UTR-NS5A)/JFH1_LSG/A1226G/Q1773H (SEQ ID NOs 2 and 8)

In addition, after sixth and seventh passages of the 4a (ED43) 5'UTR-NS5A recombinant ED43(5'UTR-NS5A)/JFH1_LSG/R781W/A1309P/A1786V (SEQ ID NOs 4 and 10), the present inventors sequenced the open reading frame of the recovered virus and identified additional mutations which further increased efficiency of viral replication of the 4a (ED43) 5'UTR-NS5A recombinant.

Thus, this additional genotype 4a 5'UTR-NS5A recombinant virus was included in this study:

Genotype 4a virus, strain ED43(5'UTR-NS5A)/JFH1_LS/V345A/T534S/R781W/Y848H/H900R/A1309P/A1786V/A2348D/S 2356A/S2380F (SEQ ID NOs 13 and 14).

The 5'UTR-NS5A recombinants are the first infectious culture systems expressing the NS3 helicase of genotypes 3, 4, 5, and 6, the NS4B protein of genotypes 4, 5, and 6, and the NS3/NS4A protease of genotype 4.

These systems are therefore very good for testing of drug combinations because they have 5UTR-NS5A from the same isolate on the same genome.

Thus, the 5'UTR-NS5A infectious culture systems represent the most advanced cultures for HCV genotypes 3, 4, 5, and 6. Importantly, the 5'UTR-NS5A recombinant viruses did not acquire mutations in the NS3 protease and the NS5A domain I after passage to naïve human hepatoma Huh7.5 cells.

These properties make the 5'UTR-NS5A recombinants an ideal panel for pre-clinical testing of protease and NS5A inhibitors, or combination of these inhibitors, without the confounding effects of mutations in the drug targets.

The present inventors have demonstrated the genotype- and concentration-specific viral responses to the lead NS3/NS4A protease and NS5A inhibitors (see examples), showing their potentials in a high throughput drug discovery and development program.

Lack of infectious cell culture systems representing the six major HCV genotypes has hampered basic research and drug development.

Thus, the development of the most advanced infectious culture systems for HCV genotypes 3, 4, 5, and 6 permits detailed virological studies and applications previously difficult or not possible for genotype 1, 3, 4, 5, and 6 viruses.

Importantly, the identified mutations and the approach applied could potentially be used to develop full-length culture systems for these strains (or genotypes), and possibly for other HCV genotype patient isolates.

The 5'UTR-NS5A culture systems of genotypes 1a, 3a, 4a, 5a, and 6a could directly contribute to HCV drug and vaccine development and to HCV basic research and better-individualized treatment of HCV infected patients.

Thus, it will be of great interest for the pharmaceutical companies and the HCV-related research communities.

Thus, the key features of the present invention are: 1) The 5'UTR-NS5A infectious culture systems represent the most advanced cultures for HCV genotypes 1, 3, 4, 5, and 6 prototype isolates; they included genotype-specific genome regions not found in previously developed systems. 2) These recombinant viruses did not acquire mutations in the NS3 protease or the NS5A domain I after passage, making them an ideal panel for pre-clinical testing of protease and NS5A inhibitors, or combinations thereof; 3) These recombinant viruses also permitted testing of drugs targeting other regions from the 5'UTR through NS5A; 4) The use of LSG mutations facilitated the development of 5'UTR-NS5A recombinants of other genotypes, indicating the cross-genotype adaptation effect of the LSG mutations. Thus, they could also be used for culture development of other clinical HCV isolates; 5) The novel mutations identified in this study could lead to culture development of a specific 5'UTR-NS5A or full-length HCV isolates.

Nucleic Acid Molecules (cDNA Clones and RNA Transcripts)

It is therefore an object of the present invention to provide an isolated nucleic acid molecule which encodes a human hepatitis C virus wherein the hepatitis C virus comprises a 5'-UTR-NS5A region derived from the group consisting of genotype 1a strains H77 and TN, genotype 3a strain S52, genotype 4a strain ED43, genotype 5a strain SA13, genotype 6a strain HK6a, and further comprising the mutations F1468L in NS3 and A1676S in NS4A.

F1468L in the NS3 Helicase corresponds to F1464L according to the H77 sequence (GenBank accession number AF009606) and A1676S in NS4A corresponds to A1672S according to the H77 sequence (GenBank accession number AF009606).

In another object of the present invention is the hepatitis C virus comprises a 5'-UTR-NS5A region independent of one or both of the above mentioned F1468L and A1676S mutations.

The mutations may also be mutations F1468L in NS3, A1676S in NS4A, and D3001G in NS5B.

D3001G in NS5B corresponds to D2979G according to the H77 sequence (GenBank accession number AF009606).

Another object of the present invention is to provide an isolated nucleic acid molecule which encodes a human hepatitis C virus wherein the hepatitis C virus comprises a 5'UTR-NS5A region derived from the group consisting of genotype 1a strains H77 and TN, genotype 3a strain S52, genotype 4a strain ED43, genotype 5a strain SA13, genotype 6a strain HK6a.

Such isolated nucleic acid molecule may comprise adaptive mutations. These mutations may be specific for each genotype.

The present inventors have identified recombinants that comprise further adaptive mutations:

Genotype 3a virus, strain S52(5'UTR-NS5A)/JFH1_LSG/D871G/V1612E/H1819R/V2417A (SEQ ID NOs 3 and 9)

Genotype 4a virus, strain virus, ED43(5'UTR-NS5A)/JFH1_LS/R781W/A1309P/A1786V (SEQ ID NOs 4 and 10)

Genotype 5a virus, strain SA13(5'UTR-NS5A)/JFH1_LSG/S294G/C1551F (SEQ ID NOs 5 and 11)

Genotype 6a virus, strain HK6a(5'UTR-NS5A)/JFH1_LSG/T387I/S872P/V1550L/L1790M/S2218P (SEQ ID NOs 6 and 12)

Genotype 1a virus, strain H77(5'UTR-NS5A)/JFH1_LSG/A1226G/Q1773H (SEQ ID NOs 1 and 7)

Genotype 1a virus, strain TN(5'UTR-NS5A)/JFH1_LSG/A1226G/Q1773H (SEQ ID NOs 2 and 8)

Genotype 4a virus, strain ED43(5'UTR-NS5A)/JFH1_LS/V345A/T534S/R781W/Y848H/H900R/A1309P/A1786V/A2348D/S 2356A/S2380F (SEQ ID NOs 13 and 14)

Adaptive Mutations

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-RNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

One embodiment of the present invention relates to adaptive mutations, wherein the adaptive mutation is a mutation that can be observed by clonal or direct sequencing of recovered replicating genomes of the sequences of the present invention.

Thus in a further embodiment, the present invention relates to nucleic acid molecules according to the present invention, wherein said molecule comprises one or more adaptive mutations in p7, NS2, NS3, NS4A, NS4B, NS5A or NS5B singly or in combination.

In the context of the present invention, the term "adaptive mutation" is meant to cover mutations identified in passaged viruses that provide the original and any other HCV sequence the ability to grow efficiently in culture. Furthermore, all introductions of mutations into the sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition, some of the described mutations might change the function of the concerned proteins in favourable ways, which might be exploited in other experimental systems employing these proteins.

This also includes other HCV genomes with adaptive mutations, all of them, combinations of them or individual mutations that grow in culture.

It should be understood that any feature and/or aspect discussed above in connection with the mutations according to the invention apply by analogy to both single mutations and any combination of the mutations.

In another embodiment all the amino acid changes observed herein are provided by the present application. The skilled addressee can easily obtain the same amino acid change by mutating another base of the codon and hence all means of obtaining the given amino acid sequence is intended.

The isolated nucleic acid molecules of the present invention can comprise one, two or more adaptive mutations.

Thus, relates one embodiment of the present invention to an isolated nucleic acid molecule of the present invention, wherein the genotype is genotype 1a, strain H77 and further comprises one or more of the adaptive mutations selected from the group consisting of D3001G, A1226G and Q1773H.

D3001G in NS5B corresponds to D2979G according to the H77 sequence (GenBank accession number AF009606).

Another embodiment of the present invention relates to an isolated nucleic acid molecule of the present invention, wherein the genotype is genotype 1a, strain H77 and further comprises the adaptive mutations D3001G (namely D2979G in H77 sequence), A1226G and Q1773H (for example as in SEQ ID NO: 1 and 7).

Another embodiment of the present invention relates to an isolated nucleic acid molecule of the present invention, wherein the genotype is genotype 1a, strain TN and further comprises one or more of the adaptive mutations selected from the group consisting of D3001G (D2979G in H77 sequence), A1226G and Q1773H.

Another embodiment of the present invention relates to an isolated nucleic acid molecule of the present invention, wherein the genotype is genotype 1a, strain TN and further comprises the adaptive mutations D3001G (D2979G in H77 sequence), A1226G and Q1773H (for example as in SEQ ID NO: 2 and 8).

Another embodiment of the present invention relates to an isolated nucleic acid molecule of the present invention, wherein the genotype is genotype 3a, strain S52 and further comprises one or more of the adaptive mutations selected from the group consisting of D3001G (D2979G in H77 sequence), D871G, V1612E, H1819R and V2417A.

Another embodiment of the present invention relates to an isolated nucleic acid molecule of the present invention, wherein the genotype is genotype 3a, strain S52 and further comprises the adaptive mutations D3001G (D2979G in H77 sequence), D871G, V1612E, H1819R and V2417A for example as in (SEQ ID NO: 3 and 9).

Another embodiment of the present invention relates to an isolated nucleic acid molecule of the present invention, wherein the genotype is genotype 4a, strain ED43 and further comprises one or more of the adaptive mutations selected from the group consisting of R781W, A1309P and A1786V.

Another embodiment of the present invention relates to an isolated nucleic acid molecule of the present invention, wherein the genotype is genotype 4a, strain ED43 and further comprises the adaptive mutations R781W, A1309P and A1786V (for example as in SEQ ID NO: 4 and 10).

Another embodiment of the present invention relates to an isolated nucleic acid molecule of the present invention, wherein the genotype is genotype 5a, strain SA13 and further comprises one or more of the adaptive mutations selected from the group consisting of D3001G (D2979G in H77 sequence), S294G and C1551F.

Another embodiment of the present invention relates to an isolated nucleic acid molecule of the present invention, wherein the genotype is genotype 5a, strain SA13 and further comprises the adaptive mutations D3001G (D2979G in H77 sequence), S294G and C1551F (for example as in SEQ ID NO: 5 and 11).

Another embodiment of the present invention relates to an isolated nucleic acid molecule of the present invention, wherein the genotype is genotype 6a, strain HK6a and further comprises one or more of the adaptive mutations selected from the group consisting of D3001G (D2979G in H77 sequence), T387I, S872P, V1550L, L1790M and S2218P.

Another embodiment of the present invention relates to an isolated nucleic acid molecule of the present invention, wherein the genotype is genotype 6a, strain HK6a and further comprises the adaptive mutations D3001G (D2979G in H77 sequence), T387I, S872P, V1550L, L1790M and S2218P (for example as in SEQ ID NO: 6 and 12).

The isolated nucleic acid molecule of the present invention can comprise NS5B and 3'-UTR from strain JFH1.

The isolated nucleic acid molecule of the present invention can also comprise NS5B and 3'-UTR from a strain that is different from strain JFH1.

In one embodiment of the present invention is the isolated nucleic acid molecule capable of infectivity in vivo.

The terms "isolate" and "strain" are used herein interchangeably.

The nucleic acid molecules of the present invention may comprise further changes in the sequences. Such sequences can be described by sequence identity.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

In another embodiment the two sequences are of different length and gaps are seen as different positions.

One may manually align the sequences and count the number of identical amino acids. Alternatively, alignment of two sequences for the determination of percent identity may be accomplished using a mathematical algorithm. Such an algorithm is incorporated into the NB LAST and XBLAST programs of (Altschul et al. 1990). BLAST nucleotide searches may be performed with the NBLAST program, score=100, wordlength=12, to obtain nucleotide sequences homologous to a nucleic acid molecule of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. Alternatively, sequence identity may be calculated after the sequences have been aligned e.g. by the BLAST program in the EMBL database. Generally, the default settings with respect to e.g. "scoring matrix" and "gap penalty" may be used for alignment. In the context of the present invention, the BLAS TN and PSI BLAST default settings may be advantageous.

The percent identity between two sequences may be determined using techniques similar to those described above, with or without allowing gaps. In calculating percent identity, only exact matches are counted.

An embodiment of the present invention thus relates to sequences of the present invention that has some degree of sequence variation.

Another embodiment relates to a genotype 3a virus, strain S52(5'UTR-NS5A)/JFH1_LSG/D871G/V1612E/H1819R/V2417A (SEQ ID NO 3) in which the nucleic acid molecule comprises the nucleic acid sequence with a sequence identity of at least 80% to that of SEQ ID NO: 3 or an amino acid sequence with a sequence identity of at least 80% to that of SEQ ID NO: 9.

In another embodiment, the nucleic acid comprises a sequence sharing at least 85% identity with that set forth in SEQ ID NO: 3, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 9, such as 90% identity, 91% identity, 92% identity, 93% identity, 94% identity, 95% identity, 96% identity, 97% identity, 98% identity, or 99% identity.

Another embodiment relates to a genotype 4a virus, strain virus, ED43(5'UTR-NS5A)/JFH1_LS/R781W/A1309P/A1786V (SEQ ID NO 4) in which the nucleic acid molecule comprises the nucleic acid sequence with a sequence identity of at least 80% to that of SEQ ID NO: 4 or an amino acid sequence with a sequence identity of at least 80% to that of SEQ ID NO: 10.

In another embodiment, the nucleic acid comprises a sequence sharing at least 85% identity with that set forth in SEQ ID NO: 4, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 10, such as 90% identity, 91% identity, 92% identity, 93% identity, 94% identity, 95% identity, 96% identity, 97% identity, 98% identity, or 99% identity.

Another embodiment relates to a genotype 5a virus, strain SA13(5'UTR-NS5A)/JFH1_LSG/S294G/C1551F (SEQ ID NO 5) in which the nucleic acid molecule comprises the nucleic acid sequence with a sequence identity of at least 80% to that of SEQ ID NO: 5 or an amino acid sequence with a sequence identity of at least 80% to that of SEQ ID NO: 11.

In another embodiment, the nucleic acid comprises a sequence sharing at least 85% identity with that set forth in SEQ ID NO: 5, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 11, such as 90% identity, 91% identity, 92% identity, 93% identity, 94% identity, 95% identity, 96% identity, 97% identity, 98% identity, or 99% identity.

Another embodiment relates to a genotype 6a virus, strain HK6a(5'UTR-NS5A)/JFH1_LSG/T387I/S872P/V1550L/L1790M/S2218P (SEQ ID NO 6) in which the nucleic acid molecule comprises the nucleic acid sequence with a sequence identity of at least 80% to that of SEQ ID NO: 6 or an amino acid sequence with a sequence identity of at least 80% to that of SEQ ID NO: 12.

In another embodiment, the nucleic acid comprises a sequence sharing at least 85% identity with that set forth in SEQ ID NO: 6, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 12, such as 90% identity, 91% identity, 92% identity, 93% identity, 94% identity, 95% identity, 96% identity, 97% identity, 98% identity, or 99% identity.

Another embodiment relates to a genotype 1a virus, strain H77(5'UTR-NS5A)/JFH1_LSG/A1226G/Q1773H (SEQ ID NO 1) in which the nucleic acid molecule comprises the nucleic acid sequence with a sequence identity of at least 80% to that of SEQ ID NO: 1 or an amino acid sequence with a sequence identity of at least 80% to that of SEQ ID NO: 7.

In another embodiment, the nucleic acid comprises a sequence sharing at least 85% identity with that set forth in SEQ ID NO: 1, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 7, such as 90% identity, 91% identity, 92% identity, 93% identity, 94% identity, 95% identity, 96% identity, 97% identity, 98% identity, or 99% identity.

Another embodiment relates to a genotype 1a virus, strain TN(5'UTR-NS5A)/JFH1_LSG/A1226G/Q1773H (SEQ ID NO 2) in which the nucleic acid molecule comprises the nucleic acid sequence with a sequence identity of at least 80% to that of SEQ ID NO: 2 or an amino acid sequence with a sequence identity of at least 80% to that of SEQ ID NO: 8.

In another embodiment, the nucleic acid comprises a sequence sharing at least 85% identity with that set forth in SEQ ID NO: 2, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 8, such as 90% identity, 91% identity, 92% identity, 93% identity, 94% identity, 95% identity, 96% identity, 97% identity, 98% identity, or 99% identity.

Another embodiment relates to a genotype 4a virus, strain ED43(5'UTR-NS5A)/JFH1_LS/V345A/T534S/R781W/Y848H/H900R/A1309P/A1786V/A2348D/S 2356A/S2380F (SEQ ID NO 13) in which the nucleic acid molecule comprises the nucleic acid sequence with a sequence identity of at least 80% to that of SEQ ID NO: 2 or an amino acid sequence with a sequence identity of at least 80% to that of SEQ ID NO: 8.

In another embodiment, the nucleic acid comprises a sequence sharing at least 85% identity with that set forth in SEQ ID NO: 13, such as 90% identity, 91% identity, 92% identity, 93% identity, 94% identity, 95% identity, 96% identity, 97% identity, 98% identity, or 99% identity.

In another embodiment, the amino acid comprises a sequence sharing at least 85% identity with that set forth in SEQ ID NO: 14, such as 90% identity, 91% identity, 92% identity, 93% identity, 94% identity, 95% identity, 96% identity, 97% identity, 98% identity, or 99% identity.

It should be noted that while several of the sequences in the present application (e.g., SEQ ID NOs: 1-6 and 13) are DNA sequences (NOs. 7-12 and 14 are amino acid sequences), the present invention contemplates the corresponding RNA sequence, and DNA and RNA complementary sequences as well.

Thus, in cases where a DNA sequence is mentioned refers such DNA sequence also to the RNA equivalent i.e. with Ts exchanged with Us as well as their complimentary sequences.

In another embodiment, the HCV nucleic acid is a DNA that codes on expression or after in vitro transcription for a replication-competent HCV RNA genome, or is itself a replication-competent HCV RNA genome.

Various modifications for example of the 5' and 3' UTR are also contemplated by the invention.

In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or the green fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA.

Thus, where particular sequences of nucleic acids of the invention are set forth, both DNA and corresponding RNA are intended, including positive and negative strands thereof.

In a further embodiment, the nucleic acid sequences or the nucleic acid sequences with any mutation described in this document is obtained by any other means than what is described above.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

Thus, in one embodiment the present invention provides a cassette vector for cloning viral genomes, comprising, inserted therein, the nucleic acid sequence according to the invention and having an active promoter upstream thereof.

Titer

To determine the efficiency of the developed system, HCV RNA titers are determined in IU/ml (international units/ml) with Taq-Man Real-Time-PCR and infectious HCV titers are determined with a focus forming unit assay.

The infectious titers are determined as TCID50/ml (median tissue culture infectious dose/ml) or FFU/ml (focus forming unites/ml); in such method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and TCID50 or FFU per ml, respectively) or intracellularly, in lysates of pelleted cells (given as IU and TCID50 or FFU related to a the given cell number or culture plate wells, which was lysed).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ TCID50/ml or above following transfection and/or subsequent viral passage, such as a titer of at least $10^3$ TCID50/ml, such as a titer of at least $10^4$ TCID50/ml, such as a titer of at least $10^5$ TCID50/ml, such as a titer of at least $10^6$ TCID50/ml, such as a titer of at least $10^7$ TCID50/ml, such as a titer of at least $10^8$ TCID50/ml, such as a titer of at least $10^9$ TCID50/ml or such as a titer of at least $10^{10}$ TCID50/ml.

In another embodiment, the present invention relates to a nucleic acid molecule according to the invention, wherein said molecule is capable of generating a HCV infectivity titer of at least $10^2$ FFU/ml or above following transfection and/or subsequent viral passage, such as a titer of at least $10^3$ FFU/ml, such as a titer of at least $10^4$ FFU/ml, such as a titer of at least $10^5$ FFU/ml, such as a titer of at least $10^6$ FFU/ml, such as a titer of at least $10^7$ FFU/ml, such as a titer of at least $10^8$ FFU/ml, such as a titer of at least $10^9$ FFU/ml or such as a titer of at least $10^{10}$ FFU/ml.

It is of course evident to the skilled addressee that the titers described here are obtained using the assay described in this text. Any similar or equivalent titer determined by any method is thus evidently within the scope of the present invention.

Compositions

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response.

Adjuvants include, but are not limited to, complete Freund's adjuvant, incomplete Freund's adjuvant, saponin, mineral gels such as aluminum hydroxide, surface active substances such as lysolecithin, pluronicpolyols, polyanions, peptides, oil or hydrocarbon emulsions, keyhole limpet hemocyanins, dinitrophenol, and potentially useful human adjuvants such as BCG (bacilleCalmette-Guerin) and *Corynebacterium parvum*.

Preferably, the adjuvant is pharmaceutically acceptable.

Thus relates one embodiment of the present invention to a composition comprising a nucleic acid molecule according to the present invention suspended in a suitable amount of a pharmaceutical acceptable diluent or excipient.

Cells

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non-hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus relates one embodiment of the present invention to a cell comprising the nucleic acid according to the present invention, the composition of present invention or the cassette vector of the present invention.

Another embodiment of the present invention relates to a method for producing a cell, which replicates human hepatitis C virus and produces a virus particle comprising introducing a nucleic acid molecule of the present invention into a cell.

In a preferred embodiment is the cella Huh7.5 cell.

Another embodiment of the present invention relates to a cell obtainable by the methods of the present invention.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9 and the low-density lipid receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

Virus Particle

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow anyone of them to produce the virus.

In another embodiment the inventions provides a hepatitis C virus particle obtainable by the method described.

Because the invention provides, inter alia, infectious HCV RNA, the invention provides a method for infecting an animal with HCV, which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

In one embodiment the introduced mutations attenuate the virus in vivo.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

In one embodiment, the method further comprises isolating infectious HCV. In another embodiment, the method further comprises freezing aliquots of said infectious HCV.

According to this aspect of the invention, and in one embodiment, the HCV is infectious following thawing of said aliquots, and in another embodiment, the HCV is infectious following repeated freeze-thaw cycles of said aliquots.

A further embodiment of the present invention relates to a method for in vitro producing a hepatitis C virus-infected cell comprising culturing a cell according to the present invention and infecting other cells with the produced virus particle in the culture.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Alternatively, the number of antigen-expressing cells is determined. Resistance is given if a reduced inhibition of the replication and release of viral particles can be observed with the normal concentration of the active substance. The nucleotide and amino acid replacements responsible for the therapy resistance can be determined by direct amplification or recloning of the HCV-RNA (for example by the means of RT-PCR) and sequence analysis. By cloning the relevant replacement(s) into the original construct, the replacements' causality for the resistance to therapy can be proven.

While the replicon systems facilitated testing of drugs interfering with replication such as NS3/4A protease and polymerase inhibitors, the variant genomes obtained in the present invention may prove useful for different research topics.

The systems developed in this invention are ideal candidates for specific testing of therapeutics in general and therapeutics targeting viral entry, assembly and release.

Genomes with the sequences of the present invention are valuable for testing of neutralizing antibodies and other drugs acting on entry level, such as fusion inhibitors.

In one embodiment the present invention relates to a method for identifying neutralizing antibodies.

In another embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

An aspect of the present invention relates to a method for screening an anti-hepatitis C virus substance, comprising culturing at least one selected from the group consisting of a cell comprising the nucleic acids of the present invention, a cell of the present invention and the hepatitis C virus particle obtainable from the method together with a hepatitis C virus permissive cell, and detecting the replicating RNA or the virus particles in the resulting culture.

The recombinant viruses identified in the examples of the present application did not acquire mutations in the NS3 protease or the NS5A domain I after passage, making them an ideal panel for pre-clinical testing of protease and NS5A inhibitors, or combinations of inhibitors.

These recombinant viruses also permitted testing of drugs targeting other regions from the 5'UTR through NS5A.

Thus, a preferred embodiment of the present invention is the substance is a protease inhibitor and/or a NS5A inhibitor.

Another embodiment of the present invention is the drug target selected from the group consisting of 5'UTR, Core, E1, E2, p7, NS2, NS3 (protease and helicase), NS4A, NS4B, NS5A, NS5B and 3'UTR.

Vaccines

The construct according to the invention by itself can also be used for various purposes in all its embodiments. This includes the construction of hepatitis C viruses or HCV-like particles and their production in cell culture as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, maybe expressed, following infection, predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

Uses

The cell culture system developed of the present invention will be a valuable tool to address different research topics.

It will allow the isolate, subtype and genotype specific study of functions of all HCV genome regions and proteins using reverse genetics.

Accordingly the developed cell culture systems allow individual patient targeting. This means that when a new potential therapeutic candidate is discovered it is possible to test this particular candidate or combination of candidates on novel HCV isolates grown in culture.

The knowledge of which specific genotype the therapeutic candidate elicits the highest antiviral activity allows an individual treatment of each patient dependent on with which specific genotype the patient is infected. Furthermore, these cell culture systems allow the development of antibodies and vaccines targeting individual patients.

The replication level of a virus can be determined, in other embodiments, using techniques known in the field, and in other embodiments, as exemplified herein. For example, the genome copies can be determined using RT-PCR, and northern blot. To determine the level of a viral protein, one can use techniques including ELISA, immunoprecipitation, immunofluorescence, EIA, RIA, and Western blotting analysis.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture.

In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore, the invention also provides test kits, for screening for new HCV inhibitors, neutralizing and cross neutralizing antibodies, comprising HCV virus components.

A further aspect of the present invention relates to a method for obtaining an isolated nucleic acid molecule encoding a human hepatitis C virus with adaptive mutations, comprising identification of one or more adaptive mutations as described in the above method, incorporation of said one or more adaptive mutations into a nucleic acid molecule encoding a full length human hepatitis C virus, and isolating the nucleic acid molecule encoding a human hepatitis C virus with adaptive mutations.

One embodiment of the present invention relates to an isolated nucleic acid molecule obtained from the above method.

Another embodiment of the present invention relates to an isolated nucleic acid molecule according to the present invention.

EXAMPLES

Example 1

Abstract

Background & Aims

Direct-acting antivirals (DAA) have great potential for hepatitis C virus (HCV) therapy, but efficacy apparently depends on the infecting genotype. Preclinical studies benefit from genotype-specific infectious culture systems. The present inventors aimed at developing HCV recombinants with genotype 1-6 5'UTR-NS5A for testing NS5A and protease inhibitors (PI).

Methods

Recombinants comprising strain-specific 5'UTR-NS5A and 2a(JFH1) NS5B-3'UTR with LSG (F1464L/A1672S/D2929G) mutations were constructed, and adapted in transfected Huh7.5 cells. Additional mutations identified in recovered viruses were incorporated for further adaptation. Concentration-response DAA profiles were determined in high-throughput assays.

Results

Efficient culture-adapted genotype(isolate) 1a(H77), 1a(TN), 3a(S52), 4a(ED43), 5a(SA13), and 6a(HK6a) 5'UTR-NS5A recombinants required no NS5A-domain-I and NS3-protease mutations, thus being ideal for DAA testing. Genotype 1-6 recombinant viruses were concentration-dependently inhibited by lead NS5A inhibitor daclatasvir, confirming genotype-dependent activity, and by lead PIs telaprevir, boceprevir, asunaprevir, simeprevir, vaniprevir, faldaprevir, and MK-5172, all tested for the first time against genotype 4. Compared to 2a(J6/JFH1), 1a(H77 and TN), 5a(SA13) and 6a(HK6a) had similar or better sensitivity, while 3a(S52) was resistant to all PIs. 4a(ED43) was relative resistant to telaprevir and boceprevir, but most sensitive to other PIs. MK-5172, not previously tested against genotypes 3-6, showed exceptional potency against all genotypes.

Conclusions

The LSG mutations in NS3-helicase, NS4A, and NS5B permitted culture development of efficient HCV genotype 1-6 5'UTR-NS5A recombinants. These are the most advanced genotype 3-6 culture systems, and contain for the first time NS3-helicases, and natural NS3-protease and NS5A-domain-I sequences. They allowed head-to-head comparisons of lead NS5A and protease inhibitors, revealing differential efficacy against genotype 1-6 HCV strains.

Introduction

Hepatitis C virus (HCV) is a global health burden, infecting over 130 million people. Chronic hepatitis C frequently leads to liver cirrhosis, end-stage liver disease, and hepatocellular carcinoma. HCV is a member of the Flaviviridae family with a ~9.6-kb positive single-stranded RNA genome consisting of one open reading frame (ORF) flanked by 5' and 3' untranslated regions (UTRs). The ORF is translated into structural (Core, E1, and E2) and nonstructural (p7, NS2, NS3, NS4A, NS4B, NS5A, and NS5B) proteins. The NS3/NS4A protease essential for viral polyprotein processing, the NS5A protein important for replication and assembly, and the NS5B viral RNA polymerase are major targets for novel antivirals.

Six epidemiologically important major HCV genotypes with numerous subtypes (a, b, etc.) exist. The differences within genotypes, subtypes, and isolates/strains at the nucleotide (nt) and amino acid (aa) level are approximately 30%, 20%, and 2-10%, respectively. Genotypes 1, 2, and 3 are the most prevalent worldwide, and account for ~80% of global HCV infections. Genotype 3 accounts for the majority of infections in India, Pakistan and Brazil, and >20% in many European and Asian countries, Canada, Israel, and Australia. Genotypes 4, 5, and 6 represent ~20% of worldwide HCV infections. Genotype 4 is highly prevalent in the Middle East and in many African countries, and is spreading to Western countries. Genotype 5 represents ~40% of cases in South Africa, and is emerging in Europe. Finally, genotype 6 is found predominantly in South East Asia.

Treatment of chronic HCV infection with interferon-alpha and ribavirin (IFN-α/RBV) has severe side effects with host factors and HCV genotype being the major determinants of sustained virological response (SVR), which is achieved only in about half of treated patients. At present, however, it appears that direct-acting antivirals (DAAs) will improve the outcome of HCV therapy. In 2011, NS3/NS4A protease inhibitors (PI) telaprevir and boceprevir were licensed for treatment of chronic genotype 1 infection. Additional DAAs targeting the NS3 protease, NS5A, and NS5B polymerase have reached phase II or III clinical trials, and the first studies that combined different DAAs highlight their potential as future IFN-free treatment regimens.

DAAs were mainly developed and studied in HCV genotype 1-replicon systems. Clinical trials have been primarily performed in patients infected with genotype 1, and there is limited knowledge on efficacy against other major genotypes. The high heterogeneity of HCV may lead to differential efficacy of DAAs against different genotypes or strains. Efficient infectious cell culture systems of all major HCV genotypes would permit preclinical testing of DAAs in a genotype-specific manner with a high-throughput approach. However, full-length cultures only exist for genotypes 1a, 2a, and 2b. In prior studies, the present inventors exploited the replication capacity of the 2a culture strain JFH1 to construct recombinant viruses comprising portions of other HCV genotype strains, including the 5'UTR-NS2, NS3P/NS4A, NS5A or 5'UTR-NS3 protease/NS4A-NS5A. Such systems have permitted genotype-specific studies of novel antivirals. However, several of these chimeric in vitro systems required adaptive mutations in the targeted HCV proteins, which we have found could influence sensitivity to DAAs. Also, systems for key viral enzymes are missing for HCV genotypes 3-6.

The present inventors previously found that F1464L (NS3 helicase), A1672S (NS4A), and D2929G (NS5B) permitted the development of full-length HCV genotype 1 and 2 infectious culture systems [aa (and nt) positions according to genotype 1a strain H77; GenBank accession number AF009606]. The present inventors here used these unique mutations to develop genotype(isolate) 1a(TN and H77), 3a(S52), 4a(ED43), 5a(SA13), and 6a(HK6a) specific 5'UTR-NS5A (5-5A) prototype cultures.

The 5-5A recombinants represent the most advanced infectious culture systems for HCV genotypes 3-6, being the first to include genotype 4 specific NS3/NS4A protease, genotype 3-6 specific NS3 helicases, and genotype 4-6 specific NS4B. Importantly, these recombinants did not require adaptive mutations in the NS3 protease and NS5A-domain-I regions after viral passage. The present inventors demonstrated genotype(isolate)-dependent responses to lead DAA targeting the HCV NS3 protease and NS5A, including DAAs approved for clinical use and those most advanced in clinical trials.

Materials and Methods

Construction of HCV 5'UTR-NS5A Recombinants.

To construct 5'UTR-NS5A recombinants of genotype (isolate) 1a(H77), 3a(S52), and 4a(ED43), NS5B-3'UTR of pCV-H77C, pS52, and pED43 were replaced by the corresponding JFH1 sequence from J6/JFH1-based NS5A recombinants, which contained the junction of isolate-specific NS5A and JFH1 NS5B-3'UTR. For 5a(SA13) and 6a(HK6a) 5'UTR-NS5A recombinants, we used the previously reported sequences of 5'UTR-NS2, NS3 protease and NS4A, and NS5A. The consensus sequences of the NS3 helicase and NS4B of SA13 and HK6a were obtained by RT-PCR and analysis of multiple clones, using plasma pools of experimentally infected chimpanzees. The junction of isolate-specific NS5A and JFH1 NS5B-3'UTR was previously generated, thus, the 5a(SA13) and 6a(HK6a) 5'UTR-NS5A recombinants were constructed by standard cloning procedures. The LSG (F1464L/A1672S/D2979G) and other mutations found in this study were generated by standard cloning procedures. Final plasmid preparations were sequenced covering the T7 promoter and the entire HCV genome (Macrogen).

Analysis of HCV Recombinants in Huh7.5 Cells.

Procedures for the transfection and infection of human hepatoma cell line Huh7.5 have been described previously. The transfected or infected cultures were incubated for ~16 hours, and sub-cultured every 2-3 days; the supernatant was collected, filtered (0.45 μm), and stored at −80° C.

To monitor virus spread in cell cultures, monoclonal anti-Core antibody C7-50 (Enzo Life Sciences) and/or anti-NS5A antibody 9E10 were used for immunostaining for HCV infected cells as described. HCV infectivity titers were determined by FFU assay, using a combination of C7-50 (1/450 dilution) and 9E10 (1/1000 dilution) antibodies. The number of FFU was counted automatically with an ImmunoSpot Series 5 UV Analyzer with customized software (CTL Europe GmbH) or was manually counted with light microscopy. The method for sequence analysis of the ORF of recovered viruses has been described.

DAA Treatment of HCV Recombinant Viruses.

HCV DAAs were purchased from Acme Bioscience and dissolved in dimethyl sulfoxide (Sigma). High throughput treatment assays have been previously established. Concentration-response curves, EC50 values, and 95% confidence interval were calculated in GraphPad Prism 5 as described. Cytotoxicity assays to determine the non-cytotoxic dose range of the anti-HCV drugs were performed.

Results

HCV genotype 2a-derived NS3 helicase, NS4A, and NS5B mutations facilitated the development of 1a, 3a, 4a, 5a, and 6a specific 5'UTR-NS5A culture systems.

The LSG mutations F1464L, A1672S, and D2929G were critical for the development of J6cc, J8cc, and TNcc full-length infectious cell culture systems. Here, the present inventors initially tested whether LSG and additional TNcc-adaptive mutations could adapt another in vivo infectious full-length genotype 1a clone, H77C, for replication in cell culture. H77C with its replicon-derived mutations was able to grow in Huh7 cells, albeit with low infectivity titers and delayed spread kinetics. The present inventors found that after RNA transfections of Huh7.5 cells with H77C containing LSG or LSG plus TNcc-adaptive mutations A1226G/Q1773H/N1927T/Y2981F/F2994S cultures remained negative in HCV-antigen immunostaining assays.

The present inventors next tested H77C 5'UTR-NS5A JFH1-based recombinant, designated 1a(H77)5-5A, as well as variants with either LSG or LSG/A1226G/Q1773H mutations (FIG. 1A and FIG. 3); LSG/A1226G/Q1773H efficiently adapted a 1a(TN)5-5A recombinant (FIG. 3). After two RNA transfections of Huh7.5 cells, 1a(H77)5-5A cultures were HCV negative for 29 and 31 days, respectively. In contrast, a 1a(H77)5-5A_LSG culture showed HCV positive cells from day 4, indicating that LSG could initiate replication of 1a(H77)5-5A; after 36 days of follow-up, however, the virus did not spread. 1a(H77)5-5A_LSG/A1226G/Q1773H (GenBank accession number KF134007) showed 5% HCV-antigen positive cells at day 1, and reached peak infection (≥80% of culture cells infected) at day 8. After passage to naïve Huh7.5 cells, culture supernatant reached HCV infectivity titers of $10^{4.1}$ focus forming units (FFU)/ml. Sequence analysis of the ORF of first-passage virus revealed that the engineered mutations were maintained, and although putative adaptive mutations were observed in the NS3 helicase, no mutations were found in the NS3 protease (spanning nts 3420-3977 and aa 1027-1212) (FIG. 5). Thus, although the LSG mutations could apparently not adapt H77C, it facilitated the development of 5-5A recombinant viruses for genotype 1a TN and H77 strains.

Next, the present inventors used the LSG mutations to develop 5-5A recombinants for other genotype isolates. The present inventors previously demonstrated that 5'UTR-NS3 protease and NS4A-NS5A sequences of 3a(S52), 5'UTR-NS2 and NS5A of 4a(ED43), and 5'UTR-NS2, NS3 protease/NS4A, and NS5A of 5a(SA13) and 6a(HK6a) were functional in JFH1-based recombinants.

However, it remained unknown whether the NS3 helicase domain (spanning nts 3978-5312 and aa 1213-1657) encoded by these strains could support viral replication in cell culture. Here, the present inventors tested 3a(S52), 4a(ED43), 5a(SA13), and 6a(HK6a) specific 5-5A recombinants containing the LSG mutations (FIG. 1A). After RNA transfection of Huh7.5 cells (FIG. 3), HCV positive cells emerged in 3a(S52)5-5A_LSG and 4a(ED43)5-5A_LSG cultures at day 4, and spread to ≥80% of culture cells at day 41 and 50, respectively. The 5a(SA13)5-5A_LSG culture showed 1-5% HCV positive cells at day 1 and reached peak infection at days 7 and 8 in two transfections, whereas the 6a(HK6a)5-5A_LSG culture showed HCV positive cells at day 1 and reached peak infection at day 64. First-passage supernatants had peak infectivity titers of $10^{4.2}$, $10^{3.9}$, $10^{4.7}$, and $10^{3.5}$ FFU/ml for 3a(S52), 4a(ED43), 5a(SA13), and 6a(HK6a) 5-5A_LSG cultures, respectively. Sequence analysis of the ORF of 3a(S52) (FIG. 6), 4a(ED43) (FIG. 7), 5a(SA13) (FIG. 8), and 6a(HK6a) (FIG. 9) 5-5A_LSG cultures revealed that LSG were maintained in all passage viruses, except a partial reversion (50/50 quasispecies) of G at aa 2979 in the 4a(ED43)5-5A_LSG virus; other mutations were observed in these viruses (see below). Thus, we generated HCV genotype 3a, 4a, 5a, and 6a specific 5'UTR-NS5A recombinant viruses by using the LSG mutations, showing for the first time that NS3 helicase of HCV genotypes 3-6 were functional for the complete viral life cycle in Huh7.5 cells.

Development of efficient HCV recombinants with 5'UTR-NS5A of genotype 3a, 4a, 5a, and 6a prototype isolates.

Although LSG could initiate replication of genotype (isolate)-specific 5-5A recombinants, the 3a(S52), 4a(ED43), and 6a(HK6a) 5-5A_LSG viruses required 41, 50, and 64 days, respectively, to spread to most culture cells, and released low HCV infectivity titers ($10^{2.4}$-$10^{2.5}$ FFU/ml) (FIG. 3). The 5a(SA13)5-5A_LSG recombinant had efficient viral spread, but infectivity titers were relatively low ($10^{2.8}$-$10^{3.2}$ FFU/ml) (FIG. 3). The present inventors further optimized these 5-5A recombinants by introducing additional mutations identified in the passaged viruses to generate the most advanced infectious culture systems for HCV genotypes 3-6. Given the existence of full-length H77-S and efficient 5-5A (FIG. 3) and full-length TN culture systems, the present inventors did not further optimize 1a(H77)5-5A_LSG/A1226G/Q1773H, which had efficient viral spread and HCV infectivity titers of $>10^{4.0}$ FFU/mL after first-passage (FIG. 3). The final genotype 3-6 specific 5-5A recombinant viruses did not have mutations in the NS3 protease and NS5A-domain-I (spanning nts 6258-6896 and aa 1973-2185) sequences, thus making them ideal models for studies of protease and NS5A inhibitors.

Efficient 3a(S52) 5'UTR-NS5A Recombinant.

First-passage 3a(S52)5-5A_LSG acquired six 50/50 quasispecies mutations coding for changes at five aa positions, A855A/D and D871D/G (NS2), V1769V/A and H1819H/R/Q (NS4B), and K2276K/E (NS5A) (FIG. 6). In clonal analysis of PCR products covering NS2 and NS4B mutations, the D871G/H1819R combination appeared in 3 of 8 clones, while A855D/V1769A, A855D/H1819R, A855D/H1819Q, H1819Q, and wild-type were each found in 1 clone. We thus engineered D871G/H1819R into 3a(S52)5-5A_LSG; this recombinant showed 1% HCV positive cells on day 1 post transfection and reached peak infection at day 13 with an infectivity titer of $10^{3.3}$ FFU/ml. In contrast, 3a(S52)5-5A_LSG/H1819R was HCV negative until day 4 and had delayed spread (FIG. 3). After first-passage, all engineered mutations were maintained, and no common mutation was found in these two viruses (FIG. 6). The present inventors performed a second-passage of 3a(S52)5-5A_LSG/D871G/H1819R, and identified 50/50 quasispecies at two positions coding for V1612V/E (NS3 helicase) and V2417V/A (NS5A-domain-III) changes (FIG. 6). The present inventors thus introduced these two mutations into 3a(S52)5-5A_LSG/D871G/H1819R (FIG. 1B and FIG. 3). The 3a(S52)5-5A_LSG/D871G/V1612E/H1819R/V2417A recombinant (GenBank accession number KF134008) showed HCV positive cells at day 1, and reached peak infection at day 7 and 11 in two transfections, with peak HCV infectivity titers of $10^{4.0}$ and $10^{3.6}$ FFU/ml, respectively. Sequence analysis of the second-passage viruses ($10^{4.1}$ and $10^{4.3}$ FFU/ml) revealed a single common aa substitution in NS4B (V1769A), but importantly no changes were observed in the NS3 protease and NS5A-domain-I sequences (FIG. 6).

Efficient 4a(ED43) 5'UTR-NS5A Recombinant.

ORF sequence analysis of one first-passage and two independent second-passage virus pools of 4a(ED43)5-5A_LSG revealed complete aa changes A1309P (NS3) and A1786V (NS4B) in all three viruses, as well as four 50/50 quasispecies aa changes, R781R/W (p7), P869P/L (NS2), V1797V/I (NS4B), and V2268V/A (NS5A), in at least two of three viruses. Surprisingly, the engineered G2979 (NS5B)

had reverted to 50/50 quasispecies in first-passage virus and to wild-type sequence only in two second-passage viruses (FIG. 7). Clonal analysis of PCR products spanning the p7 and NS2 mutations, amplified from the first-passage virus, showed that R781W, P869L, and wild-type were found in 7, 2, and 1 clones, respectively. In clonal analysis of NS4B and NS5A mutations, V1797I/V2268A, V1797I, V2268A, and wild-type were found in 4, 2, 3, and 3 clones, respectively. The present inventors thus engineered three sets of mutations, A1309P/A1786V, R781W/A1309P/A1786V, and P869L/A1309P/A1786V, into a 4a(ED43)5-5A_LS genome, and tested viability by transfection of Huh7.5 cells. The 4a(ED43)5-5A_LS/A1309P/A1786V and 4a(ED43)5-5A_LS/P869L/A1309P/A1786V cultures were HCV positive but spread to only 50% of culture cells at day 16. In contrast, 4a(ED43)5-5A_LS/R781W/A1309P/A1786V showed ~1% HCV positive cells at day 1 and spread to ≥80% at day 7 in two independent transfections, with peak infectivity titer of $10^{3.8}$ and $10^{3.2}$ FFU/ml (FIG. 1B and FIG. 3). We also tested these three sets of mutations in the original 4a(ED43)5-5A_LSG recombinant, and found that they only spread to ≤10% cultured cells after 30 days of follow-up.

Thus, 4a(ED43)5-5A_LS/R781W/A1309P/A1786V was most efficient (GenBank accession number KF134009). The present inventors passaged the culture supernatants from two independent transfections and reached titers of $10^{3.2}$ and $10^{3.1}$ FFU/ml in second-passage (FIG. 3); no additional mutations were detected in ORF sequence analysis performed for one of these viruses (FIG. 7). However, after sixth and seventh passages of the 4a (ED43) 5'UTR-NS5A recombinant ED43(5'UTR-NS5A)/JFH1_LS/R781W/A1309P/A1786V (SEQ ID NOs 4 and 10), sequence analysis of the open reading frame of the recovered viruses lead to the identification of additional mutations which further increased efficiency of viral replication of the 4a (ED43) 5'UTR-NS5A recombinant (FIG. 11).

Efficient 5a(SA13) 5'UTR-NS5A Recombinant.

The 5a(SA13)5-5A_LSG viruses from two independent transfections were passaged (FIG. 3) and the ORF sequences of recovered viruses were analyzed (FIG. 8). The virus pool ($10^{5.1}$ FFU/ml) from one second-passage virus contained a dominant aa change S294G (E1) and a complete aa change C1551F (NS3 helicase). We thus engineered these mutations into the 5a(SA13)5-5A_LSG recombinant (FIG. 1B and FIG. 3). Following two independent transfections, 5a(SA13) 5-5A_LSG/S294G/C1551F (GenBank accession number KF134010) showed 5-10% HCV positive cells at day 1, spread to most cells within 3 days, and produced peak infectivity titers of $10^{4.5}$ FFU/ml, being ~30-fold higher than the original 5a(SA13)5-5A_LSG (FIG. 3). In first- and second-passage, peak infectivity titers were ~$10^{4.5}$ and $10^{4.9}$ FFU/ml, respectively (FIG. 3). ORF sequence analysis of one of the second-passage viruses revealed that no additional changes were required (FIG. 8).

Efficient 6a(HK6a) 5'UTR-NS5A Recombinant.

Five mutations were identified in the ORF of first-passage 6a(HK6a)5-5A_LSG, coding for a dominant aa change T387I (E2) and four complete changes S872P (NS2), V1550L (NS3 helicase), L1790M (NS4B), and S2218P (NS5A-low-complexity-sequence-I); in second-passage virus, T387I also became a complete change and no additional mutations were found (FIG. 9). The present inventors thus introduced these five mutations into 6a(HK6a)5-5A_LSG (FIG. 1B and FIG. 3). Following two independent transfections, 6a(HK6a)5-5A_LSG/T387I/S872P/V1550L/L1790M/S2218P (GenBank accession number KF134011) cultures had 1-5% positive cells at day 1 and spread to ≥80% at days 7 and 9, with peak infectivity titers of $10^{3.4}$ and $10^{3.3}$ FFU/ml, respectively. After passages, we sequenced one second-passage virus ($10^{3.8}$ FFU/ml), and found that all engineered mutations were maintained. Mutations were found in E1, NS2, and NS4B; no mutations were found in the NS3 protease and NS5A-domain-I sequences (FIG. 9).

Efficacy of Lead NS3/NS4A Protease Inhibitors and an NS5A Inhibitor Against HCV Recombinants with Genotype 1-6 Specific 5'UTR-NS5A.

Since no mutations appeared in the NS3 protease region in first-passage 5-5A recombinants, these culture viruses could be ideal models for studying the efficacy of PIs in a genotype-specific manner. We thus generated virus stocks from first-passage 1a(H77 and TN) and second-passage 3a(S52), 4a(ED43), 5a(SA13), and 6a(HK6a) 5-5A viruses (FIG. 3) for PI treatment experiments. Additionally, we generated a first-passage stock of 2a J6/JFH1. We confirmed that virus stocks used for treatment were without NS3 protease mutations (FIGS. 5-9). We tested virus sensitivity to the most advanced PIs: telaprevir (VX-950), boceprevir (SCH503034), asunaprevir (BMS-650032), simeprevir (TMC435350), vaniprevir (MK-7009), faldaprevir (BI201335), and MK-5172. As shown in FIG. 2, all genotype recombinant viruses were inhibited by the different PIs in a concentration-dependent manner. The median effective concentration (EC50) representing the efficacy of drugs against the treated viruses was calculated from the concentration-response curves (FIGS. 2, 4 and 10). For a given inhibitor, EC50 fold-differences relative to J6/JFH1 were calculated for each genotype recombinant and used to describe whether a recombinant was more sensitive (fold-difference <1) or resistant (fold-difference >1) than J6/JFH1. EC50s against J6/JFH1 for telaprevir (493 nM), boceprevir (589 nM), simeprevir (91 nM), vaniprevir (88 nM), and asunaprevir (159 nM) were all similar to the EC50s previously observed.

As shown in FIG. 2 and FIG. 4, differences in sensitivity to telaprevir and boceprevir were relatively small for the recombinants of different genotypes. The 3a(S52) and 4a(ED43) 5-5A viruses were the most resistant, being ~4- and ~2-fold more resistant than J6/JFH1 to telaprevir and boceprevir, respectively. In contrast, 6a(HK6a)5-5A was the most sensitive to these two drugs, being ~4-fold more sensitive than J6/JFH1. 1a(TN)5-5A was ~2-3 fold more sensitive, while 1a(H77) and 5a(SA13) 5-5A viruses showed a less than 2-fold difference from J6/JFH1.

Compared to J6/JFH1, 3a(S52)5-5A was ~13-fold more resistant to asunaprevir, while 1a(H77) and 4a(ED43) 5-5A viruses were ~5-fold more sensitive, and 1a(TN), 5a(SA13), and 6a(HK6a) 5-5A viruses were ~2-3 fold more sensitive. For simeprevir, 3a(S52)5-5A was ~27-fold more resistant than J6/JFH1, and the 1a(H77) and 4a(ED43) 5-5A viruses were ~10 more sensitive, whereas the other recombinants showed less than 2-fold differences compared to J6/JFH1. For vaniprevir, 3a(S52)5-5A was ~22-fold more resistant than J6/JFH1, while 4a(ED43)5-5A was ~10-fold more sensitive, and the other 5-5A recombinant viruses were ~3-6 fold more sensitive. For faldaprevir, 3a(S52)5-5A was ~17-fold more resistant than J6/JFH1, while 1a(H77), 4a(ED43), and 5a(SA13) 5-5A viruses were ~12-, 44-, and 10-fold more sensitive, and 1a(TN) and 6a(HK6a) 5-5A viruses were ~4-fold more sensitive. The EC50s of these drugs against 3a(S52)5-5A were close to the EC50s for telaprevir and boceprevir, ranging from 1215 to 2476 nM, indicating similar susceptibility of the 3a(S52)5-5A virus to these PIs.

All recombinant viruses showed the highest sensitivity to MK-5172 compared to other PIs, indicating that MK-5172 was the most potent PI with broad activity against HCV genotypes 1-6. However, the 3a(S52)5-5A virus was ~13-fold less sensitive than J6/JFH1 to MK-5172, while differences in sensitivity of less than 2-fold were found for the remaining 5-5A viruses. Overall, 3a(S52)5-5A was the most resistant virus to the lead candidate PIs tested. This is consistent with our previous observation in the antiviral treatment of NS3/NS4A protease recombinants for selected PIs. Resistance of 3a(S52)5-5A to telaprevir, boceprevir, asunaprevir, simeprevir, vaniprevir, and faldaprevir was >60-fold more than that to MK-5172. Although 4a(ED43) 5-5A virus was resistant to telaprevir and boceprevir, with resistance levels close to the 3a(S52)5-5A virus, it was the most sensitive virus to asunaprevir, simeprevir, vaniprevir, faldaprevir, and MK-5172.

The 5-5A recombinant viruses are also ideal for NS5A inhibitor testing since they do not appear to require adaptive mutations in NS5A-domain-I (FIGS. 5-9). Of all tested DAAs, the NS5A-domain-I directed inhibitor daclatasvir (BMS-790052) had the highest potency against all viral genotypes, being ~30 to 100-fold more efficient than the most potent PI, MK-5172. Among the different viruses, 3a(S52)5-5A was the most resistant, being ~6-fold more resistant than J6/JFH1, while 4a(ED43)5-5A was the most sensitive virus, being ~5-fold more sensitive than J6/JFH1. The other genotypes showed less than a 3-fold difference in sensitivity compared to J6/JFH1. The EC50s of daclatasvir against 5-5A recombinants and J6/JFH1 were similar to those previously observed for respective genotype(isolate) NS5A recombinants.

Discussion

In this study, the present inventors developed the most advanced infectious cell culture systems to date for genotypes 3-6 of HCV, representing 4 of the 6 major variants of this important human pathogen. The systems contained genotype-specific 3a, 4a, 5a, and 6a sequences from 5'UTR through NS5A, with only NS5B and the 3'UTR from JFH1, and thus were termed '5-5A recombinants'. Development of the 5-5A viruses was aided by previously identified LSG mutations. All recombinant viruses maintained the original patient NS3 protease and NS5A-domain-I sequences, thus representing an ideal panel of genotype viruses for testing NS3 protease and NS5A inhibitors; this study includes the first infectious HCV cell culture recombinant expressing genotype 4 NS3/NS4A protease. We demonstrated concentration-dependent inhibition and genotype-specific activity profiles for lead HCV PIs for genotype 1-6 recombinant viruses in the context of complete viral life cycle. The 3a(S52) virus was most resistant to all PIs, while 4a(ED43) was highly resistant to telaprevir and boceprevir, but was most sensitive to asunaprevir, simeprevir, vaniprevir, faldaprevir, and MK-5172. MK-5172 had the highest efficacy against all genotype recombinants.

The present inventors previously identified and demonstrated the critical role of the 'LSG mutations' (F1464L/ A1672S/D2979G) in the development of HCV full-length culture systems J6cc(2a), J8cc(2b), and TNcc(1a), as well as 1a(TN)5-5A recombinant. In this study, the LSG mutations could initiate replication of 1a(H77), 3a(S52), 4a(ED43), 5a(SA13), and 6a(HK6a) 5-5A recombinants, further demonstrating their cross-genotype effects. Adaptation of 5-5A recombinants has proven an efficient approach for development of HCV full-length systems, as mutations identified from LSG-adapted TN 5-5A recombinant viruses permitted the development of TNcc full-length cultures. Thus, in future studies it will be of great relevance to test mutations identified in the 5-5A recombinants (FIGS. 5-9) in respective full-length genomes to explore their potential in developing full-length culture systems for these important major HCV genotypes.

Efficient 5-5A culture systems for 3a(S52), 4a(ED43), 5a(SA13), and 6a(HK6a) also demonstrated for the first time that the NS3 helicase of these isolates was functional in Huh7.5 cells. The NS3 helicase is critical for HCV RNA replication and could be a target of antivirals. Within the NS3 helicase, all 5-5A recombinants contained the engineered mutation F1464L ("L" of LSG). Recombinant specific helicase mutations were A1226G for 1a(H77) and 1a(TN), V1612E for 3a(S52), A1309P for 4a(ED43), C1551F for 5a(SA13), and V1550L for 6a(HK6a). Importantly, no additional mutations were required in this region after viral passage, with the exception of a non-dominant mutation (S1368S/P) in the 1a(H77) virus (FIGS. 5-9), indicating genetic stability of the helicase sequence in these recombinants. Screening of potentially effective HCV helicase inhibitors primarily relied on the assessment of helicase catalytic activity in RNA strand separation and ATP hydrolysis, as well as on the DNA binding assays, but no viral assays were established. To date, only a few helicase inhibitors have been reported to decrease HCV RNA replication efficiency in cells, and none has been reported in clinical trials. Therefore, the developed 5-5A culture systems will permit future screening or testing of the effect of helicase inhibitors in the context of complete viral life cycle for the major HCV genotypes.

The 4a(ED43), 5a(SA13), and 6a(HK6a) 5-5A recombinants are the first infectious culture systems with NS4B (spanning nts 5475-6257 and aa 1712-1972) of genotypes 4, 5, and 6, They therefore represent a valuable tool for development of pan-genotypic NS4B inhibitors, since although there is no clinical data available, recently, NS4B has been suggested as a potential target for DAAs.

Importantly, none of the 5-5A recombinants developed in this study required mutations in the NS3 protease and NS5A-domain-I (the target of daclatasvir) to efficiently grow in cell culture, thus, representing wild-type viral sequences of these regions. These properties permitted us to assess the genotype-specific profiles for either protease or NS5A inhibitors that are most likely reflecting relevant clinical differences in drug sensitivity, without being possibly misled by the influence of cell culture adaptive mutations in the drug targets. These systems will thus also be ideal for future studies of combinations of protease and NS5A inhibitors. In our treatment studies, the EC50s of telaprevir, boceprevir, simeprevir, and daclatasvir against 1a(TN)5-5A were similar to previously reported values for TNcc full-length virus. In addition, the fold-difference of EC50s of telaprevir, boceprevir, simeprevir, and vaniprevir against 3a(S52)5-5A, the most resistant virus, relative to J6/JFH1 was similar to that against a previously developed 3a(S52) NS3/NS4A protease recombinant (FIG. 4). The EC50s of asunaprevir and daclatasvir against 1a(TN), 1a(H77), and 3a(S52) 5-5A recombinants relative to J6/JFH1 were also similar to those previously observed for respective genotype(isolate) semi-FL recombinants. These similar results across various treatment studies validate in vitro antiviral studies in these different culture systems and the reproducibility of treatment assays. Our results also suggest that the inclusion of NS5B-3'UTR or more sequences from JFH1 and of most adaptive mutations engineered do not interfere with antiviral treatment studies. Thus, the 5-5A recombinants may effectively recapitulate the infection cycle of viral genotypes, making them useful as models for testing drugs targeting 5'UTR to NS5A regions and for studying viral escape and resistance in a genotype-specific manner.

As severe adverse events of IFN-based therapies lead to an approximately 10% discontinuation rate, and the outcome is suboptimal, there is an urgent need for the development of an IFN-free treatment regimen consisting of DAAs targeting different viral proteins. Clinical studies exploring IFN-free regimens with DAAs tested in this study, such as combination of asunaprevir and daclatasvir, have demonstrated that these drugs can improve SVR rates in patients with genotype 1 infections. In addition preclinical development of DAAs was primarily based on genotype 1 replicons, thus, there is very limited knowledge on antiviral efficacy of DAAs against HCV genotype 3-6 infections. Our experimental data on the efficacy of leading PIs against the most advanced culture systems of HCV genotypes 3a, 4a, 5a, and 6a will contribute to treatment guidelines for patients infected with genotypes 3-6. Notably, MK-5172 showed the highest, but also differential efficiency, against infections of all major viral genotypes (FIG. 2 and FIG. 4). It was previously shown that MK-5172 had activity against genotype 1 and 2 replicons and a high barrier to resistance, but this potent drug was not previously tested against genotype 3-6 viruses.

The 3a(S52)5-5A virus appeared to be the most resistant virus for the tested DAAs (FIG. 2 and FIG. 4). This observation is in line with our previous treatment data, which showed that the J6/JFH1-based 3a(S52) NS3/NS4A recombinant was more resistant than corresponding 2a(J6/JFH1), 5a(SA13), and 6a(HK6a) viruses to telaprevir, boceprevir, simeprevir, and vaniprevir. High resistance of genotype 3a recombinants to DAAs may reflect the resistance characteristics in clinical settings. Genotype 3 patients have limited benefit from telaprevir monotherapy, although a high response rate could be achieved in IFN-α/RBV-based treatment regimens. Here the present inventors showed that MK-5172 and daclatasvir were 60 to 2250-fold more efficient in inhibiting the 3a(S52)5-5A virus compared to the second most efficient protease inhibitor, boceprevir (FIG. 4). These results may facilitate future design of treatment regimens for genotype 3a infected patients.

Limited clinical trials have been performed for genotypes 4, 5, and 6, although these genotypes represent ~20% of all HCV cases worldwide. A few studies with a small number of patients have shown that both genotype 5 and 6 patients achieved SVR rate similar to genotypes 2 and 3, using a longer course of IFN-α/RBV-based treatment; SVR rates for chronic genotype 4 patients were less than 50%. Addition of DAAs to the standard of care or DAA combination therapy may improve treatment outcome for these genotype patients. However, until recently, the efficacy of DAAs against genotype 4a viruses could not readily be tested as there had been no success in generating genotype 4 NS3/NS4A protease culture systems. A 4a(ED43) replicon was recently reported, but with limited treatment data. Infectious genotype 4a protease cell culture systems have not been available until now, as a J6-JFH1 recombinant Jc1 expressing 4a(ED43) NS3/NS4A protease reported previously was not able to generate viruses that could be passaged. The 4a(ED43)5-5A recombinant developed in our study was infectious and efficient in passage, thus permitting for the first time the evaluation of the efficacy of PIs against this important genotype in a high-throughput manner.

Interestingly, 4a(ED43) was resistant to telaprevir and boceprevir at the level of 3a(S52)5-5A virus, but was the most sensitive virus to the PIs simeprevir, vaniprevir, asunapreivr, faldaprevir, and MK-5172, as well as NS5A inhibitor daclatasvir (FIG. 2 and FIG. 4). These findings will contribute to future clinical DAAs guidelines for genotype 4 patients.

In summary, the present inventors have developed the most advanced genotype-specific infectious culture systems for HCV genotypes 3, 4, 5, and 6. We used these systems to demonstrate concentration-dependent and genotype-specific viral responses to the most advanced PIs and NS5A inhibitor. The efficient 5-5A infectious culture systems, which include genotype-specific 5'UTR, Core, E1, E2, p7, NS2, NS3, NS4A, NS4B, and NS5A, have great potential for further functional and treatment studies that will directly contribute to HCV basic research and development of DAAs, thus facilitating personalized IFN-free HCV therapy.

The invention claimed is:

1. An isolated nucleic acid molecule, which encodes a human hepatitis C virus, wherein the hepatitis C virus comprises:
   a 5'UTR-NS5A region derived from genotype 4a strain ED43, wherein the 5'UTR-NS5A region comprises a 5'UTR, structural proteins Core, E1 and E2, and non-structural proteins p7, NS2, NS3, NS4A, NS4B and NS5A;
   a nonstructural protein NS5B; and
   a 3'UTR from strain JFH1;
   further comprising the mutations F1464L in NS3 and A1672S in NS4A according to the H77 sequence as set forth by GenBank accession number AF009606; and
   further comprising adaptive mutations R781W, A1309P and A1786V according to the H77 sequence as set forth by GenBank accession number AF009606.

2. The isolated nucleic acid molecule according to claim 1, comprising a nucleic acid sequence according to SEQ ID NO: 4; GenBank accession number KF134009.

3. The isolated nucleic acid molecule according to claim 1, further comprising one or more of the adaptive mutations selected from the group consisting of V345A, T534S, Y848H, H900R, A2348D, S2356A and S2380F.

4. The isolated nucleic acid molecule according to claim 1, comprising a nucleic acid sequence according to SEQ ID NO: 13.

5. A method for producing a cell, which replicates human hepatitis C virus and produces a virus particle comprising:
   (i) introducing a nucleic acid molecule into a cell, wherein said nucleic acid molecule is selected from the nucleic acids molecule of claim 1.

6. The method of claim 5, further comprising culturing the cell to produce the human hepatitis C virus particle.

7. The method of claim 6, further comprising infecting other cells with the produced human hepatitis C virus particle.

8. A method of screening for an anti-hepatitis C virus substance, comprising: a) culturing a cell comprising the nucleic acid molecule of claim 1 together with a hepatitis C virus permissive cell, b) contacting the cell with a candidate anti-hepatitis C substance, and c) measuring the level of replicating RNA or virus particles in the resulting culture and comparing the level to that of a control.

9. The method according to claim 8, wherein the substance is a protease inhibitor, a NS5A inhibitor, a drug targeting sequence or a protein incorporated in 5'UTR-NS5A.

* * * * *

SEQUENCE LISTING

<160> NUMBER OF SEQ ID NOS: 14

<210> SEQ ID NO 1
<211> LENGTH: 9613
<212> TYPE: DNA
<213> ORGANISM: Hepatitis C virus

<400> SEQUENCE: 1

```
gccagccccc tgatgggggc gacactccac catgaatcac tcccctgtga ggaactactg      60
tcttcacgca gaaagcgtct agccatggcg ttagtatgag tgtcgtgcag cctccaggac     120 ccccctccc gggagagcca tagtggtctg cggaaccggt gagtacaccg gaattgccag     180
gacgaccggg tcctttcttg gataaacccg ctcaatgcct ggagatttgg gcgtgccccc     240
gcaagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gtcgcccaca ggacgtcaag ttcccgggtg     420
gcggtcagat cgttggtgga gtttacttgt tgccgcgcag gggccctaga ttgggtgtgc     480
gcgcgacgag gaagacttcc gagcggtcgc aacctcgagg tagacgtcag cctatcccca     540
```

```
aggcacgtcg gcccgagggc aggacctggg ctcagcccgg gtaccttgg ccccctctatg    600 gcaatgaggg ttgcgggtgg gcgggatggc tcctgtctcc ccgtggctct cggcctagct    660
ggggccccac agaccccggg cgtaggtcgc gcaatttggg taaggtcatc gatacccttac   720 cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tcccaggc gccactggac gacgcaagac tgcaattgtt      1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040 cccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtgcgg cgttgttctt gtcgggttaa   2820
tggcgctgac tctgtcgcca tattacaagc gctatatcag ctggtgcatg tggtggcttc   2880
```

| | |
|---|---|
| agtattttct gaccagagta gaagcgcaac tgcacgtgtg ggttccccccc ctcaacgtcc | 2940 |
| gggggggggcg cgatgccgtc atcttactca tgtgtgtagt acacccgacc ctggtatttg | 3000 |
| acatcaccaa actactcctg ccatcttcg acccctttg gattcttcaa gccagtttgc | 3060 |
| ttaaagtccc ctacttcgtg cgcgttcaag gccttctccg gatctgcgcg ctagcgcgga | 3120 |
| agatagccgg aggtcattac gtgcaaatgg ccatcatcaa gttaggggcg cttactggca | 3180 |
| cctatgtgta taaccatctc accctcttc gagactgggc gcacaacggc ctgcgagatc | 3240 |
| tggccgtggc tgtggaacca gtcgtcttct cccgaatgga gaccaagctc atcacgtggg | 3300 |
| gggcagatac cgccgcgtgc ggtgacatca tcaacggctt gcccgtctct gcccgtaggg | 3360 |
| gccaggagat actgcttggg ccagccgacg gaatggtctc caaggggtgg aggttgctgg | 3420 |
| cgcccatcac ggcgtacgcc cagcagacga gaggcctcct agggtgtata atcaccagcc | 3480 |
| tgactggccg ggacaaaaac caagtggagg gtgaggtcca gatcgtgtca actgctaccc | 3540 |
| aaaccttcct ggcaacgtgc atcaatgggg tatgctggac tgtctaccac ggggccggaa | 3600 |
| cgaggaccat cgcatcaccc aagggtcctg tcatccagat gtataccaat gtggaccaag | 3660 |
| accttgtggg ctggcccgct cctcaaggtt cccgctcatt gacaccctgt acctgcggct | 3720 |
| cctcggacct ttacctggtc acgaggcacg ccgatgtcat tcccgtgcgc cggcgaggtg | 3780 |
| atagcagggg tagcctgctt tcgccccggc ccatttccta cttgaaaggc tcctcggggg | 3840 |
| gtccgctgtt gtgccccgcg ggacacgccg tgggcctatt cagggccgcg gtgtgcaccc | 3900 |
| gtggagtggc taaagcggtg gactttatcc ctgtggagaa cctagggaca accatgagat | 3960 |
| ccccggtgtt cacggacaac tcctctccac cagcagtgcc ccagagcttc caggtgggcc | 4020 |
| acctgcatgc tcccaccggc agcggtaaga gcaccaaggt cccggctgcg tacgcagccc | 4080 |
| agggctacaa ggtgttggtg ctcaacccct ctgttgctgc aacgctgggc tttggtgctt | 4140 |
| acatgtccaa ggcccatggg gttgatccta atatcaggac cggggtgaga acaattacca | 4200 |
| ctggcagccc catcacgtac tccacctacg gcaagttcct tgccgacggc gggtgctcag | 4260 |
| gaggtgctta tgacataata atttgtgacg agtgccactc cacggatgcc acatccatct | 4320 |
| tgggcatcgg cactgtcctt gaccaagcag agactgcggg ggcgagactg gttgtgctcg | 4380 |
| ccactgctac ccctccgggc tccgtcactg tgtcccatcc taacatcgag gaggttgctc | 4440 |
| tgtccaccac cggagagatc ccctttttacg gcaaggctat cccctcgag gtgatcaagg | 4500 |
| ggggaagaca tctcatcttc tgccactcaa agaagaagtg cgacgagctc gccgcgaagc | 4560 |
| tggtcgcatt gggcatcaat gccgtggcct actaccgcgg tcttgacgtg tctgtcatcc | 4620 |
| cgaccagcgg cgatgttgtc gtcgtgtcga ccgatgctct catgactggc tttaccggcg | 4680 |
| acttcgactc tgtgatagac tgcaacacgt gtgtcactca gacagtcgat ctcagccttg | 4740 |
| acctacctt taccattgag acaaccacgc tcccccagga tgctgtctcc aggactcaac | 4800 |
| gccggggcag gactggcagg gggaagccag gcatctatag atttgtggca ccgggggagc | 4860 |
| gcccctccgg catgttcgac tcgtccgtcc tctgtgagtg ctatgacgcg ggctgtgctt | 4920 |
| ggtatgagct cacgcccgcc gagactacag ttaggctacg agcgtacatg aacaccccgg | 4980 |
| ggcttcccgt gtgccaggac catcttgaat tttgggaggg cgtctttacg gcctcactc | 5040 |
| atatagatgc ccacttttta tcccagacaa agcagagtgg ggagaacttt ccttacctgg | 5100 |
| tagcgtacca agccaccgtg tgcgctaggg ctcaagcccc tccccatcg tgggaccaga | 5160 |
| tgtggaagtg tttgatccgc cttaaaccca ccctccatgg gccaacaccc ctgctataca | 5220 |
| gactgggcgc tgttcagaat gaagtcaccc tgacgcaccc aatcaccaaa tacatcatga | 5280 |

```
catgcatgtc ggccgacctg gaggtcgtca cgagcacctg ggtgctcgtt ggcggcgtcc    5340
tggctgctct ggcctcgtat tgcctgtcaa caggctgcgt ggtcatagtg ggcaggatcg    5400
tcttgtccgg gaagccggca attatacctg acagggaggt tctctaccag gagttcgatg    5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt ttgggcgaag cacatgtgga    5640
atttcatcag tgggatacac tacttggcgg gcctgtcaac gctgctggt aaccccgcca     5700 ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ctgcctttgt gggtgctggc ctagctgcgc cgccatcgg cagcgttgga ctggggaagg     5880
tcctcgtgga cattcttgca gggtatggcg cgggcgtggc gggagctctt gtagcattca    5940
agatcatgag cggtgaggtc ccctccacgag gaacctggt caatctgctg cccgccatcc    6000
tctcgcctgg agcccttgta gtcggtgtgg tctgcgcagc aatactgcgc cggcacgttg    6060
gcccgggcga gggggcagtg caatggatga accggctaat agccttcgcc tcccggggga    6120
accatgtttc ccccacgcac tacgtgccgg agagcgatgc agccgcccgc gtcactgcca    6180
tactcagcag cctcactgta acccagctcc tgaggcgact gcatcagtgg ataagctcgg    6240
agtgtaccac tccatgctcc ggttcctggc taagggacat ctgggactgg atatgcgagg    6300
tgctgagcga ctttaagacc tggctgaaag ccaagctcat gccacaactg cctgggattc    6360
cctttgtgtc ctgccagcgc gggtatagg gggtctggcg aggagacggc attatgcaca    6420
ctcgctgcca ctgtggagct gagatcactg gacatgtcaa aaacgggacg atgaggatcg    6480
tcggtcctag gacctgcagg aacatgtgga gtgggacgtt ccccattaac gcctacacca    6540
cgggcccctg tactcccctt cctgcgccga actataagtt cgcgctgtgg agggtgtctg    6600
cagaggaata cgtggagata aggcgggtgg gggacttcca ctacgtatcg ggtatgacta    6660
ctgacaatct taaatgcccg tgccagatcc catcgcccga atttttcaca gaattggacg    6720
gggtgcgcct acacaggttt gcgccccctt gcaagccctt gctgcgggag gaggtatcat    6780
tcagagtagg actccacgag tacccggtgg ggtcgcaatt accttgcgag cccgaaccgg    6840
acgtagccgt gttgacgtcc atgctcactg atccctccca tataacagca gaggcggccg    6900
ggagaaggtt ggcgagaggg tcacccccctt ctatggccag ctcctcggct agccagctgt    6960
ccgctccatc tctcaaggca acttgcaccg ccaaccatga ctcccctgac gccgagctca    7020
tagaggctaa cctcctgtgg aggcaggaga tgggcggcaa catcaccagg gttgagtcag    7080
agaacaaagt ggtgattctg gactccttcg atccgcttgt ggcagaggag gatgagcggg    7140
aggtctccgt acctgcagaa attctgcgga gtctcggag attcgcccgg gccctgcccg     7200
tctgggcgcg gccggactac aaccccccgc tagtagagac gtggaaaaag cctgactacg    7260
aaccacctgt ggtccatggc tgcccgctac cacctccacg gtccctcct gtgcctccgc     7320 ctcggaaaaa gcgtacggtg gtcctcaccg aatcaaccct atctactgcc ttggccgagc    7380
ttgccaccaa aagtttttggc agctcctcaa cttccggcat tacgggcgac aatacgacaa    7440
catcctctga gccgcccct tctggctgcc ccccgactc cgacgttgag tcctattctt      7500
ccatgccccc cctggagggg gagcctgggg atccggatct cagcgacggg tcatggtcga    7560
cggtcagtag tggggccgac acggaagatg tcgtgtgctg ctccatgtca tactcctgga    7620
```

-continued

```
ccggggctct aataactccc tgtagccccg aagaggaaaa gttgccaatc aacccttttga    7680 gtaactcgct gttgcgatac cataacaagg tgtactgtac aacatcaaag agcgcctcac    7740
```


```
ccggggctct aataactccc tgtagccccg aagaggaaaa gttgccaatc aacccttttga    7680
gtaactcgct gttgcgatac cataacaagg tgtactgtac aacatcaaag agcgcctcac    7740
agagggctaa aaaggtaact tttgacagga cgcaagtgct cgacgcccat tatgactcag    7800
tcttaaagga catcaagcta gcggcttcca aggtcagcgc aaggctcctc accttggagg    7860
aggcgtgcca gttgactcca ccccattctg caagatccaa gtatggattc ggggccaagg    7920
aggtccgcag cttgtccggg agggccgtta ccacatcaa gtccgtgtgg aaggacctcc    7980
tggaagaccc acaaacacca attcccacaa ccatcatggc caaaaatgag gtgttctgcg    8040
tggaccccgc caaggggggt aagaaaccag ctcgcctcat cgtttaccct gacctcggcg    8100
tccgggtctg cgagaaaatg gccctctatg acattacaca aaagcttcct caggcggtaa    8160
tgggagcttc ctatggcttc cagtactccc ctgcccaacg ggtggagtat ctcttgaaag    8220
catgggcgga aaagaaggac cccatgggtt tttcgtatga tacccgatgc ttcgactcaa    8280
ccgtcactga gagagacatc aggaccgagg agtccatata ccaggcctgc tccctgcccg    8340
aggaggcccg cactgccata cactcgctga ctgagagact ttacgtagga gggcccatgt    8400
tcaacagcaa gggtcaaacc tgcggttaca acgttgccg cgccagcggg gtgctaacca    8460
ctagcatggg taacaccatc acatgctatg tgaaagccct agcggcctgc aaggctgcgg    8520
ggatagttgc gcccacaatg ctggtatgcg gcgatgacct agtagtcatc tcagaaagcc    8580
aggggactga ggaggacgag cggaacctga gagccttcac ggaggccatg accaggtact    8640
ctgcccctcc tggtgatccc cccagaccgg aatatgacct ggagctaata acatcctgtt    8700
cctcaaatgt gtctgtggcg ttgggcccgc ggggccgccg cagatactac ctgaccagag    8760
acccaaccac tccactcgcc cgggctgcct gggaaacagt tagacactcc cctatcaatt    8820
catggctggg aaacatcatc cagtatgctc aaccatatg ggttcgcatg gtcctaatga    8880
cacacttctt ctccattctc atggtccaag acaccctgga ccagaacctc aactttgaga    8940
tgtatggatc agtatactcc gtgaatcctt ggaccttcc agccataatt gagaggttac    9000
acgggcttga cgcctttttct atgcacacat actctcacca cgaactgacg cgggtggctt    9060
cagccctcag aaaacttggg gcgccacccc tcagggtgtg gaagagtcgg gctcgcgcag    9120
tcagggcgtc cctcatctcc cgtggaggga agcggccgt ttgcggccga tatctcttca    9180
attgggcggt gaagaccaag ctcaaactca ctccattgcc ggaggcgcgc ctactggact    9240
tatccagttg gttcaccgtc ggcgccggcg ggggcggcat ttttcacagc gtgtcgcgcg    9300
cccgaccccg ctcattactc ttcggcctac tcctactttt cgtaggggta ggcctcttcc    9360
tactccccgc tcggtagagc ggcacacact aggtacactc catagctaac tgttccttttt    9420
ttttttttttt tttttttttt ttttttttttt tttttttttc tttttttttt tttccctct    9480
ttcttcccttt ctcatcttat tctactttct ttcttggtgg ctccatctta gccctagtca    9540
cggctagctg tgaaaggtcc gtgagccgca tgactgcaga gagtgccgta actggtctct    9600
ctgcagatca tgt                                                        9613
```

<210> SEQ ID NO 2
<211> LENGTH: 9613
<212> TYPE: DNA
<213> ORGANISM: Hepatitis C virus

<400> SEQUENCE: 2

```
gccagccccc tgatggggc gacactccac catgaatcac tcccctgtga ggaactactg      60
tcttcacgca gaaagcgtct agccatggcg ttagtatgag tgtcgtgcag cctccaggac    120
```

```
cccccctccc gggagagcca tagtggtctg cggaaccggt gagtacaccg gaattgccag      180
gacgaccggg tcctttcttg gatcaacccg ctcaatgcct ggagatttgg gcgtgccccc      240
gcaagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaacgt aacaccaacc gtcgcccaca ggacgtcaag ttcccgggtg      420
gcggtcagat cgttggtgga gtttacttgt tgccgcgcag gggccctaga ttgggtgtgc      480
gcgcgacgag gaagacttcc gagcggtcgc aacctcgagg tagacgtcag cctatcccca      540
aggcgcgtcg gcccgagggc aggacctggg ctcagcccgg gtacccttgg ccctctatg      600 gcaatgaggg ttgcgggtgg gcgggatggc tcctgtctcc ccgtggctct cggcctagct      660
ggggccccac ggaccccggg cgtaggtcgc gcaatttggg taaggtcatc gatacccta      720 cgtgcggctt cgccgacctc atggggtaca taccgctcgt cggcgcccct cttggaggcg      780
ctgccagggc cctggcgcat ggcgtccggg ttttggaaga cggcgtgaac tatgcaacag      840
ggaaccttcc tggttgctct ttctctattt tccttctggc cctgctctct tgtctgactg      900
gacccgcttc agcctaccaa gtgcgcaact ccacggggct ttaccatgtc accaatgatt      960
gccccaactc gagcattgtg ttcgaggcgg ctgatgccat cctgcacact ccggggtgtg     1020
tcccttgcgt acgcgagggt aacgcctcga ggtgttgggt ggcggtaacc cccacggtgg     1080
ccaccaggga tggcaaactc cccacaacgc agcttcgacg tcacatcgat ctgcttgtcg     1140
ggagcgccac cctctgctcg gcccttacg tggggacct gtgcgggtct gtctttcttg      1200
ttggtcaact gttcaccttc tctcccaggc gccactggac gacgcaagat tgcaattgtt     1260
ctatctaccc cggccatatt tcaggtcacc gtatggcatg ggatatgatg atgaactggt     1320
cccctacggc ggcgttgttg gtagctcagc tgctccggat cccacaagcc atcctggaca     1380
tgatcgctgg tgctcactgg ggagtcctgg cgggcatggc gtattctccc atggtgggga     1440
actgggcgaa ggttctggta gtgctgctgc tatttgccgg cgtcgacgcg gaaacctacg     1500
tcaccggggg aagtgccgcc cgtactacgg ctggacttgc tagtcttttc tcaccaggcg     1560
ccaagcagaa catccagctg gtcaacacca acggcagttg gcacatcaat agcacggcct     1620
tgaactgcaa tgacagcctc aacaccggct ggatagcagg acttttctat caccacaaat     1680
tcaactcttc gggctgttcc gagaggttag ccagctgccg acccttacc gattttgccc      1740 agggctgggg ccctatcagt cacgccgacg gaagtggccc cgaccaacgc ccctactgct     1800
ggcactaccc tccaaaacct tgtggtattg tgcccgcaaa gagcgtgtgt ggcccggtat     1860
attgtttcac tcccagtccc gtggtggtgg gaacgaccga caggtcgggc gcgcctacct     1920
acagctgggg tgcaaatgac acggacgtct tcgtccttaa caacaccagg ccaccgctgg     1980
gcaattggtt cggttgcacc tggatgaact caactggatt caccaaagtg tgcggagcgc     2040 cccttgcgt catcggaggg gtgggcaaca acaccttgcg ctgccccact gattgtttcc      2100
gcaagcatcc ggaagccaca tactctcggt gcggctccgg tcctggatt acgcccaggt      2160 gcctggtcga ctacccgtat aggctttggc attatccttg taccatcaac tacaccgtgt     2220
ttaaagtcag gatgtacgtg ggaggggtcg agcacaggct ggaagctgcc tgcaactgga     2280
cgcggggcga ccgttgtaat ctggatgaca gggacaggtc cgagctcagc ccgctgctgc     2340
tgtccactac gcagtggcag gtcctcccgt gttccttcac gacccctgcca gccttgtcca     2400 ccggcctcat ccacctccac caaaacatcg tggacgtgca atacttgtac ggggtgggat     2460
```

```
caagcatcgc gtcctgggcc atcaagtggg aatacgtcgt tctcttgttc cttctgcttg    2520
cagacgcgcg cgtctgctcc tgcttgtgga tgatgttact catatcccaa gtggaggcgg    2580
ctttggagaa cctcgtagta ctcaatgcag catccctggc cgggacacac ggtcttgtat    2640
ccttcctcgt gttcttctgc tttgcatggt atctgaaggg taagtgggtg cccggagcgg    2700
tctacgccct ctacgggatg tggcctctcc tcttgctcct gttagcgttg ccccagcggg    2760
catacgcact ggacacggag gtggccgcgt cgtgtggcgg cgttgttctt gtcgggttaa    2820
tggcgctgac tctgtcacca tattacaagc gctatatcag ctggtgcttg tggtggcttc    2880
agtatttcct gaccagaata gaagcgcaac tgcacgtgtg gattcccoct ctcaacgtcc    2940 gggggggggcg cgatgccgtc atcttactca tgtgtgttgt gcacccggct ctggtatttg    3000
acatcaccaa gctactgctg gctgccttcg ggccccttg gattcttcaa gccagtttgc    3060
ttaaggtacc ctacttcgtg cgcgttcaag gccttctccg gatctgcgcg ctagcgcgga    3120
agatggctgg aggccattac gtgcaaatgc ccatcatcaa gttaggggcg cttactggca    3180
cttatgttta caaccatctc accccccttc gggactgggc gcacaacggc ctgcgagatc    3240
tggccgtggc tgtggagcca gtcgtcttct cccgaatgga gaccaagctt atcacctggg    3300
gggcagacac cgccgcgtgc ggtgacatca tcaacggctt gccegtctcc gcccggaggg    3360 gccgggagat actgctcggg ccagccgatg gaatggtctc caaggggtgg agattgctgg    3420
cgcccatcac ggcgtacgcc cagcaaacga ggggcctcct agggtgtata atcaccagtc    3480
tgaccggccg ggacaaaaac caagtggagg gtgagatcca gattgtgtca actgctgccc    3540
aaaccttcct ggcaacgtgc atcaacgggg tttgctggac cgtctaccac ggggccggaa    3600
cgaggaccat cgcatcaccc aagggtccgg ttatccaaat gtataccaat gtggacaaag    3660
accttgtggg ctggcccgct cctcaaggtg cccgctcact gacaccctgt acctgcggct    3720
cctcggacct ttacctggtc acgaggcacg ccgatgtcat tcccgtgcgc cggcggggtg    3780
atagcagggg cagcctgctt tcgccccggc ccatttccta cttgaaaggc tcctcggggg    3840
gtccgctgct gtgccccgcg ggacacgccg taggcttatt cagggccgcg gtgtgcaccc    3900
gtggagtggc taaggcggtg gacttcatcc ctgtggagaa cctagagaca accatgaggt    3960
ccccggtgtt cacggacaac tcctctccac cagcagtgcc ccagagcttc caggtgggcc    4020
acctgcatgc tcccaccggc agcggcaaaa gcaccaaggt cccggctgca tacgcagctc    4080
agggctataa ggtgctagtg ctcaacccct ctgtcgctgc aacactgggc tttggtgctt    4140
acatgtccaa ggcccatggg gtcgatccta atatcaggac cggggtgaga acaattacca    4200
ctggcagccc catcacgtac tccacctacg gcaagttcct tgccgacggc gggtgttcag    4260
ggggtgctta tgacataata atttgtgacg agtgccactc cacggatgcc acatccatct    4320
tgggcatcgg caccgttctt gaccaagcag agaccgcggg ggcgagactg gttgtgctcg    4380
ccaccgctac ccctcggggc tccatcaccg tgccccatcc taacatcgag gaggttgctc    4440
tgtccactac cggagagatc cctttttacg gcaaggctat cccectcgag gcgatcaagg    4500 gggggagaca tctcatcttc tgtcactcaa agaagaagtg cgacgagctc gccgcaaagc    4560
tggtcgcatt gggcatcaat gccgtggcct actaccgcgg tcttgacgtg tctgtcatcc    4620
caaccagcgg cgatgttgtc gtcgtggcga ccgatgctct tatgactggc tataccggcg    4680
actttgactc ggtgatagac tgcaacacgt gtgtcaccca gacagtcgac ctcagccttg    4740
accctacctt caccattgag acgaccacgc tcccccagga cgctgtctcc cgcacacaac    4800
gccggggcag gactggcagg gggaagccag gcatctacag attcgtggca ctgggggagc    4860
```

```
gccccteegg catgttegac tegteegtte tetgtgagtg etatgacgeg ggctgtgctt    4920
ggtatgagct cacgcccgcc gagactacag ttagactacg agcgtacatg aacacccegg    4980
ggctccctgt gtgccaggac catcttgaat tttgggaggg cgtctttaca ggcctcaccc    5040
atatagatgc ccatttccta tctcagacaa agcagagcgg ggaaaacttt ccttacctgg    5100
tagcatacca agcaaccgtg tgcgctaggg ctcaagcccc tcccccatcg tgggaccaga    5160
tgtggaagtg tttgactcgc ctcaagccca ccctccatgg gccaacaccc ttgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtc ggcggcgtcc    5340
tggccgcttt ggcctcgtat tgcctgtcaa caggctgcgt ggtcatagtg ggcaggattg    5400
tcctgtctgg gaagccggca attatacctg acagggaagt tctctaccgg gagttcgatg    5460
agatggaaga gtgctctcag cacttaccgt acatcgagca agggatgatg ctcgccgagc    5520
agttcaagca gaaggccctc ggcctcctgc agaccgcgtc ccgtcaggca gaggttgtcg    5580
cccctgctgt ccagaccaac tggcaaaaac tcgaggcctt ctgggcgaag catatgtgga    5640
acttcatcag tgggatacac tacttggcgg gcttgtcaac gttgcctggt aaccccgcca    5700
ttgcttcatt gatggctttt acagctgctg tcaccagccc actaaccact agccaaaccc    5760
tcctcttcaa catactgggg gggtgggtgg ctgcccagct tgccgccccc ggtgccgcca    5820
ccgcctttgt gggcgctggc ttagccggcg ccgcaatcgg cagtgttgga ctggggaagg    5880
tcctcgtgga cattctagca gggtatgcgc cgggcgtggc gggagctctt gtagcattca    5940
agatcatgag cggtgaggtc ccctccacgg aggacctagt caacctgctg cccgccatcc    6000
tctcgcctgg agcccttgta gtcggtgtgg tctgcgcagc aatactgcgc cggcacgtcg    6060
gcccgggcga gggggcagtg caatggatga accggctaat cgccttcgcc tcccggggga    6120
accatgtttc ccccacgcac tatgtgccgg agagcgatgc agctgccgc gtcactacca    6180
tactcagcag cctcactgta acccagctcc tgaggcgact gcaccagtgg ataagctcgg    6240
agtgtaccac tccatgctcc ggttcctggc tgagggacat ctgggactgg atatgcgagg    6300
tgctgagcga ctttaagacc tggctgaaag ccaagctcat gccgcaactg cctgggattc    6360
cctttgtgtc ctgccagcgt gggtataagg gggtctggcg aggggacggc atcatgcaca    6420
ctcgctgcca ctgtggagct gagataactg gacatgtcaa aaacgggacg atgaggatcg    6480
ttggtcctaa gacttgcagg aacatgtgga gtgggacttt ccccattaac gcctacacca    6540
cgggcccctg tactcccctt cctgcgccga actatacgtt cgcgctgtgg agggtgtctg    6600
cagaggaata cgtggagata aggcaggtgg gggacttcca ctacgtgacg ggtatgacta    6660
ctgacaacct taaatgcccg tgccaggtcc catcgcccga ttttttcaca gaattggacg    6720
gggtgcgcct acataggttt gcgccccctt gcaagcccct gctgcgggag gaggtgtcat    6780
tcagagtggg actccacgag tacccggtgg ggtcgcaatt accttgcgag cccgaaccgg    6840
acgtggccgt gttgacgtcc atgctcactg atccctccca tataacagca gaggcggccg    6900
ggagaaggtt ggcgagggga tcaccccccct ctatggccag ctcctcggct agccaactgt    6960
ccgctccatc tctcagggca acttgcacta ccaaccatga ctcccctgat gctgagctca    7020
tagaggccaa cctcctatgg aggcaggaga tgggcggcaa catcaccagg gttgagtcag    7080
agaacaaagt ggtgattctg gactccttcg atccgcttgt ggcagaggag gatgagcggg    7140
aggtctccgt gccccgcagag atactgcgga agtctcggaa attcacccca gccctaccca    7200
```

```
tttgggcgcg gccggactat aacccccccgc tggtggagcc gtggaaaaag cctgactacg    7260
aaccacctgt ggtccatggc tgcccgcttc cacctccaca gtccctcct gtgcctccac     7320
ctcggaagaa gcggacggtg atcctcaccg aatcaaccct acctactgcc ttggccgagc    7380
ttgccaccaa aagttttggc agctcctcaa cttccggcat tacgggcgac gacacgacaa    7440
catcccctga gcccgcctcc tctagctgcc ctcccgactc cgacgctgag tcctattctt    7500
ccatgccccc tctggagggg gagcctgggg atccggatct cagcgacggg tcatggtcga    7560
cggtcagtag tgaggccgac aaggaggatg tcgtgtgctg ctccatgtca tactcctgga    7620
ccggggctct aataactccc tgtagccccg aagaggaaaa gttgccaatc aacccttga     7680
gtaactcgct gttgcgatac cataacaagg tgtactgtac aacatcaaag agcgcctcac    7740
agagggctaa aaaggtaact tttgacagga cgcaagtgct cgacgcccat tatgactcag    7800
tcttaaagga catcaagcta gcggcttcca aggtcagcgc aaggctcctc accttggagg    7860
aggcgtgcca gttgactcca ccccattctg caagatccaa gtatggattc ggggccaagg    7920
aggtccgcag cttgtccggg agggccgtta accacatcaa gtccgtgtgg aaggacctcc    7980
tggaagaccc acaaacacca attcccacaa ccatcatggc caaaaatgag gtgttctgcg    8040
tggaccccgc caagggggggt aagaaaccag ctcgcctcat cgtttaccct gacctcggcg    8100
tccgggtctg cgagaaaatg gccctctatg acattacaca aaagcttcct caggcggtaa    8160
tgggagcttc ctatggcttc cagtactccc ctgcccaacg ggtggagtat ctcttgaaag    8220
catgggcgga aaagaaggac cccatggggtt tttcgtatga tacccgatgc ttcgactcaa    8280
ccgtcactga gagagacatc aggaccgagg agtccatata ccaggcctgc tccctgcccg    8340
aggaggcccg cactgccata cactcgctga ctgagagact ttacgtagga gggcccatgt    8400
tcaacagcaa gggtcaaacc tgcggttaca gacgttgccg cgccagcggg gtgctaacca    8460
ctagcatggg taacaccatc acatgctatg tgaaagccct agcggcctgc aaggctgcgg    8520
ggatagttgc gcccacaatg ctggtatgcg gcgatgacct agtagtcatc tcagaaagcc    8580
aggggactga ggaggacgag cggaacctga gagccttcac ggaggccatg accaggtact    8640
ctgccccctcc tggtgatccc cccagaccgg aatatgacct ggagctaata acatcctgtt    8700
cctcaaatgt gtctgtggcg ttgggcccgc ggggccgccg cagatactac ctgaccagag    8760
acccaaccac tccactcgcc cgggctgcct gggaaacagt tagacactcc cctatcaatt    8820
catggctggg aaacatcatc cagtatgctc caaccatatg ggttcgcatg gtcctaatga    8880
cacacttctt ctccattctc atggtccaag cacccctgga ccagaacctc aactttgaga    8940
tgtatggatc agtatactcc gtgaatcctt ggaccttcc agccataatt gagaggttac    9000
acggcttga cgcctttttct atgcacacat actctcacca cgaactgacg cgggtggctt    9060
cagccctcag aaaacttggg gcgccacccc tcagggtgtg gaagagtcgg gctcgcgcag    9120
tcagggcgtc cctcatctcc cgtggaggga agcggccgt ttgcggccga tatctcttca    9180
attgggcggt gaagaccaag ctcaaactca ctccattgcc ggaggcgcgc ctactggact    9240
tatccagttg gttcaccgtc ggcgccggcg ggggcggcat ttttcacagc gtgtcgcgcg    9300
cccgaccccg ctcattactc ttcggcctac tcctactttt cgtagggta ggcctcttcc     9360
tactccccgc tcggtagagc ggcacacact aggtacactc catagctaac tgttccttt     9420
tttttttttt tttttttttt tttttttttt tttttttttc tttttttttt ttttccctct    9480
ttcttcccttt ctcatcttat tctactttct tccttggtgg ctccatctta gcccctagtca  9540
cggctagctg tgaaaggtcc gtgagccgca tgactgcaga gagtgccgta actggtctct    9600
```

```
ctgcagatca tgt                                                  9613
```

<210> SEQ ID NO 3
<211> LENGTH: 9641
<212> TYPE: DNA
<213> ORGANISM: Hepatitis C virus

<400> SEQUENCE: 3

```
gcctgcctct tacgaggcga cactccacca tggatcactc ccctgtgagg aacttctgtc     60
ttcacgcgga aagcgcctag ccatggcgtt agtacgagtg tcgtgcagcc tccaggaccc    120
cccctcccgg gagagccata gtggtctgcg gaaccggtga gtacaccgga atcgctgggg    180
tgaccgggtc ctttcttgga gcaacccgct caatacccag aaatttgggc gtgccccgc     240
gagatcacta gccgagtagt gttgggtcgc gaaaggcctt gtggtactgc ctgatagggt    300
gcttgcgagt gccccgggag gtctcgtaga ccgtgcaaca tgagcacact tcctaaacct    360
caaagaaaaa ccaaaagaaa caccatccgt cgcccacagg acgttaagtt cccgggtggc    420
ggacagatcg ttggtggagt atacgtgttg ccgcgcaggg gcccacgatt gggtgtgcgc    480
gcgacgcgta aaacttctga acggtcacag cctcgcggac gacgcagcc tatccccaag     540
gcgcgtcgga gcgaaggccg gtcctgggct cagcccgggt acccttggcc cctctatggt    600
aatgagggct gcgggtgggc agggtggctc ctgtccccgc gcggctcccg tccatcttgg    660
ggcccaaacg acccccggcg gaggtcccgc aatttgggta aagtcatcga taccttacg     720
tgcggattcg ccgacctcat ggggtacatc ccgctcgtcg gcgctcccgt aggaggcgtc    780
gcaagagccc tcgcgcatgg cgtgagggcc cttgaagacg ggataaattt tgcaacaggg    840
aacttgcccg gttgctcctt ttctatcttc cttcttgctc tgttctcctg cttagttcat    900
cctgcagcta gtcttgagtg gcggaatacg tctggcctct atgtccttac caacgactgt    960
tccaatagca gtattgtgta tgaggccgat gacgtcattc tgcacacacc cggctgtgta   1020
ccttgtgttc aggacgacaa tacatccacg tgctggaccc cagtgacacc tacggtggca   1080
gtcaggtacg tcggagcaac caccgcttcg atacgcagtc atgtggacct attagtgggc   1140
gcggccacgc tgtgctctgc gctctatgtg ggtgatatgt gtggggccgt cttttctcgtg   1200
ggacaagcct tcacgttcag acctcgtcgc catcaaacgg tccagacctg taactgctcg   1260
ctgtacccag gccatgtttc aggacatcga atggcttggg atatgatgat gaattggtcc   1320
cccgctgtgg gtatggtggt ggcgcacatc ctgcgattgc ccagaccttt gtttgacata   1380
ctggccgggg cccattgggg catcttggcg ggcctagcct attattctat gcagggcaac   1440
tgggccaagg tcgctattgt catgattatg ttttcagggg tcgatgctga acatatgtc    1500
accggtggca gtgtagctca tagtgccaga gggttaacta gccttttag tatgggcgcc    1560
aagcagaaac tgcaattggt caacaccaat ggctcgtggc acatcaacag tactgccctg   1620
aactgcaatg agtccataaa caccgggttc atagctgggt tgttttatta ccataagttc   1680
aactctactg gatgtcctca aaggcttagc agctgcaagc ccatcatttc cttcaggcag   1740
gggtgggggcc ccttgacaga tgctaacatc accggtcctt ctgatgatag accgtattgc   1800
tggcactacg cacctagacc ttgtagtgtt gtcccggcat caagtgtctg cggccctgtg   1860
tactgcttca caccatcgcc agtggtcgta ggcactactg atatcaaagg caagccgacc   1920
tacaactggg gtgagaatga cacagatgtg ttcctgctgg agtccctgcg gcctcccagt   1980
ggccggtggt ttggatgcgc gtggatgaac tccacggggt tcctcaagac gtgtggagct   2040
```

```
cccccttgta acatctatgg gggtgagggg gatcccgaaa atgagacaga cctcttctgc    2100
cccaccgact gcttcaggaa acatcctgag gccacataca gccggtgtgg tgcggggccc    2160
tggttgacac ctcgctgcat ggtcgactat ccataccggc tttggcatta cccatgtaca    2220
gtcaatttca cattgttcaa ggtgaggatg tttgtgggcg gatttgaaca ccggtttacc    2280
gccgcttgta actggaccag gggggagcgc tgcaatatcg aggatcgtga tcgcagcgag    2340
caacatccgc tgctgcattc aacaactgag cttgctatac tgccttgctc tttcacgccc    2400
atgcctgcat tgtcaacagg tctaatacac ctccaccaaa atatcgtgga tgtccaatac    2460
ctttatggtg ttggatctga catggtggga tgggcgctga atgggagtt cgtcatcctc     2520 gttttcctcc tcctggcaga cgcacgcgtg tgcgttgccc tttggctgat gctgatggta    2580
tcacaagcag aagcagcctt ggagaacctt gtcacgctga acgccgtcgc tgctgctggg    2640
acacatggta ttggttggta cctggtagcc ttttgcgcgg cgtggtacgt gcggggtaaa    2700
cttgtcccgc tgacgatcta cggcctgacg ggtctttggt ccctagcatt gcttgtcctc    2760
ttgctccccc aacgggcgta tgcttggtcg ggtgaagaca cgcgctactct cggcgctggg    2820 gtcttggccc tcttcggctt ctttacctta tcaccctggt acaagcattg gatcggccgc    2880
ctcatgtggt ggaaccagta cactatatgt agatgcgagg ccgcccttca agtgtgggtc    2940 cccccttac ttgcacgcgg gagtaggggc ggtgtcatcc tgctaacaag cttgctttat     3000
ccatccttaa ttttttgacat cactaagctg ctgatagcag taataggccc attatactta    3060
atacaggctg ccatcactac cacccccta tttgtgcgcg cacatgtact ggtccgcctt     3120
tgcatgctcg tgcgctccgt gatgggggga aagtacttcc agatggccat actgagcatt    3180
ggcagatggt tcaacaccta cctatatgac cacctagcgc caatgcaaca ttgggccgca    3240
gctggcctca aagacctagc agtggccact gaacctgtaa tatttagtcc catggaaatt    3300
aaggtcatca cctggggcgc ggacacagcg gcttgcggag atattctttg cgggctgccg    3360
gtctccgcgc gattaggccg tgaggtattg ttgggacctg ctgatgatta tcggaaaatg    3420
ggttggcgtc tgttggcccc gatcacagca tacgcccagc aaaactaggg ccttcttggg    3480
actattgtga ccagcttgac tggcagggat aagaacattg tgaccggtga agtgcaggtg    3540 cttttctacgg ctacccagac cttcctaggt acaacagtag gggggttat gtggactgtt    3600 taccatggtg caggttcgaa aacgctcgcg ggcgccaaac atcccgcgct ccaaatgtac    3660
acaaatgtgg atcaggacct cgttgggtgg ccagcccctc caggggctaa gtctcttgaa    3720
ccgtgcgcct gcgggtctgc agacttatac ttggttaccc gcgatgccga tgtcatccct    3780
gctcggcgca gaggggactc cacagcgagc ttgctcagtc ctagacctct cgcctgtctc    3840
aaaggttcct ctggaggtcc tgttatgtgc ccttctgggc atgttgcggg gatctttagg    3900
gctgctgtgt gcaccagagg tgtagcaaaa gccctacagt tcgtaccagt ggaaaccctt    3960
agcacacagg ctaggtctcc atctttctct gacaattcaa ctcctcctgc tgttccacag    4020
agctatcaag tagggtacct tcatgccccg accggcagcg gtaagagcac aaaggtcccg    4080
gccgcttatg tagcacaagg atataatgtt ctcgtgctga atccatcggt ggcggccaca    4140
ctaggcttcg gctcttttcat gtcgcgtgcc tatgggatcg accccaacat ccgcactggg    4200
aaccgcaccg tcacaactgg tgctaaacta acctattcca cctacggtaa gtttcttgcg    4260
gacgggggtt gctccggggg ggcatatgat gtgatcatct gtgatgaatg tcatgcccaa    4320
gacgctacta gcatattggg tataggcacg gtcttagatc aggctgagac ggccggggtg    4380
aggttgacgg ttttagcaac agcaactccc ccaggcagca tcactgtgcc acattctaac    4440
```

```
atcgaagaag tggccctggg ctctgaaggt gagatccctt tctacggtaa ggctataccg    4500
atagccctgc tcaaggggggg gaggcacctt atcttttgcc attccaagaa aaaatgtgat   4560
gaggtggcag ccaaactcag aggcatgggg ctcaacgctg tggcgtacta tagggggtctc  4620 gatgtgtccg tcataccaac aacaggagac gtcgtagttt gcgctactga cgccctcatg   4680
actggattca ccggagactt cgattctgtc atagattgca acgtggctgt tgaacagtac   4740
gttgacctca gcctggaccc cacctttttcc attgagaccc gcaccgctcc ccaagatgcg  4800
gtttcccgca gccaacgtcg tggccgtacg ggccgaggta gactcggtac gtaccgatat   4860
gttgccccgg gtgaaagacc gtctggaatg tttgactcgg ttgttctctg tgagtgctat   4920
gacgcgggct gctcgtggta cgatctgcag ccagctgaga ccacagtcag actgagagct   4980
tacttgaaca cgccggggtt acctgtctgc caggaccatt tagacttttg ggagagcgtc   5040
ttcactggat tgactcacat agacgcccac tttctgtcac agactaagca acagggactt   5100
aacttctcgt tcctaactgc ctaccaagcc actgtgtgtg cccgcgcaca ggcttctcca   5160
ccaagttggg acgagacgtg gaagtgcctc gagcggctta agccaacact acatggacct   5220
acgccccttc tatatcggtt agggcctgtc caaaatgaca tctgcttgac acacccccgtc  5280 acaaaataca tcatggcatg catgtcagct gatctggaag taaccaccag cacctgggtg   5340
ttgcttggag gggtccttgc ggccctagcg tcctactgct tgtcagtcgg ctgcgttgtg   5400
atcgtgggtc atattgagct gagaggcaag ccggcactcg taccggacag agaggtgttg   5460
tatcaacaat acgatgagat ggaggagtgc tcacaagccg ccccatatat cgaacaagct   5520
caggcaatcg cccaccagtt caaggaaaaa atcctaggac tgctgcagcg agccacccag   5580
caacaagctg tcatcgagcc catagtagct accaactggc aaaaacttga gaccttctgg   5640
cacaagcata tgtggaattt tgtgagtggg atccaatacc tagcaggcct ctccactttg   5700
cccggcaacc cagctgtggc gtctcttatg gcgttcactg cttcagtcac cagtcccctg   5760
acgaccaacc agactatgtt ttttaacata tcgggggggt gggtcgccac ccgtttggca   5820
gggccccaga gctcttccgc gttcgtggta agcggcttag ccggcgctgc cataggggggt 5880 ataggcctgg gcagggtctt gctggacatc ctggcaggat acgagctggg tgtctcaggc   5940
gccttggtgg cttttaagat catgggagga gaactcccca ctactgagga catggtcaac   6000
ctgttgcccg ccatactatc tccgggcgct ctcgtcgtcg tgtgtatatg cgctgccata   6060
ctacgtcgac acgtaggacc tgggggaggga gcggtacagt ggatgaacag gctcatcgca   6120
ttcgcgtccc ggggcaacca cgtctcacca acgcactatg ttcccgagag cgatgctgca   6180
gcgagggtca ccgcattgct gagttctcta actgtcacaa gtctgctccg gcggttacac   6240
aagtggatca atgaagacta cccaagccct tgcagcggcg attggctgcg tgacatctgg   6300
gactgggttt gctcggtgtt gtccgacttc aagacgtggc tctctgctaa gattatgcca   6360
gcactccctg ggctgccctt catctcctgt caaaagggat acaagggcgt gtggcggggg   6420
gatggtgtga tgtcgacacg ctgtccttgc ggggcatcaa tcactggcca cgtgaagaat   6480
gggtccatgc ggcttgcggg gccgcgtatg tgtgctaaca tgtggcacgg tactttcccc   6540
atcaatgagt acaccaccgg acccagcaca ccttgcccat cacccaacta cactcgcgca   6600
ctatggcgcg tggctgccag cagctacgtt gaggtgcgcc gggtggggga cttccattat   6660
attacggggg ctacagaaga tgagctcaag tgtccgtgcc aagtgccggc tgctgagttc   6720
tttactgaag tggatggggt gagactccac cgttacgccc ctccatgtaa gccccctgttg 6780
```

-continued

```
agagaagaga tcactttctc ggtagggttg cattcctacg cgataggatc tcaactcccc    6840
tgtgagccag aaccagatgt ttctgtgttg acctcgatgt tgagagaccc ttctcatatc    6900
accgccgaga cggcagcgcg ccgccttgcg cgcgggtccc ctccatcaga ggcaagctca    6960
tccgccagcc aactatcggc tccgtcgttg aaggccactt gccagacgca taggcctcat    7020
ccagacgctg agctggtgga cgccaacttg ttatggcggc aagagatggg cagcaacatt    7080
acacgggtgg agtctgaaac gaaggttgtg attcttgatt cattcgaacc tctgagagcc    7140
gaagctgacg acgccgagct ctcggtggct gcagagtgtt caagaagcc tcccaagtat     7200
cctccagccc ttcctatctg gccaggccg gactacaacc ctccactgtt ggaccgctgg     7260
aaagcaccgg attatgtacc accaactgtc catggatgtg ccttaccacc acggggcgct    7320
ccaccggtgc ctcctcctcg gaggaaaaga acaatccagc tggacggctc caatgtgtcc    7380
gcggcgctag ctgcgctagc ggaaaaatca ttcccgaccc caaaatcgca ggaagagaat    7440
agctcatcct ctggggtcga cacacagtcc agcactacct ccaggatgcc cccctctcca    7500
ggaggggagt ccgactcaga gtcatgctcg tccatgcctc ctctcgaggg agagccgggc    7560
gatccggact tgagttgcga ctcttggtcc accgttagtg acaacgagga gcagagcgcg    7620
gtctgctgct ccatgtcata ctcctggacc ggggctctaa taactccctg tagccccgaa    7680
gaggaaaagt tgccaatcaa ccctttgagt aactcgctgt tgcgatacca taacaaggtg    7740
tactgtacaa catcaaagag cgcctcacag agggctaaaa aggtaacttt tgacaggacg    7800
caagtgctcg acgcccatta tgactcagtc ttaaaggaca tcaagctagc ggcttccaag    7860
gtcagcgcaa ggctcctcac cttggaggag gcgtgccagt tgactccacc ccattctgca    7920
agatccaagt atggattcgg ggccaaggag gtccgcagct tgtccgggag ggccgttaac    7980
cacatcaagt ccgtgtggaa ggacctcctg gaagacccac aaacaccaat tcccacaacc    8040
atcatggcca aaaatgaggt gttctgcgtg gaccccgcca aggggggtaa gaaaccagct    8100
cgcctcatcg tttaccctga cctcggcgtc cgggtctgcg agaaaatggc cctctatgac    8160
attacacaaa agcttcctca ggcggtaatg ggagcttcct atggcttcca gtactcccct    8220
gcccaacggg tggagtatct cttgaaagca tgggcggaaa agaaggaccc catgggtttt    8280
tcgtatgata cccgatgctt cgactcaacc gtcactgaga gagacatcag gaccgaggag    8340
tccatatacc aggcctgctc cctgcccgag gaggcccgca ctgccataca ctcgctgact    8400
gagagacttt acgtaggagg gcccatgttc aacagcaagg gtcaaacctg cggttacaga    8460
cgttgccgcg ccagcggggt gctaaccact agcatgggta acaccatcac atgctatgtg    8520
aaagccctag cggcctgcaa ggctgcgggg atagttgcgc ccacaatgct ggtatgcggc    8580
gatgacctag tagtcatctc agaaagccag gggactgagg aggacgagcg gaacctgaga    8640
gccttcacgg aggccatgac caggtactct gcccctcctg gtgatccccc cagaccggaa    8700
tatgacctgg agctaataac atcctgttcc tcaaatgtgt ctgtggcgtt gggcccgcgg    8760
ggccgccgca gatactacct gaccagagac ccaaccactc cactcgcccg ggctgcctgg    8820
gaaacagtta gacactcccc tatcaattca tggctgggaa acatcatcca gtatgctcca    8880
accatatggg ttcgcatggt cctaatgaca cacttcttct ccattctcat ggtccaagac    8940
accctggacc agaacctcaa ctttgagatg tatggatcag tatactccgt gaatcctttg    9000
gaccttccag ccataattga gaggttacac gggcttgacg ccttttctat gcacacatac    9060
tctcaccacg aactgacgcg ggtggcttca gccctcagaa aacttggggc gccacccctc    9120
agggtgtgga gagtcgggc tcgcgcagtc agggcgtccc tcatctcccg tggagggaaa    9180
```

| | |
|---|---|
| gcggccgttt gcggccgata tctcttcaat tgggcggtga agaccaagct caaactcact | 9240 |
| ccattgccgg aggcgcgcct actggactta tccagttggt tcaccgtcgg cgccggcggg | 9300 |
| ggcggcattt ttcacagcgt gtcgcgcgcc cgaccccgct cattactctt cggcctactc | 9360 |
| ctactttcg taggggtagg cctcttccta ctccccgctc ggtagagcgg cacacactag | 9420 |
| gtacactcca tagctaactg ttccttttt tttttttt tttttttt tttttttt | 9480 |
| tttttttctt tttttttt ttccctcttt cttcccttct catcttattc tactttcttt | 9540 |
| cttggtggct ccatcttagc cctagtcacg gctagctgtg aaaggtccgt gagccgcatg | 9600 |
| actgcagaga gtgccgtaac tggtctctct gcagatcatg t | 9641 |

<210> SEQ ID NO 4
<211> LENGTH: 9603
<212> TYPE: DNA
<213> ORGANISM: Hepatitis C virus

<400> SEQUENCE: 4

| | |
|---|---|
| acctgctctc tatgagagca acactccacc atgaaccgct cccctgtgag gaactactgt | 60 |
| cttcacgcag aaagcgtcta gccatggcgt tagtatgagt gttgtacagc ctccaggacc | 120 |
| cccctcccg ggagagccat agtggtctgc ggaaccggtg agtacaccgg aatcgccggg | 180 |
| atgaccgggt cctttcttgg attaacccgc tcaatgcccg gaaatttggg cgtgcccccg | 240 |
| caagactgct agccgagtag tgttgggtcg cgaaaggcct tgtggtactg cctgataggg | 300 |
| tgcttgcgag tgccccggga ggtctcgtag accgtgcacc atgagcacga atcctaaacc | 360 |
| tcaaagaaaa accaaacgta acaccaaccg ccgcccaatg gacgttaagt tcccgggtgg | 420 |
| tggccagatc gttggcggag tttacttgtt gccgcgcagg ggcccagat ggggtgtgcg | 480 |
| cgcgactcgg aagacttcgg agcggtcgca acctcgtgga agacgccaac ctatcccaa | 540 |
| ggcgcgtcga cccgagggaa ggtcctgggc acaaccagga tatccatggc ctctttacgg | 600 |
| taatgagggt tgtgggtggg caggatggct cttgtcccc cgtggctctc gaccgtcttg | 660 |
| gggcccaaat gatccccggc ggaggtcccg caatttgggt aaggtcatcg atacctaac | 720 |
| ctgcggcttc gccgacctca tgggatacat cccgctcgta ggcgccccg tgggtggcgt | 780 |
| cgccagggcc ctggcacatg tgtcagggc tttggaggac gggatcaatt atgcaacagg | 840 |
| gaatctcccc ggttgctcct tttctatctt cctcttggca cttctttcgt gcctgactgt | 900 |
| ccccgcttcg gccgttaact atcgcaatgt ctcgggcatc taccatgtca ccaatgactg | 960 |
| cccgaattca agcatagtgt atgaggccga ccatcacatc ttgcaccttc caggttgcgt | 1020 |
| gccctgcgtg agagagggga atcagtcacg ctgctgggtg gcccttactc ctaccgtcgc | 1080 |
| agcgccatac atcggcgcac cgcttgagtc cttacggagt catgtggatt tgatggtggg | 1140 |
| ggccgccact gtttgctcgg gtctttacat cggggacctg tgtggcggct tgttcctagt | 1200 |
| tggccagatg ttttcattcc gaccacggcg ccactggacc acccaggatt gcaattgttc | 1260 |
| catctacaca gggcacatta caggccacag aatggcctgg gacatgatga tgaactggag | 1320 |
| tccaacaacc accttagttc tcgcccaggt catgaggatc ccaaccactc tggtagactt | 1380 |
| actctctgga ggccactggg gtgtcctcgt gggagtggcc tatttcagca tgcaggccaa | 1440 |
| ttgggccaaa gtcatcttgg tcctattcct ctttgcaggg gttgatgccg agactcacgt | 1500 |
| gtctggggca gcagtcggcc ggagtaccgc cggcttggct aacctctttt cttctgggtc | 1560 |
| taagcagaat ttacagctca tcaacagcaa tgggagctgg catataaata ggactgccct | 1620 |

-continued

```
taactgcaat gacagcttaa acactgggtt cttggctagc ttgttctaca cccacaagtt      1680
taacagctca gggtgttccg aacggctcgc gtgctgcaag agccttgaca gctacggcca      1740
aggctggggc ccactcgggg tcgctaacat cagcggctcg tctgatgaca ggccttattg      1800
ctggcactac gcgcctcggc cgtgcggggat tgtgccagca tccagtgtgt gtggccccgt      1860
gtattgtttc actcccagcc ctgtcgtggt cggtactact gatcacgtcg ggtccctac       1920 ttacacctgg ggggagaatg agactgatgt cttccttttg aactcgacca gaccgccgca      1980
tggtgcgtgg tttggatgcg tgtggatgaa cagtaccggg ttcaccaaaa cctgtggcgc      2040
ccctccatgc gaggttaaca ccaataatgg gacctggcac tgccccaccg attgcttcag      2100
gaagcatccg gagactacct acgccaagtg cggatcaggg ccttggatca caccgcgctg      2160
cctgattgat tacccgtacc ggctgtggca tttcccgtgc accgccaact tctccgtctt      2220
taacatcagg acatttgtcg gcggtataga gcatcggatg caagcggcat gcaactggac      2280 cagggggaa gtctgtggct tggagcacag ggatcgcgta gagctatcac ccctgctcct      2340
taccactaca gcgtggcaga tcctcccctg ctctttcacc actttacctg ccctctccac      2400
cggcttgatc cacctccacc aaaatatcgt ggacgtccag tacctctatg gtgttgggtc      2460
tgcagtggta tcttgggccc ttaagtggga atatgtggtg ctcgcgttcc tgcttctcgc      2520
ggacgcgaga gtctctgcct gcctatggat gatgtttatg gtaagtcaag ttgaggcggc      2580
tctgtccaac ctgattaaca tcaatgctgc ttcagccgct ggtgcccaag gcttctggta      2640
cgccatcctc ttcatctgca ttgtctggca tgtcaagggc tggttccag ctgctgctgc      2700 ctacgcagcc tgcgggctgt ggcccctgtt tctcctgctt ctgatgctgc tgagagggc       2760 ttatgcatac gaccaggaag tggcagggtc ccttggcggc gccatcgttg tcatgctgac      2820
cattctgaca ctgtctccgc actacaagtt atggctggct aggggattgt ggtggatcca      2880
atattttata gctaggaccg aggctgtgct gcatgtctat attccatcct caacgtgcg       2940 cgggcctcgc gactcagtga ttgttcttgc agtcctggtc tgtccacacc tagtatttga      3000
catcacaaaa tatcttctgg ccatcttagg gcccctccac atactccagg cctcgctcct      3060
acgcatccct tactttgtga gggcacaagc gctggttaag atctgcagct tgttgcgtgg      3120
ggtagtttat ggcaagtact ccaaatggt cgtgcttaaa gcaggggccc tgactggtac       3180
ttacatctat gaccacctta ctcccatgtc agattgggcc gctacgggcc tccgcgattt      3240
ggcggtggcc ctagagccag ttgtgttcac gcccatgag aagaaagtca tcgtctgggg       3300
cgctgacacc gctgcgtgcg gagacatcat aaggggatta cctgtttcgg ccaggttggg      3360
caatgaaatc ttgctcggac cagccgatac agaaacatca aaggggtgga gactccttgc      3420
ccccatcaca gcatacgcgc agcagacccg cggcttgttc agcaccatcg taacgagcct      3480
cactggcagg gacaccaatg agaattgtgg cgaagtgcag gtcttatcca ccgctacgca      3540
gtccttcctg gtactgcgg ttaacggcgt gatgtggacc gtctaccacg gggcgggtgc       3600
caagaccatc agcggcccga agggacctgt caatcaaatg tacactaatg ttgaccaaga      3660
cttggtgggg tggccagcac ccccccggagt cagatctctt gctccgtgca cctgcggctc     3720
ggcagacttg tatctagtca ccaggcacgc agatgtaata cccgtgcgca ggagaggaga      3780
caccagagga gctctcttga gccctagacc aatatccact cttaagggat cttccggagg      3840
tccgctgctg tgcccatgg gacacgccgc cggcatattc cgtgcggcgg tgtgtactcg       3900
aggggtagcc aagcggtag acttcgtccc ggttgaatct cttgagacta ccatgagatc      3960
accagtgttc actgacaact caacacctcc agcagtgccc cagacctacc aggtcgcgca      4020
```

```
cctacacgca ccaacaggaa gtggcaagag caccaaagtc ccggcggcgt atgctgccca    4080
aggctataaa gtgctagtgc tcaatccttc ggttgcggcc acactgggtt ttgggggtata   4140
catgtccaag gcatatggca tcgacccgaa catccggtcg ggagtcagga ccatcaccac    4200
gggtgcgcca atcacgtact caacgtatgg taagttcctg gctgatggag gttgcagcgg    4260
agggccatac gacataatca tctgtgacga gtgccattcc actgactcca caacgatcct    4320
tggcataggc acagtcctgg accaagcgga gaccgctgga gtgcgcctca ccgtgctcgc    4380
gactgctact ccgccagggt cagtgactac acctcattcc aacatagagg aggtcgccct    4440
gccaacaacg ggggaaatcc ccttttacgg caaggcgatc cctctggagc tgattaaggg    4500
gggcagacat ctcatcttct gccactcaaa gaaaaagtgt gatgaactgg ccagacaact    4560
gacatctctt ggtctgaatg ccgtagccta ctacagaggc ttagacgttt cggtgattcc    4620
cacgtctggg gacgtcgtgg tatgcgccac ggacgccctc atgacgggtt ttaccggcga    4680
ctttgactca gtgatagact gcaatacatc tgtgatacag actgttgacc tcagcttgga    4740
ccccaccttc tccatagaga ctacaaccgt tccccaggac gcggtatccc gcagccagcg    4800
gagaggccgc actggtaggg ggaggttggg cacataccgg tatgtcaccc cgggagagag    4860
accatcaggc atgtttgaca ctgcagtgct ttgcgagtgc tacgatgccg ggtgtgcctg    4920
gtacgagctg acacctgctg aaaccacaac aaggctgaaa gcttacttcg acacaccagg    4980
ccttcctgtg tgccaagacc atctggagtt ctgggagagc gtctttacag ggttaaccca    5040
catagacggt catttcctat cccagaccaa gcaatcgggt gagaatttcc cgtatcttgt    5100
tgcttaccaa gccacggtgt cgccaaggc tctggcgcct ccaccaagct gggacaccat    5160
gtggaagtgc ctaattcgcc ttaagcccac cctgcacggg cccacacccc tcctctacag    5220
actggggtct gtgcagaatg aagtggtgct cacccatccc atcaccaaat acatcatggc    5280
ttgcatgtca gctgatctcg aggtagtgac aagtacgtgg gtcttggtgg gcggcgtcct    5340
ggcagctctg gcttcttact gtcttttcagt gggcagcgta gtgattgttg ggagagtcgt    5400
cctgtcgggc caacctgctg tcattcccga tcgcgaagtg ctctaccaac agttcgacga    5460
aatggaggag tgttccaaac acctcccact agtcgagcac gggttacaac tggctgagca    5520
gttcaagcag aaggccttag gtctcctaaa tttcgctggc aagcaagccc aagaggcaac    5580
accagtgatc cagtctaact tcgctaaact tgagcagttt tgggcgaagc acatgtggaa    5640
tttcatcagc ggcattcaat atctcgctgg actgtctacc ttgccaggca atcctgtcat    5700
tgcttccctc atgtccttta ctgctgctgt tacaagccct ctgaccaccc aacaaacccc    5760
cctttttaac atcttggggg gatgggtggc ctcgcagatt gcgactccga cggcttctac    5820
cgcattcgtc gtgagcggct ggcgggggc ggcagttggc agtgtgggcc ttggcaaaat    5880
tttggtggac attctcgccg gttacggcgc cggcgtagct ggcgctgtgg ttaccttcaa    5940
gatcatgagc ggcgagatgc cttccacaga ggacttggta aatttgctcc cggccattct    6000
atcgcccgga gcattggtag tggggtggt atgcgcggcg atttttgcgcc gccacgtggg    6060
cccgggcgaa ggggctgtgc agtggatgaa ccgtctaatt gcgttcgcat cgcgaggcaa    6120
tcacgtgtct cccacgcatt acgtccctga gtccgacgcg gcagcccgcg tgaccaccat    6180
actatcatcc ctcactgtga catcccttct cagacgcctc cacaagtgga tcaatgaaga    6240
ttgctccacc ccatgtgccg aatcttggct atgggaggta tgggattggg tctgcaccgt    6300
gctgagtgac ttcaagacgt ggctaaaagc caagttgctg cccctcatgc caggcatccc    6360
```

-continued

```
cttcctctca tgccagaggg gctataaggg agagtggcgc ggagatggcg tgatgcatac    6420
cacatgcccc tgcggagcag atctggcagg tcacatcaag aacggctcga tgagaatcac    6480
cgggccgaaa acctgcagca acacatggca tggtaccttc cccatcaatg cttacaccac    6540
aggccctggt gtacccatcc cggcgccgaa ctacaagttc gcgctttgga gggtgtccgc    6600
cgaggactac gtggaggttc gcagagtggg tgatttccat tatgtcaccg gggtaacaca    6660
agacaacatc aagtgcccct gccaagttcc ggccccagag ttcttcacgg aagtggacgg    6720
catcaggcta caccgccacg ccccgaagtg caaacccttg ctgcgggacg aagtgtcgtt    6780
ctcagtagga ctcaattcgt tcgtagtggg atcacaactc ccatgcgagc cagagccgga    6840
cgtggcagtg ctaacatcca tgctgacaga cccatcacac ataacggcgg aatcggcgcg    6900
tcggagattg gctcgagggt cacgaccctc gctagctagt tcctcggcga gtcagctttc    6960
cgccccgtct ctcaaggcca cgtgtaccgc tccccatgac tcccctggta ctgatctcct    7020
cgaggctaac ctcttgtggg ggtctaccgc taccagggtt gagacggacg agaaggtaat    7080
aatactagac tcttttgagt catgtgtggc tgagccaaat gatgacaggg aagtctcggt    7140
tgccgcggaa atcctgcgtc cgaccaagaa gttccctcca gcactaccga tctgggcccg    7200
gccggattac aatccaccct cttaccgagac gtggaagcag caggactaca agcctccgac    7260
cgtccacggg tgcgctctgc ctcccggcaa gcagcccccc gttcctcctc ccaggaggaa    7320
acggacggta cagctcactg agtccgttgt ttctaccgct ttggcagagc tggccgcaaa    7380
gacctttggc cagtcagagc cgagctcaga ccgtgataca gaccttacca ccccaactga    7440
gaccacagac tcgggcccca tcgtcgtgga tgatgcatcc gatgacggat cttattcgtc    7500
aatgcctcca ctagagggggg agcccggtga cccggacttg acatcagact cttggtccac    7560
tgttagcgga tcggaggacg tcgtgtgctg ctccatgtca tactcctgga ccggggctct    7620
aataactccc tgtagccccg aagaggaaaa gttgccaatc aaccctttga gtaactcgct    7680
gttgcgatac cataacaagg tgtactgtac aacatcaaag agcgcctcac agagggctaa    7740
aaaggtaact tttgacagga cgcaagtgct cgacgcccat tatgactcag tcttaaagga    7800
catcaagcta gcggcttcca aggtcagcgc aaggctcctc accttggagg aggcgtgcca    7860
gttgactcca ccccattctg caagatccaa gtatggattc ggggccaagg aggtccgcag    7920
cttgtccggg agggccgtta accacatcaa gtccgtgtgg aaggacctcc tggaagaccc    7980
acaaacacca attcccacaa ccatcatggc caaaaatgag gtgttctgcg tggaccccgc    8040
caagggggt aagaaaccag ctcgcctcat cgtttaccct gacctcggcg tccgggtctg    8100
cgagaaaatg gccctctatg acattacaca aaagcttcct caggcggtaa tgggagcttc    8160
ctatggcttc cagtactccc ctgcccaacg ggtggagtat ctcttgaaag catgggcgga    8220
aaagaaggac cccatggggtt tttcgtatga tacccgatgc ttcgactcaa ccgtcactga    8280
gagagacatc aggaccgagg agtccatata ccaggcctgc tccctgcccg aggaggcccg    8340
cactgccata cactcgctga ctgagagact ttacgtagga gggcccatgt tcaacagcaa    8400
gggtcaaacc tgcggttaca gacgttgccg cgccagcggg gtgctaacca ctagcatggg    8460
taacaccatc acatgctatg tgaaagccct agcggcctgc aaggctgcgg ggatagttgc    8520
gcccacaatg ctggtatgcg gcgatgacct agtagtcatc tcagaaagcc aggggactga    8580
ggaggacgag cggaacctga gagccttcac ggaggccatg accaggtact ctgcccctcc    8640
tggtgatccc cccagaccgg aatatgacct ggagctaata acatcctgtt cctcaaatgt    8700
gtctgtggcg ttgggccccgc ggggccgccg cagatactac ctgaccagag acccaaccac    8760
```

```
tccactcgcc cgggctgcct gggaaacagt tagacactcc cctatcaatt catggctggg    8820
aaacatcatc cagtatgctc caaccatatg ggttcgcatg gtcctaatga cacacttctt    8880
ctccattctc atggtccaag acaccctgga ccagaacctc aactttgaga tgtatggatc    8940
agtatactcc gtgaatcctt ggaccttcc agccataatt gagaggttac acgggcttga    9000
cgccttttct atgcacacat actctcacca cgaactgacg cgggtggctt cagccctcag    9060
aaaacttggg gcgccacccc tcagggtgtg aagagtcgg gctcgcgcag tcagggcgtc    9120
cctcatctcc cgtggaggga agcggccgt ttgcggccga tatctcttca attgggcggt    9180
gaagaccaag ctcaaactca ctccattgcc ggaggcgcgc ctactggact tatccagttg    9240
gttcaccgtc ggcgccggcg ggggcgacat ttttcacagc gtgtcgcgcg cccgaccccg    9300
ctcattactc ttcggcctac tcctactttt cgtaggggta ggcctcttcc tactccccgc    9360
tcggtagagc ggcacacact aggtacactc catagctaac tgttcctttt tttttttttt    9420
tttttttttt tttttttttt tttttttttc tttttttttt ttttccctct ttcttccctt    9480
ctcatcttat tctactttct ttcttggtgg ctccatctta gccctagtca cggctagctg    9540
tgaaaggtcc gtgagccgca tgactgcaga gagtgccgta actggtctct ctgcagatca    9600
tgt                                                                  9603
```

<210> SEQ ID NO 5
<211> LENGTH: 9620
<212> TYPE: DNA
<213> ORGANISM: Hepatitis C virus

<400> SEQUENCE: 5

```
acccgcccct tattggggcg acactccacc atgatcactc ccctgtgagg aactactgtc      60
ttcacgcaga aagcgtctag ccatggcgtt agtatgagtg tcgaacagcc tccaggaccc     120
cccctcccgg gagagccata gtggtctgcg gaaccggtga gtacaccgga attgccggga     180
tgaccgggtc ctttcttgga taaacccgct caatgcccgg agatttgggc gtgccccgc     240 gagactgcta ccgagtagt gttgggtcgc gaaaggcctt gtggtactgc ctgatagggt     300
gcttgcgagt gccccgggag gtctcgtaga ccgtgcaaca tgagcacgaa tcctaaacct     360
caaagaaaaa ccaaaagaaa caccaaccgc cgcccacagg acgtcaagtt cccgggcggt     420
ggtcagatcg ttggtggagt ttacttgttg ccgcgcaggg gcctaggtt gggtgtgcgc     480 gcaactcgga agacttcaga acggtcgcaa ccccgtggac ggcgtcagcc tatccccaag     540
gcgcgccagc ccacgggccg gtcctggggt caacccgggt acccttggcc ctttatgcc     600 aatgagggcc tcgggtgggc agggtggttg ctctccccc gaggctctcg gcctaattgg     660
ggccccaatg accccggcg gaaatcgcgc aacttgggta aggtcatcga taccctgacg     720
tgcggattcg ccgacctcat ggggtacatc ccgctcgtag gcgccccgt tgggggcgtc     780 gcaagggctc tcgcacacgg tgtgagggtc cttgaggacg gggtaaacta tgcaacaggg     840
aatttacccg gttgctcttt ctctatcttt atccttgcac ttctttcatg cctgactgtc     900
ccgacctctg ccgttcccta ccgaaatgcc tctggggttt atcatgtcac caatgattgc     960
ccaaactctt ctatcgtcta tgaggctgaa gacctgatct acacgcacc tggttgcgtg    1020 ccctgtgtta ggcagggtaa tgtcagtagg tgctgggtcc agatcacccc cacactgtca    1080
gccccgagcc tcgagcggt cacgctcct cttcggaggg ccgttgacta cttagcgggg    1140
ggggctgccc tttgctccgc gttatacgtc ggagacgcgt gcggggcagt gttttggta    1200
```

```
ggtcaaatgt tcacctatgg ccctcgccgg cataatgttg tgcaggactg caactgttcc    1260
atttacagtg gccacatcac cggccaccgg atggcatggg acatgatgat gaattggtca    1320
cctacaacag ctttggtgat ggcccagttg ttacggattc cccaggtggt cattgacatc    1380
attgccgggg cccactgggg ggtcttgttc gccgccgcat actacgcgtc ggcggctaac    1440
tgggccaagg ttgtgctggt cctgtttctg tttgcggggg tcgatgccag cacccgcact    1500
gtgggtggta gtgcggccca aggcgcgcgc gggctcgctt cacttttcac ccctgggccg    1560
cagcagaact tgcagctcat aaataccaac gggagctggc acatcaacag aactgccctt    1620
aactgtaatg acagcctcca gactgggttt gtagccggcc tcctgtatta tcacaagttc    1680
aactccactg ggtgtccgca gcggatggct agctgtaggc ccctcgccgc attcgaccag    1740
ggctggggaa ctatcagcta tgccgccgtg tcgggcccca gtgatgacaa gccctattgc    1800
tggcactacc ccccacgccc gtgcggaata gtgccagcgc gaggtgtctg cggtccggtc    1860
tattgtttta cacctagccc ggtggtcgtc ggcaccacag accgcaaggg gaatcccact    1920
tacagttggg gcgaaaatga gactgacatc tttctcttga acaacacgag gccccctact    1980
ggcaactggt ttggctgcac ctggatgaat tccacagggt ttgtcaagac ttgcggggct    2040
ccaccctgca acttagggcc tacaggcaac aatagcctta gtgtcctac tgattgcttc    2100 cgcaagcacc cagacgccac ctacaccaag tgtgggtcag accctggct cactccccgg    2160 tgtctggtgc attaccctta ccggttgtgg cattacccgt gcaccctaaa ttacaccatc    2220
ttcaaggtgc gcatgtacat tgggggcctc gagcacaggc tcgaggtggc atgcaactgg    2280
acccgtggtg agcggtgtga tcttgaagac agggataggg ccgagctgag cccgctccta    2340
cataccacca cgcagtgggc catattgccg tgctctttca cacccacacc cgctcttagc    2400
actggtctca tacacttaca tcaaaatata gtagacaccc agtatcttta cggtctgagc    2460
tccagcatcg tctcgtgggc cgttaagtgg gagtacatag tgctggcctt cttattactt    2520
gctgatgccc gtatttgtac ttgcctatgg atcatgctcc tggtttgtca ggccgaagcg    2580
gccctggaga acgtcattgt cctaaacgcg gctgcggctg cggggactca tgggttttc    2640 tggggcctgc tcgtcatctg cttcgcctgg cacttcaagg caggttggt ccctgggggcc    2700 acctaccttt gcttgggcat ttggccatta ctcttactcc tttcctcct gccccaaagg    2760 gctctagccc tggactcaag cgatggcggg actgtggtt gtcttgtgtt aaccatcctt    2820
acaatcttca cactcacccc cgggtacaag aagatggtag tgttggtcat atggtggctt    2880
cagtatttca tagcccgggt agaggccttt atccatgtgt gggtgccccc gttgcaggtt    2940
aggggtggtc gtgatgctat tatcatgctc acatgccttt tccatcctgc cctggggttt    3000
gaggtcacga aaatcctcct cgggatacta ggtcctttgt acctgctgca gtactcgctc    3060
atcaagctgc cttatttcat cagggcgcgc gccctgctga gggcgtgcct gctagcgaag    3120
cacttggcct gtggcaggta cgtgcaggcg gccttgctcc accttggtag ctgaccggga    3180
acgtacattt atgaccacct tgcccccatg aaggattggg cagcgtccgg gctgcgcgac    3240
ttagcagtgg ccacggagcc catcatattc tcccctatgg agacgaaggt catcacgtgg    3300
ggggctgaca cggccgcatg tgggacata cttgccggcc ttcctgtatc agctaggcga    3360
ggccatgaaa tcttcctggg gccagccgat gacatcagag aggcgggctg gcgacttctc    3420
gcccctatca ccgcgtatgc gcagcagacg cgagggtgc tgggcgctat aattgtcagc    3480
ctaaccggcc gggacaaaaa tgaagccgag ggtgaggtgc aggtcctatc cacggcaaca    3540
caaacattcc ttggtacttg catcaatggg gtgatgtgga ccgtcttcca cggggccggc    3600
```

```
tctaagaccc ttgctggccc caaaggccca gtggtgcaaa tgtacactaa tgtagacaaa      3660
gatctggtgg gatggcctac ccccctgga acgcgctcgc tcactccgtg cacttgcgga      3720
tcggcggacc tgtacctggt taccaggcat gcagacgtcg ttccagctcg tagacggggc      3780
gacactcgtg cctccctgct cagcccgaga cccattagct atctcaaggg ttcatcaggc      3840
ggcccagtca tgtgcccttc cgggcacgtg gtgggtgttt tcagggctgc cgtgtgcacg      3900
cggggtgtcg cgaaggcgct cgatttcatt ccggttgaaa acctggaaac cacgatgcgc      3960
tcgcccgtgt tcactgacaa cagcacaccc cctgcggtcc ctcacgagtt ccaagtggga      4020
cacctccatg cgcctaccgg gagcggaaag agcacgaagg tacccgctgc ttatgcggcc      4080
caagggtaca aggtgctggt gctgaatcca tctgtcgcgg cgacgctcgg gttcggggca      4140
tacatgtcaa gagcttatgg cgtggacccc aacatcagga ccggagttag gactgtcacc      4200
accggagctg ctatcacata tctacttac ggcaagttcc tcgctgacgg ggggtgttca       4260
gggggcgcgt atgatgtaat catatgcgac gagtgccatt cccaggacgc taccaccatc      4320
cttgggatag gcacagtcct cgaccaggca gagacggctg gagccaggct cgtcgtcttg      4380
gccacggcca ctcccccgg cagtgtgaca acgccccacc caacatcga ggaggtggcc        4440 ctgccttcgg aggggaaat cccttctac ggcagggcta tccccttgc tctcattaag         4500 ggcggtaggc atctcatctt ctgccactct aagaaaaagt gtgatgaact tgccaagcaa      4560
ttgactagcc aaggcgtcaa cgccgtggca tactacagag gactagacgt cgccgtcata     4620
cccgcgacag gagatgtggt cgtgtgcagc acggacgcgc tcatgacggg gtttaccggc     4680
gactttgatt ctgtcataga ctgcaacacc accgtcacgc agacggtgga tctcagtctg    4740
gatcccacct ttaccattga gactaccacg gtgccccagg acgcagtgtc cagaagccaa    4800 cgtagggtc gcacgggaag aggtaggcac ggcatatatc gatatgtctc gtctggggag    4860
agaccgtctg gcatttttcga ctccgtggtg ctctgtgagt gctacgatgc cggatgtgca    4920
tggtatgatc tgaccctgc agagactacc gtgaggttgc gtgcttacct gaacacccc      4980 ggactccctg tctttcaaga ccacctggaa ttttgggagg gggtgttcac agggctcact     5040
aacatcgacg cccacatgct gtcacagact aaacaggggtg gggagaactt cccataccctt  5100 gtagcgtacc aagcaacagt ctgtgtccgc gcgaaagcgc ccccccccag ctgggacaca     5160
atgtggaagt gcatgctccg tcttaagccg accctgaccg gccccacccc cctcctgtac     5220
aggctggggg ccgtccagaa tgagatcaca ttgacgcacc ccatcaccaa gtacattatg     5280
gcttgcatgt ccgcggactt ggaggtcatt accagcacgt gggttctggt gggggtgtc      5340 gtggcggcct tagcgtccta ctgcttgacg gtgggctcgg tggccatagt cggtagaatc     5400
atcctatctg ggagacctgc catcattccc gacaggagg tgtttgtacca acaatttgat     5460 gagatggagg agtgttcggc ctcgttgccc tacatggacg aggcacgtgc tattgccgag     5520
caattcaagg agaaagtgct tggcctcatt ggcacggccg tcagaaagc tgagactctg     5580 aaaccggcag ccacgtccat gtggaacagg gctgagcagt tctggcaaa acacatgtgg     5640 aactttgtca gtgggatcca atacttggcc ggtctttcaa ccttgccggg caatcctgcc     5700
gtggccactt tgatgtcttt caccgccgcg gtaacctccc cccttacaac tcagcagacc     5760
ctcctcttta atattctagg agggtgggtg gcctcgcaga tcgcgccacc cacggccgcc     5820
actgcgttcg tcgttagtgg gttggccggg gccgcggtcg gcagcatcgg gctgggtagg     5880
gtcctcattg acatcttggc tggatatggg gcaggagtgg ctggagcgct cgtcgccttc    5940
```

```
aagatcatgt gcggggagaa gccgacagcc gaagacctag taaacctcct gccttcaata      6000
ctctgccctg gagccctagt agtcggggtc atatgcgccg cggttctacg gcgccatatc      6060
ggcccgggcg agggagccgt gcagtggatg aacaggctga tcgcgttcgc ctcccgaggc      6120
aatcatgtgt ctccgacaca ctacgtgccc gagaccgacg cgtcggccaa agtcacacag      6180
ctgctcagct ccctcacagt aacatccctt ttgaagaggc tccatacatg gatcggtgag      6240
gactactcca cgccctgcga tggcacatgg ctaagggcca tttgggactg ggtctgcacg      6300
gcactgacag acttcaaagc ctggctgcag gcaaaactcc tcccacaact ccccggagtg      6360
cccttcctct cgtgtcagag agggtacaag ggcgtatggc gtggggatgg agtaaattcc      6420
accaagtgtc cgtgcggagc gacgatatct ggccacgtga aaaacggaac catgaggatc      6480
gtcggcccga agctgtgcag caacacctgg cacggaacct tccccatcaa cgccacaaca      6540
acggggccca gtgtgcctgc tccggccccc aactacaagt ttgccttgtg gagggtaggc      6600
gctgcggact acgccgaggt gcgccgcgtg ggggactacc attacatcac ggggtgaca      6660 caggacaatc tgaagtgtcc ctgtcaggta ccatctccag agttcttcac ggagctggac      6720
ggcgtgagga ttcaccgcta cgcgccaccc tgcaaccccc tcctaaggga ggaggtctgc      6780
ttctccgtgg ggctgcactc ctttgtggtg gggtcccaac taccctgtga gccagaacct      6840
gatgtgaccg tcctaacgtc aatgctgtca gaccctgctc acatcacggc agagacggcc      6900
aagcgcaggc tagatcgagg gtctccgccc tctctagcta gctcctcggc cagccaactc      6960 tcggcccccct cccttaaggc tacttgcact acacaaggtc accatccaga cgcagacctc      7020
atagaggcta atctgctatg gagacagtgc atgggaggta acatcacgcg agtggaagcc      7080
gagaacaagg tcgtgatcct tgactccttt gagccgctta aggcggatga cgacgacaga      7140
gagatctctg tgtccgctga ctgctttagg aggggaccgg cgtttccccc cgccctgcca      7200
gtatgggcaa ggccggggta tgacccaccc ctcctggaga cttggaagca gcctgattat      7260 gaccccccc aggtgtcagg ttgcccgcta ccacctgcgg gtctcccacc tgtcccgcct      7320
ccacgtagga agaggaaacc ggtggtgcta tctgactcca acgtgtccca agtcctggcc      7380
gacttggcgc atgccaggtt caaggccgac acgcaatcca ttgaaggcca ggattctgcg      7440
gtgggcacca gtagccaacc cgactcaggg cctgaggaga agcgtgatga tgactcggac      7500
gcggcttcat attcttccat gcctccgctg gagggcgagc ctggggaccc tgaccttcg      7560 tcagggtcgt ggtcaactgt cagcgatgag gacagtgtgg tgtgctgctc catgtcatac      7620
tcctggaccg gggctctaat aactcccgt agccccgaag aggaaaagtt gccaatcaac      7680
cctttgagta actcgctgtt gcgataccat aacaaggtgt actgtacaac atcaaagagc      7740
gcctcacaga gggctaaaaa ggtaactttt gacaggacgc aagtgctcga cgcccattat      7800
gactcagtct taaaggacat caagctagcg gcttccaagg tcagcgcaag gctcctcacc      7860
ttggaggagg cgtgccagtt gactccaccc cattctgcaa gatccaagta tggattcggg      7920
gccaaggagg tccgcagctt gtccgggagg gccgttaacc acatcaagtc cgtgtggaag      7980
gacctcctgg aagacccaca aacaccaatt cccacaacca tcatggccaa aaatgaggtg      8040
ttctgcgtgg accccgccaa ggggggtaag aaaccagctc gcctcatcgt ttaccctgac      8100
ctcggcgtcc gggtctgcga gaaaatggcc ctctatgaca ttacacaaaa gcttcctcag      8160
gcggtaatgg gagcttccta tggcttccag tactcccctg cccaacgggt ggagtatctc      8220
ttgaaagcat gggcggaaaa gaaggacccc atgggttttt cgtatgatac ccgatgcttc      8280
gactcaaccg tcactgagag agacatcagg accgaggagt ccatatacca ggcctgctcc      8340
```

```
ctgcccgagg aggcccgcac tgccatacac tcgctgactg agagacttta cgtaggaggg    8400
cccatgttca acagcaaggg tcaaacctgc ggttacagac gttgccgcgc cagcggggtg    8460
ctaaccacta gcatgggtaa caccatcaca tgctatgtga agccctagc ggcctgcaag     8520 gctgcgggga tagttgcgcc cacaatgctg gtatgcggcg atgacctagt agtcatctca    8580
gaaagccagg ggactgagga ggacgagcgg aacctgagag ccttcacgga ggccatgacc    8640
aggtactctg cccctcctgg tgatccccc agaccggaat atgacctgga gctaataaca     8700
tcctgttcct caaatgtgtc tgtggcgttg ggcccgcggg gccgccgcag atactacctg    8760
accagagacc caaccactcc actcgcccgg gctgcctggg aaacagttag acactcccct    8820
atcaattcat ggctgggaaa catcatccag tatgctccaa ccatatgggt tcgcatggtc    8880
ctaatgacac acttcttctc cattctcatg gtccaagaca ccctggacca gaacctcaac    8940
tttgagatgt atggatcagt atactccgtg aatcctttgg accttccagc cataattgag    9000
aggttacacg gccttgacgc ctttctatg cacacatact ctcaccacga actgacgcgg     9060
gtggcttcag ccctcagaaa acttggggcg ccaccctca gggtgtggaa gagtcgggct     9120
cgcgcagtca gggcgtccct catctcccgt ggagggaaag cggccgtttg cggccgatat    9180
ctcttcaatt gggcggtgaa gaccaagctc aaactcactc cattgccgga ggcgcgccta    9240
ctggacttat ccagttggtt caccgtcggc gccggcgggg cggcatttt tcacagcgtg     9300 tcgcgcgccc gaccccgctc attactcttc ggcctactcc tactttccgt aggggtaggc    9360
ctcttcctac tccccgctcg gtagagcggc acacactagg tacactccat agctaactgt    9420 tcctttttt ttttttttt ttttttttt ttttttttt tttttctttt ttttttttt         9480 tccctctttc ttcccttctc atcttattct actttctttc ttggtggctc catcttagcc    9540
ctagtcacgg ctagctgtga aggtccgtg agccgcatga ctgcagagag tgccgtaact     9600
ggtctctctg cagatcatgt                                                9620
```

<210> SEQ ID NO 6
<211> LENGTH: 9641
<212> TYPE: DNA
<213> ORGANISM: Hepatitis C virus

<400> SEQUENCE: 6

```
gccagcccct taacggggcg acactccgcc attatcactc cctgtgagg aactactgtc      60 ttcacgcaga aagcgtctag ccatggcgtt agtatgagtg tcgtacagcc tccaggcccc    120
cccctcccgg gagagccata gtggtctgcg gaaccggtga gtacaccgga attgccagga    180
tgaccgggtc ctttccattg gatcaaaccc gctcaatgcc tggagatttg ggcgtgcccc    240
cgcaagactg ctagccgagt agcgttgggt tgcgaaaggc cttgtggtac tgcctgatag    300
ggtgcttgcg agtgccccgg gaggtctcgt agaccgtgca tcatgagcac acttccaaaa    360
ccccaaagaa aaaccaaaag aaacaccaac cgtcgcccaa tggacgtcaa gttcccgggt    420
ggcggtcaga tcgttggcgg agtttacttg ttgccgcgca ggggcccccg gttgggtgtg    480
cgcgcgacga ggaagacttc cgagcgatcc cagcccagag gcaggcgcca acctatacca    540
aaggcgcgcc agccccaggg caggcactgg gctcagcccg gatatccttg gccccttttat   600 gggaacgagg gctgtgggtg ggcaggttgg ctcctgtccc ccgcggctc ccggccacac     660 tggggcccca acgaccccg gcgtcgatcc cggaatttgg gtaaggtcat cgatacccta     720
acgtgtgggt tcgccgatct catggggtac attcccgtcg tgggcgcgcc tttgggcggc    780
```

```
gtcgcggctg cactcgcaca tggtgtgagg gcaatcgagg acgggatcaa ttatgcaaca      840
gggaatcttc ccggttgctc tttctctatc ttcctcttgg cactactctc gtgcctcaca      900
acgccagcgt cggctcttac ctacggtaac tccagtgggc tataccatct tacaaatgat      960
tgccccaact ccagcatcgt gctggaggcg gatgccatga tcttgcattt gcctggatgc     1020
ttgccttgtg tgagggtcaa taacaaccag tccatctgtt ggcatgctgt gtccccacc      1080 ctagccatac caaatgcttc cacacctgca acgggattcc gtaggcatgt ggaccttctt     1140
gcgggcgccg cagtggtttg ctcatccctg tacatcgggg atctgtgcgg ctccctcttt     1200
ttggcagggc aactatttac ctttcagccc cgccgtcact ggactgtgca agactgcaac     1260
tgctccattt atacaggcca cgtcaccggc cacaggatgg cttgggacat gatgatgaat     1320
tggtcaccca caaccactct ggtcctatct agtatcttga gggtacctga gatctgtgcg     1380
agtgtgatat ttggtggcca ttgggggata ctactagccg ttgcctactt tggtatggct     1440
ggcaactggc taaaagttct ggctgtcctg ttcttatttg caggggttga agcaaccacc     1500
atcatcggcc atcaagtagg ccgcactact ggtggcttag ccagtctctt ctccatcggt     1560
cccaggcaaa atctacaact catcaacacc aatggcagct ggcatataaa caggactgct     1620
ctgaactgca atgattccct ccagacgggg ttcataacgt cactctttta tgccaagaac     1680
gtcaactcct cgggctgccc agagcggatg gctgcgtgta agcccctcgc ggacttccgg     1740
caggggtggg gccaaataac ctacaaagtc aacatctcgg gcccctccga cgaccgtccc     1800
tactgttggc attacgctcc caggccatgt gacgtggtgt cggcccgcac ggtgtgcggc     1860
cccgtttact gcttcacgcc cagccctgtc gtagtaggaa ccactgacaa gctgggcatt     1920
cccacataca actgggggga gaatgagacg gatgtgttca tgttggaaag ccttcggcct     1980
cctactggag gatggtttgg gtgcacgtgg atgaactcta cgggctttac caagacctgt     2040
ggtgccccgc catgtcagat agtcccggga gattacaata gctctgccaa tgagcttttg     2100
tgccccaccg actgcttccg taaacatccg gaagctacat atcagcggtg tggatcggga     2160
ccctggatca cacctaggtg tctggtggat taccctaca ggctgtggca ctaccctgt      2220 actgtcaact tcaccttgca taaagtcagg atgttcgtgg gaggcattga gcatcggttt     2280
gacgccgcat gtaactggac cagaggcgag cggtgtgatc tacatgacag agacaggatt     2340
gaaatgagcc cgctgctttt ctcaactacg cagcttgcca tacttccctg ttcatttcc      2400 accatgccgg ccttgtcaac cggcctcatc cacctgcatc agaacatagt ggacgtgcag     2460
tacctctacg gagtctcctc gagcgttacc tcgtgggtgg tgaagtggga gtacattgtt     2520
ctggtgttcc tggttctggc agatgctcgg atttgtacat gtctctggtt aatgctgctc     2580
ataaccaacg ttgaagcagc agtggaaagg cttgtcgtcc tcaatgcggc tagcgccgcc     2640
ggcaccgccg gctggtggtg ggcggtgctc ttcctgtgct gtgcttggta cgtgaaaggc     2700
cgccttgtgc ctgcgtgtac ctacatggca ctgggaatgt ggccgttgct cctgacaatc     2760
ttggccctgc ctcgccgagc atacgctatg gacaatgagc aagcggcatc cctcggagct     2820
gttggtctct tggtgctcac catctttacc atcaccccca tgtacaagaa gctgttgacc     2880
tgctccattt ggtggaatca gtatttcctc gcccgagctg aggccatgat acacgagtgg     2940
gtgcccgacc tacggggttag gggcggtagg gaccccatca tcttacttac ctgcttgtta     3000
catccacagc tggggtttga ggtcaccaaa attctactag ccatcctggc ccctctatac     3060
atcctgcagt acagttttgct caaggtgcct tactttgtgc gcgcccacgt actcctgcgt     3120
gcttgcctgc ttgttcgtag gctagcaggg ggtaagtacg tgcaggcgtg ccttctgagg     3180
```

```
ttgggcgctt ggactggcac ctttgtctat gaccatctcg cccctctctc tgactgggct    3240
agcgacggac tgcgcgattt ggcagtcgca atcgagccgg tcattttctc tcccatggag    3300
aagaaaatca ttacctgggg tgcggatacc gccgcgtgtg gtgacatctt gagtggcctc    3360
ccggtgtcag cgaggttggg gaatttggtg ctactgggac ccgcggacga tatgcagcgc    3420
gggggttgga agcttttggc tcccatcacc gcgtatgcgc agcagacgag gggcctagtc    3480
ggcaccattg tgaccagcct aaccgggcgt gacaaaaatg aggtcgaagg ggaggtacag    3540
gtggtctcca cggctaccca gtccttccta gcgacctcca ttaacggtgt catgtggact    3600
gtttatcatg gggccggttc aaagactctc gctggaccga aaggaccagt gtgtcaaatg    3660
tacaccaatg tggacaagga cctagtagga tggccatctc ccccgggagc aaggtcgctc    3720 acccatgta catgtggctc tagtgacctt tatctggtca cgagggaggc cgacgttatc    3780
cccgcaaggc gcaggggtga caaccgtgcc gccctccttt ctcctaggcc cataagcacc    3840
ttgaaaggct cctcggggag ccccattatg tgcccttcgg ggcacgttgt gggactcttc    3900
cgagctgccg tatgcacaag gggtgtagca aagtccttag attttatccc agtggaaaac    3960
atggagacga ctatgcgctc tccttcattc acagacaact ccacgccgcc tgcagtgccc    4020
cagacctatc aggtagggta tctgcacgca ccaacaggca gcggaaagag cacccgtgtt    4080
ccggcggctt acgctagcca gggctacaag gtgttggtct tgaacccatc tgtggcggca    4140
acgcttagct ttggctctta tatgaggcaa gcttatggcg tggagccgaa tatccggacc    4200
ggggtcagga ctgtgactac aggggtgct attacgtact ccacatatgg gaaattcttg    4260
gccgatgggg ggtgctccgg aggagcgtat gacatcatca tctgtgatga gtgccactcc    4320 acagaccca cgacggtgtt gggcattggc acggttctcg accaggctga gactgccggg    4380
gtccgcctta ctgtgctcgc aacagcaacg ccgccaggct ctgtcactgt cccccatcct    4440
aacataacag agacagccct cccgactacg ggagaaatac cattttatgg aaagggcatc    4500
cccctcgagt acatcaaggg gggaagacat ctcatatttt gtcactcaaa aagaagtgt    4560 gatgagctgg ccgggaaact gaagtcactc ggcttaaacg ccgtcgcgtt ctacagaggt    4620
gtcgatgtgt ccgtcattcc cacctcgggc gatgtcgtcg tctgcgcaac ggacgccctt    4680
atgaccggct acacaggaga tttcgattcc gtcatcgact gtaacgtagc cgtgacacag    4740
gtggtggatc tcagcttgga cccaacattt tccatagaga ctaccatcgt ccctcaggat    4800
gcggtatcac ggagccaacg acgaggccgc acggggcggg gtaaaccggg ggtgtacaga    4860
tttgtctccc aaggggagag gccctcgggt atgttcgaca ccgtcgtcct gtgtgaggct    4920
tatgacacgg gatgtgcgtg gtacgaacta accccttctg aaacaactgt caggctgagg    4980
gcctatctga acactcctgg ccttcccta tgccaagacc acctggagtt ttgggaaggc    5040
gtatttactg gcttgactca catagacgcc cactttctgt ctcagacgaa gcagggggt    5100 gagaacttcg cgtacctcgt ggcataccag gccacagtgt gcgccagggc caaagccccc    5160
ccgccttctt gggatacgat gtggaagtgt ctcatcagac tcaaacccac ccttaccggc    5220
cccactccac tcttgtatcg gctgggggcc gtccaaaatg agataataac aacccatcca    5280
ataaccaaat acatcatgac ctgtatgtcc gcagatttgg aggtcatcac cagcacatgg    5340
gtcctcgtgg gtggagtcct cgctgcactc gcgtcctact gcttatcggt gggctgtgtt    5400
gtcatctgtg gcagggtaac tttgactggc aagcctgctg ttgtccctga tcgcgagatc    5460
ttataccagc agtttgacga gatggaggag tgctctaggc acatccccta cctcgctgag    5520
```

-continued

```
ggccagcaga tcgccgaaca gttcagacaa aaggtgttgg gactccttca ggcgagcgct    5580
aagcaggcag aagaactaaa gcctgctgtc catgccgcgt ggcctaggat ggaggagttt    5640
tggaggaaac acatgtggaa ctttgtcagc gggattcagt acttggcggg cttatccact    5700
ctgcccggca acccggcagt ggcatcgatg atgtcattta cagcgtcgct gaccagtcct    5760
ctgcggactt ctcagaccct gctcctcaac atactcggcg gctggatagc cacccaagtg    5820
gctcccccc ccgcgtccac agcttttgtc gtgagcggtc tggcgggagc cacggttgga    5880
agcattggac tcgggagggt gttggttgat gtgctcgccg atacggagc cggtgtgtcg     5940
ggtgctctag tcgcttttaa gatcatgagc ggcgagtgcc cgaccacgga agacatggtc    6000
aatctgctac ccgcgctgtt gtcgccaggg gctctcgtgg tggggtcgt gtgtgctgcc     6060
atcttaagac gccacgttgg ccctgctgag ggtgctaacc agtggatgaa caggctaata    6120
gcctttgcat caagaggcaa ccacgtgtcc ccgacgcatt acgtgcctga aactgacgcg    6180
tcaaagaatg tgactcagat actcacttct cttaccatca ccagtctact ccgtagatta    6240
catcagtggg tcaatgaaga cacggccacc ccttgcgcta cctcatggtt gcgcgacgtg    6300
tgggactggg tgtgtacagt gttatctgat tttagagtat ggctgaaagc caaactcctc    6360
ccacgcctgc cggggatccc cttcctctcg tgccaaacgg gatataggg agtctgggca    6420
ggggacgggg tgtgccacac cacttgtacc tgtggggccg tgatagctgg acacgtcaaa    6480
aatggcacca tgaaaatcac agggcccaag acatgcagta acacttggca cgggactttt    6540
ccaatcaacg ccaccactac cggccccagc acaccgcgac cagcgccgaa ctatcagcgc    6600
gctctttggc gggtatctgc cgaggactac gttgaagtac ggaggttggg cgactgccac    6660
tatgtggtag gggtcactgc tgaagggctg aagtgccctt gccaggtgcc tgcgcctgaa    6720
ttcttcactg aggtcgatgg cgtgaggata caccgttacg cgccaccttg taagcccttg    6780
ctcagggacg aagtgacatt ctctgtgggt cttttcaagct atgccatagg gtctcagctc    6840
ccttgtgagc cagagcctga cgtgaccgta gtcacctcaa tgctcacaga ccccacgcac    6900
atcaccgcag agacggcagc acggcggttg aagagggggt ccccccctc cttagccagc     6960
tcttcggcca gccagctgtc tgcaccgtcc ctcaaggcta cttgcacaac acccaaagac    7020
caccgggaca tggaactcat tgaggccaac ctccttttgga ggcaggagat gggaggcaac    7080
atcactcggg tcgagtcgga gaacaaagtt gtaatacttg actcctttga gcctttaacc    7140
gctgagtatg acgagaggga aatctcagta tcagctgagt gccataggcc acctaggcgc    7200
aaattccctc cagctctccc aatatgggcc aggcctgact acaatccacc tcttatacaa    7260
gcatggcaaa tgcccgggta cgagcctcca gtcgtgtctg gatgcgccgt cgccccacct    7320
aagccggcac caattccccc gccgaggcgg aagaggctag tgcacttgga tgagtccacg    7380
gtctcgcacg ccttggcaca gcttgccgac aaggtatttg tggagagtag tagtgaccca    7440
ggacctagtt cagactcggg actatcaata gccagtcccg ttccacctgc cccaacaaca    7500
ccagacgacg cctgctcaga agcagggtcc tatagctcaa tgccccctct tgaggggag    7560
cctggtgacc ctgacctaag ctcaggttct tggtccactg tgagcgatca ggacgacgtc    7620
gtgtgttgct ccatgtcata ctcctggacc ggggctctaa taactccctg tagccccgaa    7680
gaggaaaagt tgccaatcaa ccctttgagt aactcgctgt tgcgatacca taacaaggtg    7740
tactgtacaa catcaaagag cgcctcacag agggctaaaa aggtaacttt tgacaggacg    7800
caagtgctcg acgcccatta tgactcagtc ttaaaggaca tcaagctagc ggcttccaag    7860
gtcagcgcaa ggctcctcac cttggaggag gcgtgccagt tgactccacc ccattctgca    7920
```

-continued

```
agatccaagt atggattcgg ggccaaggag gtccgcagct tgtccggagg ggccgttaac    7980
cacatcaagt ccgtgtggaa ggacctcctg aagacccac aaacaccaat cccacaacc     8040 atcatggcca aaaatgaggt gttctgcgtg accccgcca agggggtaa gaaaccagct    8100 cgcctcatcg tttaccctga cctcggcgtc cgggtctgcg agaaaatggc cctctatgac    8160
attacacaaa agcttcctca ggcggtaatg ggagcttcct atggcttcca gtactcccct    8220
gcccaacggg tggagtatct cttgaaagca tgggcgaaaa agaaggaccc catgggtttt    8280
tcgtatgata cccgatgctt cgactcaacc gtcactgaga gagacatcag gaccgaggag    8340
tccatatacc aggcctgctc cctgcccgag gaggcccgca ctgccataca ctcgctgact    8400
gagagacttt acgtaggagg gcccatgttc aacagcaagg tcaaacctg cggttacaga    8460 cgttgccgcg ccagcggggt gctaaccact agcatgggta acaccatcac atgctatgtg    8520
aaagccctag cggcctgcaa ggctgcgggg atagttgcgc ccacaatgct ggtatgcggc    8580
gatgacctag tagtcatctc agaaaagcca gggactgagg aggacgagcg gaacctgaga    8640
gccttcacgg aggccatgac caggtactct gcccctcctg gtgatccccc cagaccggaa    8700
tatgacctga gctaataac atcctgttcc tcaaatgtgt ctgtggcgtt gggcccgcgg    8760
ggccgccgca gatactacct gaccagagac ccaaccactc cactcgcccg ggctgcctgg    8820
gaaacagtta gacactcccc tatcaattca tggctgggaa acatcatcca gtatgctcca    8880
accatatggg ttcgcatggt cctaatgaca cacttcttct ccattctcat ggtccaagac    8940
accctggacc agaaccctcaa ctttgagatg tatggatcag tatactccgt gaatcctttg    9000
gaccttccag ccataattga gaggttacac gggcttgacg ccttttctat gcacacatac    9060
tctcaccacg aactgacgcg ggtggcttca gccctcagaa aacttggggc gccaccctc    9120 agggtgtgga agagtcgggc tcgcgcagtc agggcgtccc tcatctcccg tggagggaaa    9180
gcggccgttt gcggccgata tctcttcaat tgggcggtga agaccaagct caaactcact    9240
ccattgccgg aggcgcgcct actggactta tccagttggt tcaccgtcgg cgccggcggg    9300
ggcggcattt ttcacagcgt gtcgcgcgcc cgaccccgct cattactctt cggcctactc    9360 ctactttcg taggggtagg cctcttccta ctccccgctc ggtagagcgg cacacactag    9420
gtacactcca tagctaactg ttccttttttt tttttttttt ttttttttt ttttttttt    9480 ttttttcttt ttttttttt ttccctcttt cttcccttct catcttattc tactttcttt    9540
cttggtggct ccatcttagc cctagtcacg gctagctgtg aaaggtccgt gagccgcatg    9600
actgcagaga gtgccgtaac tggtctctct gcagatcatg t                      9641
```

<210> SEQ ID NO 7
<211> LENGTH: 3011
<212> TYPE: PRT
<213> ORGANISM: Hepatitis C virus

<400> SEQUENCE: 7

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

```
Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
```

```
            485                 490                 495
Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
            530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
                580                 585                 590

Thr Tyr Ser Arg Cys Gly Ser Gly Pro Trp Ile Thr Pro Arg Cys Met
                595                 600                 605

Val Asp Tyr Pro Tyr Arg Leu Trp His Tyr Pro Cys Thr Ile Asn Tyr
            610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
                660                 665                 670

Gln Val Leu Pro Cys Ser Phe Thr Thr Leu Pro Ala Leu Ser Thr Gly
                675                 680                 685

Leu Ile His Leu His Gln Asn Ile Val Asp Val Gln Tyr Leu Tyr Gly
            690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
                740                 745                 750

Ile Leu Asn Ala Ala Ser Leu Ala Gly Thr His Gly Leu Val Ser Phe
                755                 760                 765

Leu Val Phe Phe Cys Phe Ala Trp Tyr Leu Lys Gly Arg Trp Val Pro
            770                 775                 780

Gly Ala Val Tyr Ala Leu Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
                820                 825                 830

Pro Tyr Tyr Lys Arg Tyr Ile Ser Trp Cys Met Trp Trp Leu Gln Tyr
            835                 840                 845

Phe Leu Thr Arg Val Glu Ala Gln Leu His Val Trp Val Pro Pro Leu
850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910
```

```
Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
        930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
            995                 1000                1005

Glu Ile  Leu Leu Gly Pro Ala  Asp Gly Met Val Ser  Lys Gly Trp
    1010                1015                1020

Arg Leu  Leu Ala Pro Ile Thr  Ala Tyr Ala Gln Gln  Thr Arg Gly
    1025                1030                1035

Leu Leu  Gly Cys Ile Ile Thr  Ser Leu Thr Gly Arg  Asp Lys Asn
    1040                1045                1050

Gln Val  Glu Gly Glu Val Gln  Ile Val Ser Thr Ala  Thr Gln Thr
    1055                1060                1065

Phe Leu  Ala Thr Cys Ile Asn  Gly Val Cys Trp Thr  Val Tyr His
    1070                1075                1080

Gly Ala  Gly Thr Arg Thr Ile  Ala Ser Pro Lys Gly  Pro Val Ile
    1085                1090                1095

Gln Met  Tyr Thr Asn Val Asp  Gln Asp Leu Val Gly  Trp Pro Ala
    1100                1105                1110

Pro Gln  Gly Ser Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Leu Phe  Arg Ala Ala Val Cys  Thr Arg Gly
    1175                1180                1185

Val Ala  Lys Ala Val Asp Phe  Ile Pro Val Glu Asn  Leu Gly Thr
    1190                1195                1200

Thr Met  Arg Ser Pro Val Phe  Thr Asp Asn Ser Ser  Pro Pro Ala
    1205                1210                1215

Val Pro  Gln Ser Phe Gln Val  Gly His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260

Phe Gly  Ala Tyr Met Ser Lys  Ala His Gly Val Asp  Pro Asn Ile
    1265                1270                1275

Arg Thr  Gly Val Arg Thr Ile  Thr Thr Gly Ser Pro  Ile Thr Tyr
    1280                1285                1290

Ser Thr  Tyr Gly Lys Phe Leu  Ala Asp Gly Gly Cys  Ser Gly Gly
    1295                1300                1305
```

-continued

Ala Tyr Asp Ile Ile Ile Cys Asp Glu Cys His Ser Thr Asp Ala
1310             1315                 1320

Thr Ser Ile Leu Gly Ile Gly Thr Val Leu Asp Gln Ala Glu Thr
1325             1330                 1335

Ala Gly Ala Arg Leu Val Val Leu Ala Thr Ala Thr Pro Pro Gly
1340             1345                 1350

Ser Val Thr Val Ser His Pro Asn Ile Glu Glu Val Ala Leu Ser
1355             1360                 1365

Thr Thr Gly Glu Ile Pro Phe Tyr Gly Lys Ala Ile Pro Leu Glu
1370             1375                 1380

Val Ile Lys Gly Gly Arg His Leu Ile Phe Cys His Ser Lys Lys
1385             1390                 1395

Lys Cys Asp Glu Leu Ala Ala Lys Leu Val Ala Leu Gly Ile Asn
1400             1405                 1410

Ala Val Ala Tyr Tyr Arg Gly Leu Asp Val Ser Val Ile Pro Thr
1415             1420                 1425

Ser Gly Asp Val Val Val Ser Thr Asp Ala Leu Met Thr Gly
1430             1435                 1440

Phe Thr Gly Asp Phe Asp Ser Val Ile Asp Cys Asn Thr Cys Val
1445             1450                 1455

Thr Gln Thr Val Asp Leu Ser Leu Asp Pro Thr Phe Thr Ile Glu
1460             1465                 1470

Thr Thr Thr Leu Pro Gln Asp Ala Val Ser Arg Thr Gln Arg Arg
1475             1480                 1485

Gly Arg Thr Gly Arg Gly Lys Pro Gly Ile Tyr Arg Phe Val Ala
1490             1495                 1500

Pro Gly Glu Arg Pro Ser Gly Met Phe Asp Ser Ser Val Leu Cys
1505             1510                 1515

Glu Cys Tyr Asp Ala Gly Cys Ala Trp Tyr Glu Leu Thr Pro Ala
1520             1525                 1530

Glu Thr Thr Val Arg Leu Arg Ala Tyr Met Asn Thr Pro Gly Leu
1535             1540                 1545

Pro Val Cys Gln Asp His Leu Glu Phe Trp Glu Gly Val Phe Thr
1550             1555                 1560

Gly Leu Thr His Ile Asp Ala His Phe Leu Ser Gln Thr Lys Gln
1565             1570                 1575

Ser Gly Glu Asn Phe Pro Tyr Leu Val Ala Tyr Gln Ala Thr Val
1580             1585                 1590

Cys Ala Arg Ala Gln Ala Pro Pro Pro Ser Trp Asp Gln Met Trp
1595             1600                 1605

Lys Cys Leu Ile Arg Leu Lys Pro Thr Leu His Gly Pro Thr Pro
1610             1615                 1620

Leu Leu Tyr Arg Leu Gly Ala Val Gln Asn Glu Val Thr Leu Thr
1625             1630                 1635

His Pro Ile Thr Lys Tyr Ile Met Thr Cys Met Ser Ala Asp Leu
1640             1645                 1650

Glu Val Val Thr Ser Thr Trp Val Leu Val Gly Gly Val Leu Ala
1655             1660                 1665

Ala Leu Ala Ser Tyr Cys Leu Ser Thr Gly Cys Val Val Ile Val
1670             1675                 1680

Gly Arg Ile Val Leu Ser Gly Lys Pro Ala Ile Ile Pro Asp Arg
1685             1690                 1695

Glu Val Leu Tyr Gln Glu Phe Asp Glu Met Glu Glu Cys Ser Gln

-continued

```
            1700                1705                1710
His Leu Pro Tyr Ile Glu Gln Gly Met Met Leu Ala Glu Gln Phe
    1715                1720                1725
Lys Gln Lys Ala Leu Gly Leu Leu Gln Thr Ala Ser Arg His Ala
    1730                1735                1740
Glu Val Ile Thr Pro Ala Val Gln Thr Asn Trp Gln Lys Leu Glu
    1745                1750                1755
Val Phe Trp Ala Lys His Met Trp Asn Phe Ile Ser Gly Ile His
    1760                1765                1770
Tyr Leu Ala Gly Leu Ser Thr Leu Pro Gly Asn Pro Ala Ile Ala
    1775                1780                1785
Ser Leu Met Ala Phe Thr Ala Ala Val Thr Ser Pro Leu Thr Thr
    1790                1795                1800
Gly Gln Thr Leu Leu Phe Asn Ile Leu Gly Gly Trp Val Ala Ala
    1805                1810                1815
Gln Leu Ala Ala Pro Gly Ala Ala Thr Ala Phe Val Gly Ala Gly
    1820                1825                1830
Leu Ala Gly Ala Ala Ile Gly Ser Val Gly Leu Gly Lys Val Leu
    1835                1840                1845
Val Asp Ile Leu Ala Gly Tyr Gly Ala Gly Val Ala Gly Ala Leu
    1850                1855                1860
Val Ala Phe Lys Ile Met Ser Gly Glu Val Pro Ser Thr Glu Asp
    1865                1870                1875
Leu Val Asn Leu Leu Pro Ala Ile Leu Ser Pro Gly Ala Leu Val
    1880                1885                1890
Val Gly Val Val Cys Ala Ala Ile Leu Arg Arg His Val Gly Pro
    1895                1900                1905
Gly Glu Gly Ala Val Gln Trp Met Asn Arg Leu Ile Ala Phe Ala
    1910                1915                1920
Ser Arg Gly Asn His Val Ser Pro Thr His Tyr Val Pro Glu Ser
    1925                1930                1935
Asp Ala Ala Ala Arg Val Thr Ala Ile Leu Ser Ser Leu Thr Val
    1940                1945                1950
Thr Gln Leu Leu Arg Arg Leu His Gln Trp Ile Ser Ser Glu Cys
    1955                1960                1965
Thr Thr Pro Cys Ser Gly Ser Trp Leu Arg Asp Ile Trp Asp Trp
    1970                1975                1980
Ile Cys Glu Val Leu Ser Asp Phe Lys Thr Trp Leu Lys Ala Lys
    1985                1990                1995
Leu Met Pro Gln Leu Pro Gly Ile Pro Phe Val Ser Cys Gln Arg
    2000                2005                2010
Gly Tyr Arg Gly Val Trp Arg Gly Asp Gly Ile Met His Thr Arg
    2015                2020                2025
Cys His Cys Gly Ala Glu Ile Thr Gly His Val Lys Asn Gly Thr
    2030                2035                2040
Met Arg Ile Val Gly Pro Arg Thr Cys Arg Asn Met Trp Ser Gly
    2045                2050                2055
Thr Phe Pro Ile Asn Ala Tyr Thr Thr Gly Pro Cys Thr Pro Leu
    2060                2065                2070
Pro Ala Pro Asn Tyr Lys Phe Ala Leu Trp Arg Val Ser Ala Glu
    2075                2080                2085
Glu Tyr Val Glu Ile Arg Arg Val Gly Asp Phe His Tyr Val Ser
    2090                2095                2100
```

-continued

```
Gly Met Thr Thr Asp Asn Leu Lys Cys Pro Cys Gln Ile Pro Ser
    2105            2110            2115

Pro Glu Phe Phe Thr Glu Leu Asp Gly Val Arg Leu His Arg Phe
    2120            2125            2130

Ala Pro Pro Cys Lys Pro Leu Leu Arg Glu Glu Val Ser Phe Arg
    2135            2140            2145

Val Gly Leu His Glu Tyr Pro Val Gly Ser Gln Leu Pro Cys Glu
    2150            2155            2160

Pro Glu Pro Asp Val Ala Val Leu Thr Ser Met Leu Thr Asp Pro
    2165            2170            2175

Ser His Ile Thr Ala Glu Ala Gly Arg Arg Leu Ala Arg Gly
    2180            2185            2190

Ser Pro Pro Ser Met Ala Ser Ser Ser Ala Ser Gln Leu Ser Ala
    2195            2200            2205

Pro Ser Leu Lys Ala Thr Cys Thr Ala Asn His Asp Ser Pro Asp
    2210            2215            2220

Ala Glu Leu Ile Glu Ala Asn Leu Leu Trp Arg Gln Glu Met Gly
    2225            2230            2235

Gly Asn Ile Thr Arg Val Glu Ser Glu Asn Lys Val Val Ile Leu
    2240            2245            2250

Asp Ser Phe Asp Pro Leu Val Ala Glu Glu Asp Glu Arg Glu Val
    2255            2260            2265

Ser Val Pro Ala Glu Ile Leu Arg Lys Ser Arg Arg Phe Ala Arg
    2270            2275            2280

Ala Leu Pro Val Trp Ala Arg Pro Asp Tyr Asn Pro Pro Leu Val
    2285            2290            2295

Glu Thr Trp Lys Lys Pro Asp Tyr Glu Pro Pro Val Val His Gly
    2300            2305            2310

Cys Pro Leu Pro Pro Pro Arg Ser Pro Pro Val Pro Pro Pro Arg
    2315            2320            2325

Lys Lys Arg Thr Val Val Leu Thr Glu Ser Thr Leu Ser Thr Ala
    2330            2335            2340

Leu Ala Glu Leu Ala Thr Lys Ser Phe Gly Ser Ser Ser Thr Ser
    2345            2350            2355

Gly Ile Thr Gly Asp Asn Thr Thr Thr Ser Ser Glu Pro Ala Pro
    2360            2365            2370

Ser Gly Cys Pro Pro Asp Ser Asp Val Glu Ser Tyr Ser Ser Met
    2375            2380            2385

Pro Pro Leu Glu Gly Glu Pro Gly Asp Pro Asp Leu Ser Asp Gly
    2390            2395            2400

Ser Trp Ser Thr Val Ser Ser Gly Ala Asp Thr Glu Asp Val Val
    2405            2410            2415

Cys Cys Ser Met Ser Tyr Ser Trp Thr Gly Ala Leu Ile Thr Pro
    2420            2425            2430

Cys Ser Pro Glu Glu Glu Lys Leu Pro Ile Asn Pro Leu Ser Asn
    2435            2440            2445

Ser Leu Leu Arg Tyr His Asn Lys Val Tyr Cys Thr Thr Ser Lys
    2450            2455            2460

Ser Ala Ser Gln Arg Ala Lys Lys Val Thr Phe Asp Arg Thr Gln
    2465            2470            2475

Val Leu Asp Ala His Tyr Asp Ser Val Leu Lys Asp Ile Lys Leu
    2480            2485            2490
```

```
Ala Ala Ser Lys Val Ser Ala Arg Leu Leu Thr Leu Glu Glu Ala
        2495                2500                2505

Cys Gln Leu Thr Pro Pro His Ser Ala Arg Ser Lys Tyr Gly Phe
    2510                2515                2520

Gly Ala Lys Glu Val Arg Ser Leu Ser Gly Arg Ala Val Asn His
    2525                2530                2535

Ile Lys Ser Val Trp Lys Asp Leu Leu Glu Asp Pro Gln Thr Pro
    2540                2545                2550

Ile Pro Thr Thr Ile Met Ala Lys Asn Glu Val Phe Cys Val Asp
    2555                2560                2565

Pro Ala Lys Gly Gly Lys Lys Pro Ala Arg Leu Ile Val Tyr Pro
    2570                2575                2580

Asp Leu Gly Val Arg Val Cys Glu Lys Met Ala Leu Tyr Asp Ile
    2585                2590                2595

Thr Gln Lys Leu Pro Gln Ala Val Met Gly Ala Ser Tyr Gly Phe
    2600                2605                2610

Gln Tyr Ser Pro Ala Gln Arg Val Glu Tyr Leu Leu Lys Ala Trp
    2615                2620                2625

Ala Glu Lys Lys Asp Pro Met Gly Phe Ser Tyr Asp Thr Arg Cys
    2630                2635                2640

Phe Asp Ser Thr Val Thr Glu Arg Asp Ile Arg Thr Glu Glu Ser
    2645                2650                2655

Ile Tyr Gln Ala Cys Ser Leu Pro Glu Glu Ala Arg Thr Ala Ile
    2660                2665                2670

His Ser Leu Thr Glu Arg Leu Tyr Val Gly Gly Pro Met Phe Asn
    2675                2680                2685

Ser Lys Gly Gln Thr Cys Gly Tyr Arg Arg Cys Arg Ala Ser Gly
    2690                2695                2700

Val Leu Thr Thr Ser Met Gly Asn Thr Ile Thr Cys Tyr Val Lys
    2705                2710                2715

Ala Leu Ala Ala Cys Lys Ala Ala Gly Ile Val Ala Pro Thr Met
    2720                2725                2730

Leu Val Cys Gly Asp Asp Leu Val Val Ile Ser Glu Ser Gln Gly
    2735                2740                2745

Thr Glu Glu Asp Glu Arg Asn Leu Arg Ala Phe Thr Glu Ala Met
    2750                2755                2760

Thr Arg Tyr Ser Ala Pro Pro Gly Asp Pro Pro Arg Pro Glu Tyr
    2765                2770                2775

Asp Leu Glu Leu Ile Thr Ser Cys Ser Ser Asn Val Ser Val Ala
    2780                2785                2790

Leu Gly Pro Arg Gly Arg Arg Tyr Tyr Leu Thr Arg Asp Pro
    2795                2800                2805

Thr Thr Pro Leu Ala Arg Ala Ala Trp Glu Thr Val Arg His Ser
    2810                2815                2820

Pro Ile Asn Ser Trp Leu Gly Asn Ile Ile Gln Tyr Ala Pro Thr
    2825                2830                2835

Ile Trp Val Arg Met Val Leu Met Thr His Phe Phe Ser Ile Leu
    2840                2845                2850

Met Val Gln Asp Thr Leu Asp Gln Asn Leu Asn Phe Glu Met Tyr
    2855                2860                2865

Gly Ser Val Tyr Ser Val Asn Pro Leu Asp Leu Pro Ala Ile Ile
    2870                2875                2880

Glu Arg Leu His Gly Leu Asp Ala Phe Ser Met His Thr Tyr Ser
```

-continued

```
                2885                2890                2895
His His Glu Leu Thr Arg Val Ala Ser Ala Leu Arg Lys Leu Gly
    2900                2905                2910

Ala Pro Pro Leu Arg Val Trp Lys Ser Arg Ala Arg Ala Val Arg
    2915                2920                2925

Ala Ser Leu Ile Ser Arg Gly Gly Lys Ala Ala Val Cys Gly Arg
    2930                2935                2940

Tyr Leu Phe Asn Trp Ala Val Lys Thr Lys Leu Lys Leu Thr Pro
    2945                2950                2955

Leu Pro Glu Ala Arg Leu Leu Asp Leu Ser Ser Trp Phe Thr Val
    2960                2965                2970

Gly Ala Gly Gly Gly Gly Ile Phe His Ser Val Ser Arg Ala Arg
    2975                2980                2985

Pro Arg Ser Leu Leu Phe Gly Leu Leu Leu Leu Phe Val Gly Val
    2990                2995                3000

Gly Leu Phe Leu Leu Pro Ala Arg
    3005                3010

<210> SEQ ID NO 8
<211> LENGTH: 3011
<212> TYPE: PRT
<213> ORGANISM: Hepatitis C virus

<400> SEQUENCE: 8

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Gly Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Phe Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240
```

```
Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
        260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
        290                 295                 300

Asn Cys Ser Ile Tyr Pro Gly His Ile Ser His Arg Met Ala Trp
305             310                 315                 320

Asp Met Met Met Asn Trp Ser Pro Thr Ala Ala Leu Leu Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Met Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr Tyr Val Thr Gly Gly Ser Ala Ala Arg Thr Thr Ala Gly Leu Ala
385                 390                 395                 400

Ser Leu Phe Ser Pro Gly Ala Lys Gln Asn Ile Gln Leu Val Asn Thr
                405                 410                 415

Asn Gly Ser Trp His Ile Asn Ser Thr Ala Leu Asn Cys Asn Asp Ser
            420                 425                 430

Leu Asn Thr Gly Trp Ile Ala Gly Leu Phe Tyr His His Lys Phe Asn
        435                 440                 445

Ser Ser Gly Cys Ser Glu Arg Leu Ala Ser Cys Arg Pro Leu Thr Asp
    450                 455                 460

Phe Ala Gln Gly Trp Gly Pro Ile Ser His Ala Asp Gly Ser Gly Pro
465                 470                 475                 480

Asp Gln Arg Pro Tyr Cys Trp His Tyr Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Arg Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Val Phe Lys Val Arg Met Tyr Val Gly Gly Val Glu His Arg Leu
625                 630                 635                 640

Glu Ala Ala Cys Asn Trp Thr Arg Gly Asp Arg Cys Asn Leu Asp Asp
                645                 650                 655

Arg Asp Arg Ser Glu Leu Ser Pro Leu Leu Leu Ser Thr Thr Gln Trp
```

-continued

```
                660                 665                 670
Gln Val Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Val Glu Ala Ala Leu Glu Asn Leu Val
            740                 745                 750

Val Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Ala Leu Tyr Gly Met Trp Pro Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
        835                 840                 845

Phe Leu Thr Arg Ile Glu Ala Gln Leu His Val Trp Ile Pro Pro Leu
    850                 855                 860

Asn Val Arg Gly Gly Arg Asp Ala Val Ile Leu Leu Met Cys Val Val
865                 870                 875                 880

His Pro Ala Leu Val Phe Asp Ile Thr Lys Leu Leu Leu Ala Ala Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Met
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
        995                 1000                1005

Glu Ile Leu Leu Gly Pro Ala Asp Gly Met Val Ser Lys Gly Trp
    1010                1015                1020

Arg Leu Leu Ala Pro Ile Thr Ala Tyr Ala Gln Gln Thr Arg Gly
    1025                1030                1035

Leu Leu Gly Cys Ile Ile Thr Ser Leu Thr Gly Arg Asp Lys Asn
    1040                1045                1050

Gln Val Glu Gly Glu Ile Gln Ile Val Ser Thr Ala Ala Gln Thr
    1055                1060                1065

Phe Leu Ala Thr Cys Ile Asn Gly Val Cys Trp Thr Val Tyr His
    1070                1075                1080
```

-continued

```
Gly Ala Gly Thr Arg Thr Ile Ala Ser Pro Lys Gly Pro Val Ile
1085                1090                1095

Gln Met Tyr Thr Asn Val Asp Lys Asp Leu Val Gly Trp Pro Ala
    1100                1105                1110

Pro Gln Gly Ala Arg Ser Leu Thr Pro Cys Thr Cys Gly Ser Ser
    1115                1120                1125

Asp Leu Tyr Leu Val Thr Arg His Ala Asp Val Ile Pro Val Arg
    1130                1135                1140

Arg Arg Gly Asp Ser Arg Gly Ser Leu Leu Ser Pro Arg Pro Ile
    1145                1150                1155

Ser Tyr Leu Lys Gly Ser Ser Gly Gly Pro Leu Leu Cys Pro Ala
    1160                1165                1170

Gly His Ala Val Gly Leu Phe Arg Ala Ala Val Cys Thr Arg Gly
    1175                1180                1185

Val Ala Lys Ala Val Asp Phe Ile Pro Val Glu Asn Leu Glu Thr
    1190                1195                1200

Thr Met Arg Ser Pro Val Phe Thr Asp Asn Ser Ser Pro Pro Ala
    1205                1210                1215

Val Pro Gln Ser Phe Gln Val Gly His Leu His Ala Pro Thr Gly
    1220                1225                1230

Ser Gly Lys Ser Thr Lys Val Pro Ala Ala Tyr Ala Ala Gln Gly
    1235                1240                1245

Tyr Lys Val Leu Val Leu Asn Pro Ser Val Ala Ala Thr Leu Gly
    1250                1255                1260

Phe Gly Ala Tyr Met Ser Lys Ala His Gly Val Asp Pro Asn Ile
    1265                1270                1275

Arg Thr Gly Val Arg Thr Ile Thr Thr Gly Ser Pro Ile Thr Tyr
    1280                1285                1290

Ser Thr Tyr Gly Lys Phe Leu Ala Asp Gly Gly Cys Ser Gly Gly
    1295                1300                1305

Ala Tyr Asp Ile Ile Ile Cys Asp Glu Cys His Ser Thr Asp Ala
    1310                1315                1320

Thr Ser Ile Leu Gly Ile Gly Thr Val Leu Asp Gln Ala Glu Thr
    1325                1330                1335

Ala Gly Ala Arg Leu Val Val Leu Ala Thr Ala Thr Pro Pro Gly
    1340                1345                1350

Ser Ile Thr Val Pro His Pro Asn Ile Glu Glu Val Ala Leu Ser
    1355                1360                1365

Thr Thr Gly Glu Ile Pro Phe Tyr Gly Lys Ala Ile Pro Leu Glu
    1370                1375                1380

Ala Ile Lys Gly Gly Arg His Leu Ile Phe Cys His Ser Lys Lys
    1385                1390                1395

Lys Cys Asp Glu Leu Ala Ala Lys Leu Val Ala Leu Gly Ile Asn
    1400                1405                1410

Ala Val Ala Tyr Tyr Arg Gly Leu Asp Val Ser Val Ile Pro Thr
    1415                1420                1425

Ser Gly Asp Val Val Val Ala Thr Asp Ala Leu Met Thr Gly
    1430                1435                1440

Tyr Thr Gly Asp Phe Asp Ser Val Ile Asp Cys Asn Thr Cys Val
    1445                1450                1455

Thr Gln Thr Val Asp Leu Ser Leu Asp Pro Thr Phe Thr Ile Glu
    1460                1465                1470
```

```
Thr Thr Thr Leu Pro Gln Asp  Ala Val Ser Arg  Thr Gln Arg Arg
1475              1480                1485

Gly Arg Thr Gly Arg Gly Lys  Pro Gly Ile Tyr  Arg Phe Val Ala
1490              1495                1500

Leu Gly Glu Arg Pro Ser Gly  Met Phe Asp Ser  Ser Val Leu Cys
1505              1510                1515

Glu Cys Tyr Asp Ala Gly Cys  Ala Trp Tyr Glu  Leu Thr Pro Ala
1520              1525                1530

Glu Thr Val Arg Leu Arg Ala  Tyr Met Asn Thr  Pro Gly Leu
1535              1540                1545

Pro Val Cys Gln Asp His Leu  Glu Phe Trp Glu  Gly Val Phe Thr
1550              1555                1560

Gly Leu Thr His Ile Asp Ala  His Phe Leu Ser  Gln Thr Lys Gln
1565              1570                1575

Ser Gly Glu Asn Phe Pro Tyr  Leu Val Ala Tyr  Gln Ala Thr Val
1580              1585                1590

Cys Ala Arg Ala Gln Ala Pro  Pro Pro Ser Trp  Asp Gln Met Trp
1595              1600                1605

Lys Cys Leu Thr Arg Leu Lys  Pro Thr Leu His  Gly Pro Thr Pro
1610              1615                1620

Leu Leu Tyr Arg Leu Gly Ala  Val Gln Asn Glu  Val Thr Leu Thr
1625              1630                1635

His Pro Ile Thr Lys Tyr Ile  Met Thr Cys Met  Ser Ala Asp Leu
1640              1645                1650

Glu Val Val Thr Ser Thr Trp  Val Leu Val Gly  Gly Val Leu Ala
1655              1660                1665

Ala Leu Ala Ser Tyr Cys Leu  Ser Thr Gly Cys  Val Val Ile Val
1670              1675                1680

Gly Arg Ile Val Leu Ser Gly  Lys Pro Ala Ile  Ile Pro Asp Arg
1685              1690                1695

Glu Val Leu Tyr Arg Glu Phe  Asp Glu Met Glu  Glu Cys Ser Gln
1700              1705                1710

His Leu Pro Tyr Ile Glu Gln  Gly Met Met Leu  Ala Glu Gln Phe
1715              1720                1725

Lys Gln Lys Ala Leu Gly Leu  Leu Gln Thr Ala  Ser Arg Gln Ala
1730              1735                1740

Glu Val Val Ala Pro Ala Val  Gln Thr Asn Trp  Gln Lys Leu Glu
1745              1750                1755

Ala Phe Trp Ala Lys His Met  Trp Asn Phe Ile  Ser Gly Ile His
1760              1765                1770

Tyr Leu Ala Gly Leu Ser Thr  Leu Pro Gly Asn  Pro Ala Ile Ala
1775              1780                1785

Ser Leu Met Ala Phe Thr Ala  Ala Val Thr Ser  Pro Leu Thr Thr
1790              1795                1800

Ser Gln Thr Leu Leu Phe Asn  Ile Leu Gly Gly  Trp Val Ala Ala
1805              1810                1815

Gln Leu Ala Ala Pro Gly Ala  Ala Thr Ala Phe  Val Gly Ala Gly
1820              1825                1830

Leu Ala Gly Ala Ala Ile Gly  Ser Val Gly Leu  Gly Lys Val Leu
1835              1840                1845

Val Asp Ile Leu Ala Gly Tyr  Gly Ala Gly Val  Ala Gly Ala Leu
1850              1855                1860

Val Ala Phe Lys Ile Met Ser  Gly Glu Val Pro  Ser Thr Glu Asp
```

-continued

```
            1865                1870                1875
Leu Val Asn Leu Leu Pro Ala Ile Leu Ser Pro Gly Ala Leu Val
            1880                1885                1890
Val Gly Val Val Cys Ala Ala Ile Leu Arg Arg His Val Gly Pro
            1895                1900                1905
Gly Glu Gly Ala Val Gln Trp Met Asn Arg Leu Ile Ala Phe Ala
            1910                1915                1920
Ser Arg Gly Asn His Val Ser Pro Thr His Tyr Val Pro Glu Ser
            1925                1930                1935
Asp Ala Ala Ala Arg Val Thr Thr Ile Leu Ser Ser Leu Thr Val
            1940                1945                1950
Thr Gln Leu Leu Arg Arg Leu His Gln Trp Ile Ser Ser Glu Cys
            1955                1960                1965
Thr Thr Pro Cys Ser Gly Ser Trp Leu Arg Asp Ile Trp Asp Trp
            1970                1975                1980
Ile Cys Glu Val Leu Ser Asp Phe Lys Thr Trp Leu Lys Ala Lys
            1985                1990                1995
Leu Met Pro Gln Leu Pro Gly Ile Pro Phe Val Ser Cys Gln Arg
            2000                2005                2010
Gly Tyr Lys Gly Val Trp Arg Gly Asp Gly Ile Met His Thr Arg
            2015                2020                2025
Cys His Cys Gly Ala Glu Ile Thr Gly His Val Lys Asn Gly Thr
            2030                2035                2040
Met Arg Ile Val Gly Pro Lys Thr Cys Arg Asn Met Trp Ser Gly
            2045                2050                2055
Thr Phe Pro Ile Asn Ala Tyr Thr Thr Gly Pro Cys Thr Pro Leu
            2060                2065                2070
Pro Ala Pro Asn Tyr Thr Phe Ala Leu Trp Arg Val Ser Ala Glu
            2075                2080                2085
Glu Tyr Val Glu Ile Arg Gln Val Gly Asp Phe His Tyr Val Thr
            2090                2095                2100
Gly Met Thr Thr Asp Asn Leu Lys Cys Pro Cys Gln Val Pro Ser
            2105                2110                2115
Pro Glu Phe Phe Thr Glu Leu Asp Gly Val Arg Leu His Arg Phe
            2120                2125                2130
Ala Pro Pro Cys Lys Pro Leu Leu Arg Glu Glu Val Ser Phe Arg
            2135                2140                2145
Val Gly Leu His Glu Tyr Pro Val Gly Ser Gln Leu Pro Cys Glu
            2150                2155                2160
Pro Glu Pro Asp Val Ala Val Leu Thr Ser Met Leu Thr Asp Pro
            2165                2170                2175
Ser His Ile Thr Ala Glu Ala Ala Gly Arg Arg Leu Ala Arg Gly
            2180                2185                2190
Ser Pro Pro Ser Met Ala Ser Ser Ser Ala Ser Gln Leu Ser Ala
            2195                2200                2205
Pro Ser Leu Arg Ala Thr Cys Thr Thr Asn His Asp Ser Pro Asp
            2210                2215                2220
Ala Glu Leu Ile Glu Ala Asn Leu Leu Trp Arg Gln Glu Met Gly
            2225                2230                2235
Gly Asn Ile Thr Arg Val Glu Ser Glu Asn Lys Val Val Ile Leu
            2240                2245                2250
Asp Ser Phe Asp Pro Leu Val Ala Glu Glu Asp Glu Arg Glu Val
            2255                2260                2265
```

-continued

```
Ser Val Pro Ala Glu Ile Leu Arg Lys Ser Arg Lys Phe Thr Pro
    2270                2275                2280

Ala Leu Pro Ile Trp Ala Arg Pro Asp Tyr Asn Pro Pro Leu Val
    2285                2290                2295

Glu Pro Trp Lys Lys Pro Asp Tyr Glu Pro Pro Val Val His Gly
    2300                2305                2310

Cys Pro Leu Pro Pro Pro Gln Ser Pro Pro Val Pro Pro Pro Arg
    2315                2320                2325

Lys Lys Arg Thr Val Ile Leu Thr Glu Ser Thr Leu Pro Thr Ala
    2330                2335                2340

Leu Ala Glu Leu Ala Thr Lys Ser Phe Gly Ser Ser Ser Thr Ser
    2345                2350                2355

Gly Ile Thr Gly Asp Asp Thr Thr Thr Ser Pro Glu Pro Ala Ser
    2360                2365                2370

Ser Ser Cys Pro Pro Asp Ser Asp Ala Glu Ser Tyr Ser Ser Met
    2375                2380                2385

Pro Pro Leu Glu Gly Glu Pro Gly Asp Pro Asp Leu Ser Asp Gly
    2390                2395                2400

Ser Trp Ser Thr Val Ser Ser Glu Ala Asp Lys Glu Asp Val Val
    2405                2410                2415

Cys Cys Ser Met Ser Tyr Ser Trp Thr Gly Ala Leu Ile Thr Pro
    2420                2425                2430

Cys Ser Pro Glu Glu Glu Lys Leu Pro Ile Asn Pro Leu Ser Asn
    2435                2440                2445

Ser Leu Leu Arg Tyr His Asn Lys Val Tyr Cys Thr Thr Ser Lys
    2450                2455                2460

Ser Ala Ser Gln Arg Ala Lys Lys Val Thr Phe Asp Arg Thr Gln
    2465                2470                2475

Val Leu Asp Ala His Tyr Asp Ser Val Leu Lys Asp Ile Lys Leu
    2480                2485                2490

Ala Ala Ser Lys Val Ser Ala Arg Leu Leu Thr Leu Glu Glu Ala
    2495                2500                2505

Cys Gln Leu Thr Pro Pro His Ser Ala Arg Ser Lys Tyr Gly Phe
    2510                2515                2520

Gly Ala Lys Glu Val Arg Ser Leu Ser Gly Arg Ala Val Asn His
    2525                2530                2535

Ile Lys Ser Val Trp Lys Asp Leu Leu Glu Asp Pro Gln Thr Pro
    2540                2545                2550

Ile Pro Thr Thr Ile Met Ala Lys Asn Glu Val Phe Cys Val Asp
    2555                2560                2565

Pro Ala Lys Gly Gly Lys Lys Pro Ala Arg Leu Ile Val Tyr Pro
    2570                2575                2580

Asp Leu Gly Val Arg Val Cys Glu Lys Met Ala Leu Tyr Asp Ile
    2585                2590                2595

Thr Gln Lys Leu Pro Gln Ala Val Met Gly Ala Ser Tyr Gly Phe
    2600                2605                2610

Gln Tyr Ser Pro Ala Gln Arg Val Glu Tyr Leu Leu Lys Ala Trp
    2615                2620                2625

Ala Glu Lys Lys Asp Pro Met Gly Phe Ser Tyr Asp Thr Arg Cys
    2630                2635                2640

Phe Asp Ser Thr Val Thr Glu Arg Asp Ile Arg Thr Glu Glu Ser
    2645                2650                2655
```

Ile Tyr Gln Ala Cys Ser Leu Pro Glu Glu Ala Arg Thr Ala Ile
2660            2665                2670

His Ser Leu Thr Glu Arg Leu Tyr Val Gly Gly Pro Met Phe Asn
2675            2680                2685

Ser Lys Gly Gln Thr Cys Gly Tyr Arg Arg Cys Arg Ala Ser Gly
2690            2695                2700

Val Leu Thr Thr Ser Met Gly Asn Thr Ile Thr Cys Tyr Val Lys
2705            2710                2715

Ala Leu Ala Ala Cys Lys Ala Ala Gly Ile Val Ala Pro Thr Met
2720            2725                2730

Leu Val Cys Gly Asp Asp Leu Val Val Ile Ser Glu Ser Gln Gly
2735            2740                2745

Thr Glu Glu Asp Glu Arg Asn Leu Arg Ala Phe Thr Glu Ala Met
2750            2755                2760

Thr Arg Tyr Ser Ala Pro Pro Gly Asp Pro Pro Arg Pro Glu Tyr
2765            2770                2775

Asp Leu Glu Leu Ile Thr Ser Cys Ser Ser Asn Val Ser Val Ala
2780            2785                2790

Leu Gly Pro Arg Gly Arg Arg Tyr Tyr Leu Thr Arg Asp Pro
2795            2800                2805

Thr Thr Pro Leu Ala Arg Ala Ala Trp Glu Thr Val Arg His Ser
2810            2815                2820

Pro Ile Asn Ser Trp Leu Gly Asn Ile Ile Gln Tyr Ala Pro Thr
2825            2830                2835

Ile Trp Val Arg Met Val Leu Met Thr His Phe Phe Ser Ile Leu
2840            2845                2850

Met Val Gln Asp Thr Leu Asp Gln Asn Leu Asn Phe Glu Met Tyr
2855            2860                2865

Gly Ser Val Tyr Ser Val Asn Pro Leu Asp Leu Pro Ala Ile Ile
2870            2875                2880

Glu Arg Leu His Gly Leu Asp Ala Phe Ser Met His Thr Tyr Ser
2885            2890                2895

His His Glu Leu Thr Arg Val Ala Ser Ala Leu Arg Lys Leu Gly
2900            2905                2910

Ala Pro Pro Leu Arg Val Trp Lys Ser Arg Ala Arg Ala Val Arg
2915            2920                2925

Ala Ser Leu Ile Ser Arg Gly Gly Lys Ala Ala Val Cys Gly Arg
2930            2935                2940

Tyr Leu Phe Asn Trp Ala Val Lys Thr Lys Leu Lys Leu Thr Pro
2945            2950                2955

Leu Pro Glu Ala Arg Leu Leu Asp Leu Ser Ser Trp Phe Thr Val
2960            2965                2970

Gly Ala Gly Gly Gly Gly Ile Phe His Ser Val Ser Arg Ala Arg
2975            2980                2985

Pro Arg Ser Leu Leu Phe Gly Leu Leu Leu Leu Phe Val Gly Val
2990            2995                3000

Gly Leu Phe Leu Leu Pro Ala Arg
3005            3010

<210> SEQ ID NO 9
<211> LENGTH: 3021
<212> TYPE: PRT
<213> ORGANISM: Hepatitis C virus

<400> SEQUENCE: 9

-continued

```
Met Ser Thr Leu Pro Lys Pro Gln Arg Lys Thr Lys Arg Asn Thr Ile
1               5                   10                  15
Arg Arg Pro Gln Asp Val Lys Phe Pro Gly Gly Gln Ile Val Gly
            20                  25                  30
Gly Val Tyr Val Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
50                  55                  60
Ile Pro Lys Ala Arg Arg Ser Glu Gly Arg Ser Trp Ala Gln Pro Gly
65                  70                  75                  80
Tyr Pro Trp Pro Leu Tyr Gly Asn Glu Gly Cys Gly Trp Ala Gly Trp
                85                  90                  95
Leu Leu Ser Pro Arg Gly Ser Arg Pro Ser Trp Gly Pro Asn Asp Pro
                100                 105                 110
Arg Arg Arg Ser Arg Asn Leu Gly Lys Val Ile Asp Thr Leu Thr Cys
            115                 120                 125
Gly Phe Ala Asp Leu Met Gly Tyr Ile Pro Leu Val Gly Ala Pro Val
    130                 135                 140
Gly Gly Val Ala Arg Ala Leu Ala His Gly Val Arg Ala Leu Glu Asp
145                 150                 155                 160
Gly Ile Asn Phe Ala Thr Gly Asn Leu Pro Gly Cys Ser Phe Ser Ile
                165                 170                 175
Phe Leu Leu Ala Leu Phe Ser Cys Leu Val His Pro Ala Ala Ser Leu
                180                 185                 190
Glu Trp Arg Asn Thr Ser Gly Leu Tyr Val Leu Thr Asn Asp Cys Ser
            195                 200                 205
Asn Ser Ser Ile Val Tyr Glu Ala Asp Asp Val Ile Leu His Thr Pro
210                 215                 220
Gly Cys Val Pro Cys Val Gln Asp Asp Asn Thr Ser Thr Cys Trp Thr
225                 230                 235                 240
Pro Val Thr Pro Thr Val Ala Val Arg Tyr Val Gly Ala Thr Thr Ala
                245                 250                 255
Ser Ile Arg Ser His Val Asp Leu Leu Val Gly Ala Ala Thr Leu Cys
            260                 265                 270
Ser Ala Leu Tyr Val Gly Asp Met Cys Gly Ala Val Phe Leu Val Gly
    275                 280                 285
Gln Ala Phe Thr Phe Arg Pro Arg Arg His Gln Thr Val Gln Thr Cys
290                 295                 300
Asn Cys Ser Leu Tyr Pro Gly His Val Ser Gly His Arg Met Ala Trp
305                 310                 315                 320
Asp Met Met Met Asn Trp Ser Pro Ala Val Gly Met Val Val Ala His
                325                 330                 335
Ile Leu Arg Leu Pro Gln Thr Leu Phe Asp Ile Leu Ala Gly Ala His
            340                 345                 350
Trp Gly Ile Leu Ala Gly Leu Ala Tyr Tyr Ser Met Gln Gly Asn Trp
    355                 360                 365
Ala Lys Val Ala Ile Val Met Ile Met Phe Ser Gly Val Asp Ala Glu
370                 375                 380
Thr Tyr Val Thr Gly Gly Ser Val Ala His Ser Ala Arg Gly Leu Thr
385                 390                 395                 400
Ser Leu Phe Ser Met Gly Ala Lys Gln Lys Leu Gln Leu Val Asn Thr
                405                 410                 415
```

-continued

```
Asn Gly Ser Trp His Ile Asn Ser Thr Ala Leu Asn Cys Asn Glu Ser
                420                 425                 430

Ile Asn Thr Gly Phe Ile Ala Gly Leu Phe Tyr Tyr His Lys Phe Asn
            435                 440                 445

Ser Thr Gly Cys Pro Gln Arg Leu Ser Ser Cys Lys Pro Ile Ile Ser
        450                 455                 460

Phe Arg Gln Gly Trp Gly Pro Leu Thr Asp Ala Asn Ile Thr Gly Pro
465                 470                 475                 480

Ser Asp Asp Arg Pro Tyr Cys Trp His Tyr Ala Pro Arg Pro Cys Ser
                485                 490                 495

Val Val Pro Ala Ser Ser Val Cys Gly Pro Val Tyr Cys Phe Thr Pro
            500                 505                 510

Ser Pro Val Val Val Gly Thr Thr Asp Ile Lys Gly Lys Pro Thr Tyr
        515                 520                 525

Asn Trp Gly Glu Asn Glu Thr Asp Val Phe Leu Leu Glu Ser Leu Arg
            530                 535                 540

Pro Pro Ser Gly Arg Trp Phe Gly Cys Ala Trp Met Asn Ser Thr Gly
545                 550                 555                 560

Phe Leu Lys Thr Cys Gly Ala Pro Pro Cys Asn Ile Tyr Gly Gly Glu
                565                 570                 575

Gly Asp Pro Glu Asn Glu Thr Asp Leu Phe Cys Pro Thr Asp Cys Phe
            580                 585                 590

Arg Lys His Pro Glu Ala Thr Tyr Ser Arg Cys Gly Ala Gly Pro Trp
        595                 600                 605

Leu Thr Pro Arg Cys Met Val Asp Tyr Pro Tyr Arg Leu Trp His Tyr
610                 615                 620

Pro Cys Thr Val Asn Phe Thr Leu Phe Lys Val Arg Met Phe Val Gly
625                 630                 635                 640

Gly Phe Glu His Arg Phe Thr Ala Ala Cys Asn Trp Thr Arg Gly Glu
                645                 650                 655

Arg Cys Asn Ile Glu Asp Arg Asp Arg Ser Glu Gln His Pro Leu Leu
            660                 665                 670

His Ser Thr Thr Glu Leu Ala Ile Leu Pro Cys Ser Phe Thr Pro Met
        675                 680                 685

Pro Ala Leu Ser Thr Gly Leu Ile His Leu His Gln Asn Ile Val Asp
690                 695                 700

Val Gln Tyr Leu Tyr Gly Val Gly Ser Asp Met Val Gly Trp Ala Leu
705                 710                 715                 720

Lys Trp Glu Phe Val Ile Leu Val Phe Leu Leu Leu Ala Asp Ala Arg
                725                 730                 735

Val Cys Val Ala Leu Trp Leu Met Leu Met Val Ser Gln Ala Glu Ala
            740                 745                 750

Ala Leu Glu Asn Leu Val Thr Leu Asn Ala Val Ala Ala Gly Thr
        755                 760                 765

His Gly Ile Gly Trp Tyr Leu Val Ala Phe Cys Ala Ala Trp Tyr Val
        770                 775                 780

Arg Gly Lys Leu Val Pro Leu Thr Ile Tyr Gly Leu Thr Gly Leu Trp
785                 790                 795                 800

Ser Leu Ala Leu Leu Val Leu Leu Leu Pro Gln Arg Ala Tyr Ala Trp
                805                 810                 815

Ser Gly Glu Asp Ser Ala Thr Leu Gly Ala Gly Val Leu Ala Leu Phe
            820                 825                 830

Gly Phe Phe Thr Leu Ser Pro Trp Tyr Lys His Trp Ile Gly Arg Leu
```

-continued

```
                835                 840                 845
Met Trp Trp Asn Gln Tyr Thr Ile Cys Arg Cys Glu Ala Ala Leu Gln
850                 855                 860

Val Trp Val Pro Pro Leu Leu Ala Arg Gly Ser Arg Gly Gly Val Ile
865                 870                 875                 880

Leu Leu Thr Ser Leu Leu Tyr Pro Ser Leu Ile Phe Asp Ile Thr Lys
                885                 890                 895

Leu Leu Ile Ala Val Ile Gly Pro Leu Tyr Leu Ile Gln Ala Ala Ile
                900                 905                 910

Thr Thr Thr Pro Tyr Phe Val Arg Ala His Val Leu Val Arg Leu Cys
                915                 920                 925

Met Leu Val Arg Ser Val Met Gly Gly Lys Tyr Phe Gln Met Ala Ile
930                 935                 940

Leu Ser Ile Gly Arg Trp Phe Asn Thr Tyr Leu Tyr Asp His Leu Ala
945                 950                 955                 960

Pro Met Gln His Trp Ala Ala Ala Gly Leu Lys Asp Leu Ala Val Ala
                965                 970                 975

Thr Glu Pro Val Ile Phe Ser Pro Met Glu Ile Lys Val Ile Thr Trp
                980                 985                 990

Gly Ala Asp Thr Ala Ala Cys Gly Asp Ile Leu Cys Gly Leu Pro Val
                995                 1000                1005

Ser Ala Arg Leu Gly Arg Glu Val Leu Leu Gly Pro Ala Asp Asp
        1010                1015                1020

Tyr Arg Glu Met Gly Trp Arg Leu Leu Ala Pro Ile Thr Ala Tyr
        1025                1030                1035

Ala Gln Gln Thr Arg Gly Leu Leu Gly Thr Ile Val Thr Ser Leu
        1040                1045                1050

Thr Gly Arg Asp Lys Asn Ile Val Thr Gly Glu Val Gln Val Leu
        1055                1060                1065

Ser Thr Ala Thr Gln Thr Phe Leu Gly Thr Thr Val Gly Gly Val
        1070                1075                1080

Met Trp Thr Val Tyr His Gly Ala Gly Ser Lys Thr Leu Ala Gly
        1085                1090                1095

Ala Lys His Pro Ala Leu Gln Met Tyr Thr Asn Val Asp Gln Asp
        1100                1105                1110

Leu Val Gly Trp Pro Ala Pro Pro Gly Ala Lys Ser Leu Glu Pro
        1115                1120                1125

Cys Ala Cys Gly Ser Ala Asp Leu Tyr Leu Val Thr Arg Asp Ala
        1130                1135                1140

Asp Val Ile Pro Ala Arg Arg Arg Gly Asp Ser Thr Ala Ser Leu
        1145                1150                1155

Leu Ser Pro Arg Pro Leu Ala Cys Leu Lys Gly Ser Ser Gly Gly
        1160                1165                1170

Pro Val Met Cys Pro Ser Gly His Val Ala Gly Ile Phe Arg Ala
        1175                1180                1185

Ala Val Cys Thr Arg Gly Val Ala Lys Ala Leu Gln Phe Val Pro
        1190                1195                1200

Val Glu Thr Leu Ser Thr Gln Ala Arg Ser Pro Ser Phe Ser Asp
        1205                1210                1215

Asn Ser Thr Pro Pro Ala Val Pro Gln Ser Tyr Gln Val Gly Tyr
        1220                1225                1230

Leu His Ala Pro Thr Gly Ser Gly Lys Ser Thr Lys Val Pro Ala
        1235                1240                1245
```

```
Ala Tyr Val Ala Gln Gly Tyr Asn Val Leu Val Leu Asn Pro Ser
    1250                1255                1260
Val Ala Ala Thr Leu Gly Phe Gly Ser Phe Met Ser Arg Ala Tyr
    1265                1270                1275
Gly Ile Asp Pro Asn Ile Arg Thr Gly Asn Arg Thr Val Thr Thr
    1280                1285                1290
Gly Ala Lys Leu Thr Tyr Ser Thr Tyr Gly Lys Phe Leu Ala Asp
    1295                1300                1305
Gly Gly Cys Ser Gly Gly Ala Tyr Asp Val Ile Ile Cys Asp Glu
    1310                1315                1320
Cys His Ala Gln Asp Ala Thr Ser Ile Leu Gly Ile Gly Thr Val
    1325                1330                1335
Leu Asp Gln Ala Glu Thr Ala Gly Val Arg Leu Thr Val Leu Ala
    1340                1345                1350
Thr Ala Thr Pro Pro Gly Ser Ile Thr Val Pro His Ser Asn Ile
    1355                1360                1365
Glu Glu Val Ala Leu Gly Ser Glu Gly Glu Ile Pro Phe Tyr Gly
    1370                1375                1380
Lys Ala Ile Pro Ile Ala Leu Leu Lys Gly Gly Arg His Leu Ile
    1385                1390                1395
Phe Cys His Ser Lys Lys Lys Cys Asp Glu Val Ala Ala Lys Leu
    1400                1405                1410
Arg Gly Met Gly Leu Asn Ala Val Ala Tyr Tyr Arg Gly Leu Asp
    1415                1420                1425
Val Ser Val Ile Pro Thr Thr Gly Asp Val Val Cys Ala Thr
    1430                1435                1440
Asp Ala Leu Met Thr Gly Phe Thr Gly Asp Phe Asp Ser Val Ile
    1445                1450                1455
Asp Cys Asn Val Ala Val Glu Gln Tyr Val Asp Leu Ser Leu Asp
    1460                1465                1470
Pro Thr Phe Ser Ile Glu Thr Arg Thr Ala Pro Gln Asp Ala Val
    1475                1480                1485
Ser Arg Ser Gln Arg Arg Gly Arg Thr Gly Arg Gly Arg Leu Gly
    1490                1495                1500
Thr Tyr Arg Tyr Val Ala Pro Gly Glu Arg Pro Ser Gly Met Phe
    1505                1510                1515
Asp Ser Val Val Leu Cys Glu Cys Tyr Asp Ala Gly Cys Ser Trp
    1520                1525                1530
Tyr Asp Leu Gln Pro Ala Glu Thr Thr Val Arg Leu Arg Ala Tyr
    1535                1540                1545
Leu Asn Thr Pro Gly Leu Pro Val Cys Gln Asp His Leu Asp Phe
    1550                1555                1560
Trp Glu Ser Val Phe Thr Gly Leu Thr His Ile Asp Ala His Phe
    1565                1570                1575
Leu Ser Gln Thr Lys Gln Gln Gly Leu Asn Phe Ser Phe Leu Thr
    1580                1585                1590
Ala Tyr Gln Ala Thr Val Cys Ala Arg Ala Gln Ala Ser Pro Pro
    1595                1600                1605
Ser Trp Asp Glu Thr Trp Lys Cys Leu Glu Arg Leu Lys Pro Thr
    1610                1615                1620
Leu His Gly Pro Thr Pro Leu Leu Tyr Arg Leu Gly Pro Val Gln
    1625                1630                1635
```

-continued

```
Asn Asp Ile Cys Leu Thr His Pro Val Thr Lys Tyr Ile Met Ala
1640                1645                1650
Cys Met Ser Ala Asp Leu Glu Val Thr Thr Ser Thr Trp Val Leu
1655                1660                1665
Leu Gly Gly Val Leu Ala Ala Leu Ala Ser Tyr Cys Leu Ser Val
1670                1675                1680
Gly Cys Val Val Ile Val Gly His Ile Glu Leu Arg Gly Lys Pro
1685                1690                1695
Ala Leu Val Pro Asp Arg Glu Val Leu Tyr Gln Gln Tyr Asp Glu
1700                1705                1710
Met Glu Glu Cys Ser Gln Ala Ala Pro Tyr Ile Glu Gln Ala Gln
1715                1720                1725
Ala Ile Ala His Gln Phe Lys Glu Lys Ile Leu Gly Leu Leu Gln
1730                1735                1740
Arg Ala Thr Gln Gln Ala Val Ile Glu Pro Ile Val Ala Thr
1745                1750                1755
Asn Trp Gln Lys Leu Glu Thr Phe Trp His Lys His Met Trp Asn
1760                1765                1770
Phe Val Ser Gly Ile Gln Tyr Leu Ala Gly Leu Ser Thr Leu Pro
1775                1780                1785
Gly Asn Pro Ala Val Ala Ser Leu Met Ala Phe Thr Ala Ser Val
1790                1795                1800
Thr Ser Pro Leu Thr Thr Asn Gln Thr Met Phe Phe Asn Ile Leu
1805                1810                1815
Gly Gly Trp Val Ala Thr Arg Leu Ala Gly Pro Gln Ser Ser Ser
1820                1825                1830
Ala Phe Val Val Ser Gly Leu Ala Gly Ala Ala Ile Gly Gly Ile
1835                1840                1845
Gly Leu Gly Arg Val Leu Leu Asp Ile Leu Ala Gly Tyr Gly Ala
1850                1855                1860
Gly Val Ser Gly Ala Leu Val Ala Phe Lys Ile Met Gly Gly Glu
1865                1870                1875
Leu Pro Thr Thr Glu Asp Met Val Asn Leu Leu Pro Ala Ile Leu
1880                1885                1890
Ser Pro Gly Ala Leu Val Val Gly Val Ile Cys Ala Ala Ile Leu
1895                1900                1905
Arg Arg His Val Gly Pro Gly Glu Gly Ala Val Gln Trp Met Asn
1910                1915                1920
Arg Leu Ile Ala Phe Ala Ser Arg Gly Asn His Val Ser Pro Thr
1925                1930                1935
His Tyr Val Pro Glu Ser Asp Ala Ala Ala Arg Val Thr Ala Leu
1940                1945                1950
Leu Ser Ser Leu Thr Val Thr Ser Leu Leu Arg Arg Leu His Lys
1955                1960                1965
Trp Ile Asn Glu Asp Tyr Pro Ser Pro Cys Ser Gly Asp Trp Leu
1970                1975                1980
Arg Asp Ile Trp Asp Trp Val Cys Ser Val Leu Ser Asp Phe Lys
1985                1990                1995
Thr Trp Leu Ser Ala Lys Ile Met Pro Ala Leu Pro Gly Leu Pro
2000                2005                2010
Phe Ile Ser Cys Gln Lys Gly Tyr Lys Gly Val Trp Arg Gly Asp
2015                2020                2025
Gly Val Met Ser Thr Arg Cys Pro Cys Gly Ala Ser Ile Thr Gly
```

-continued

```
            2030                2035                2040
His Val Lys Asn Gly Ser Met Arg Leu Ala Gly Pro Arg Met Cys
        2045                2050                2055
Ala Asn Met Trp His Gly Thr Phe Pro Ile Asn Glu Tyr Thr Thr
        2060                2065                2070
Gly Pro Ser Thr Pro Cys Pro Ser Pro Asn Tyr Thr Arg Ala Leu
        2075                2080                2085
Trp Arg Val Ala Ala Ser Ser Tyr Val Glu Val Arg Arg Val Gly
        2090                2095                2100
Asp Phe His Tyr Ile Thr Gly Ala Thr Glu Asp Glu Leu Lys Cys
        2105                2110                2115
Pro Cys Gln Val Pro Ala Ala Glu Phe Phe Thr Glu Val Asp Gly
        2120                2125                2130
Val Arg Leu His Arg Tyr Ala Pro Pro Cys Lys Pro Leu Leu Arg
        2135                2140                2145
Glu Glu Ile Thr Phe Ser Val Gly Leu His Ser Tyr Ala Ile Gly
        2150                2155                2160
Ser Gln Leu Pro Cys Glu Pro Glu Pro Asp Val Ser Val Leu Thr
        2165                2170                2175
Ser Met Leu Arg Asp Pro Ser His Ile Thr Ala Glu Thr Ala Ala
        2180                2185                2190
Arg Arg Leu Ala Arg Gly Ser Pro Pro Ser Glu Ala Ser Ser Ser
        2195                2200                2205
Ala Ser Gln Leu Ser Ala Pro Ser Leu Lys Ala Thr Cys Gln Thr
        2210                2215                2220
His Arg Pro His Pro Asp Ala Glu Leu Val Asp Ala Asn Leu Leu
        2225                2230                2235
Trp Arg Gln Glu Met Gly Ser Asn Ile Thr Arg Val Glu Ser Glu
        2240                2245                2250
Thr Lys Val Val Ile Leu Asp Ser Phe Glu Pro Leu Arg Ala Glu
        2255                2260                2265
Ala Asp Asp Ala Glu Leu Ser Val Ala Ala Glu Cys Phe Lys Lys
        2270                2275                2280
Pro Pro Lys Tyr Pro Pro Ala Leu Pro Ile Trp Ala Arg Pro Asp
        2285                2290                2295
Tyr Asn Pro Pro Leu Leu Asp Arg Trp Lys Ala Pro Asp Tyr Val
        2300                2305                2310
Pro Pro Thr Val His Gly Cys Ala Leu Pro Pro Arg Gly Ala Pro
        2315                2320                2325
Pro Val Pro Pro Pro Arg Arg Lys Arg Thr Ile Gln Leu Asp Gly
        2330                2335                2340
Ser Asn Val Ser Ala Ala Leu Ala Ala Leu Ala Glu Lys Ser Phe
        2345                2350                2355
Pro Thr Pro Lys Ser Gln Glu Glu Asn Ser Ser Ser Ser Gly Val
        2360                2365                2370
Asp Thr Gln Ser Ser Thr Thr Ser Arg Met Pro Pro Ser Pro Gly
        2375                2380                2385
Gly Glu Ser Asp Ser Glu Ser Cys Ser Ser Met Pro Pro Leu Glu
        2390                2395                2400
Gly Glu Pro Gly Asp Pro Asp Leu Ser Cys Asp Ser Trp Ser Thr
        2405                2410                2415
Val Ser Asp Asn Glu Glu Gln Ser Ala Val Cys Cys Ser Met Ser
        2420                2425                2430
```

```
Tyr Ser Trp Thr Gly Ala Leu Ile Thr Pro Cys Ser Pro Glu Glu
2435                2440                2445

Glu Lys Leu Pro Ile Asn Pro Leu Ser Asn Ser Leu Leu Arg Tyr
2450                2455                2460

His Asn Lys Val Tyr Cys Thr Thr Ser Lys Ser Ala Ser Gln Arg
2465                2470                2475

Ala Lys Lys Val Thr Phe Asp Arg Thr Gln Val Leu Asp Ala His
2480                2485                2490

Tyr Asp Ser Val Leu Lys Asp Ile Lys Leu Ala Ala Ser Lys Val
2495                2500                2505

Ser Ala Arg Leu Leu Thr Leu Glu Glu Ala Cys Gln Leu Thr Pro
2510                2515                2520

Pro His Ser Ala Arg Ser Lys Tyr Gly Phe Gly Ala Lys Glu Val
2525                2530                2535

Arg Ser Leu Ser Gly Arg Ala Val Asn His Ile Lys Ser Val Trp
2540                2545                2550

Lys Asp Leu Leu Glu Asp Pro Gln Thr Pro Ile Pro Thr Thr Ile
2555                2560                2565

Met Ala Lys Asn Glu Val Phe Cys Val Asp Pro Ala Lys Gly Gly
2570                2575                2580

Lys Lys Pro Ala Arg Leu Ile Val Tyr Pro Asp Leu Gly Val Arg
2585                2590                2595

Val Cys Glu Lys Met Ala Leu Tyr Asp Ile Thr Gln Lys Leu Pro
2600                2605                2610

Gln Ala Val Met Gly Ala Ser Tyr Gly Phe Gln Tyr Ser Pro Ala
2615                2620                2625

Gln Arg Val Glu Tyr Leu Leu Lys Ala Trp Ala Glu Lys Lys Asp
2630                2635                2640

Pro Met Gly Phe Ser Tyr Asp Thr Arg Cys Phe Asp Ser Thr Val
2645                2650                2655

Thr Glu Arg Asp Ile Arg Thr Glu Glu Ser Ile Tyr Gln Ala Cys
2660                2665                2670

Ser Leu Pro Glu Glu Ala Arg Thr Ala Ile His Ser Leu Thr Glu
2675                2680                2685

Arg Leu Tyr Val Gly Gly Pro Met Phe Asn Ser Lys Gly Gln Thr
2690                2695                2700

Cys Gly Tyr Arg Arg Cys Arg Ala Ser Gly Val Leu Thr Thr Ser
2705                2710                2715

Met Gly Asn Thr Ile Thr Cys Tyr Val Lys Ala Leu Ala Ala Cys
2720                2725                2730

Lys Ala Ala Gly Ile Val Ala Pro Thr Met Leu Val Cys Gly Asp
2735                2740                2745

Asp Leu Val Val Ile Ser Glu Ser Gln Gly Thr Glu Glu Asp Glu
2750                2755                2760

Arg Asn Leu Arg Ala Phe Thr Glu Ala Met Thr Arg Tyr Ser Ala
2765                2770                2775

Pro Pro Gly Asp Pro Pro Arg Pro Glu Tyr Asp Leu Glu Leu Ile
2780                2785                2790

Thr Ser Cys Ser Ser Asn Val Ser Val Ala Leu Gly Pro Arg Gly
2795                2800                2805

Arg Arg Arg Tyr Tyr Leu Thr Arg Asp Pro Thr Thr Pro Leu Ala
2810                2815                2820
```

```
Arg Ala Ala Trp Glu Thr Val Arg His Ser Pro Ile Asn Ser Trp
2825                2830                2835

Leu Gly Asn Ile Ile Gln Tyr Ala Pro Thr Ile Trp Val Arg Met
2840                2845                2850

Val Leu Met Thr His Phe Phe Ser Ile Leu Met Val Gln Asp Thr
2855                2860                2865

Leu Asp Gln Asn Leu Asn Phe Glu Met Tyr Gly Ser Val Tyr Ser
2870                2875                2880

Val Asn Pro Leu Asp Leu Pro Ala Ile Ile Glu Arg Leu His Gly
2885                2890                2895

Leu Asp Ala Phe Ser Met His Thr Tyr Ser His His Glu Leu Thr
2900                2905                2910

Arg Val Ala Ser Ala Leu Arg Lys Leu Gly Ala Pro Pro Leu Arg
2915                2920                2925

Val Trp Lys Ser Arg Ala Arg Ala Val Arg Ala Ser Leu Ile Ser
2930                2935                2940

Arg Gly Gly Lys Ala Ala Val Cys Gly Arg Tyr Leu Phe Asn Trp
2945                2950                2955

Ala Val Lys Thr Lys Leu Lys Leu Thr Pro Leu Pro Glu Ala Arg
2960                2965                2970

Leu Leu Asp Leu Ser Ser Trp Phe Thr Val Gly Ala Gly Gly Gly
2975                2980                2985

Gly Ile Phe His Ser Val Ser Arg Ala Arg Pro Arg Ser Leu Leu
2990                2995                3000

Phe Gly Leu Leu Leu Leu Phe Val Gly Val Gly Leu Phe Leu Leu
3005                3010                3015

Pro Ala Arg
3020

<210> SEQ ID NO 10
<211> LENGTH: 3008
<212> TYPE: PRT
<213> ORGANISM: Hepatitis C virus

<400> SEQUENCE: 10

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160
```

-continued

```
Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Val Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Gly Thr Thr Asp His Val Gly Val Pro Thr Tyr
        515                 520                 525

Thr Trp Gly Glu Asn Glu Thr Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575
```

```
Gly Thr Trp His Cys Pro Thr Asp Cys Phe Arg Lys His Pro Glu Thr
            580                 585                 590

Thr Tyr Ala Lys Cys Gly Ser Gly Pro Trp Ile Thr Pro Arg Cys Leu
        595                 600                 605

Ile Asp Tyr Pro Tyr Arg Leu Trp His Phe Pro Cys Thr Ala Asn Phe
    610                 615                 620

Ser Val Phe Asn Ile Arg Thr Phe Val Gly Ile Glu His Arg Met
625                 630                 635                 640

Gln Ala Ala Cys Asn Trp Thr Arg Gly Glu Val Cys Gly Leu Glu His
                645                 650                 655

Arg Asp Arg Val Glu Leu Ser Pro Leu Leu Thr Thr Ala Trp
            660                 665                 670

Gln Ile Leu Pro Cys Ser Phe Thr Thr Leu Pro Ala Leu Ser Thr Gly
            675                 680                 685

Leu Ile His Leu His Gln Asn Ile Val Asp Val Gln Tyr Leu Tyr Gly
        690                 695                 700

Val Gly Ser Ala Val Val Ser Trp Ala Leu Lys Trp Glu Tyr Val Val
705                 710                 715                 720

Leu Ala Phe Leu Leu Leu Ala Asp Ala Arg Val Ser Ala Cys Leu Trp
                725                 730                 735

Met Met Phe Met Val Ser Gln Val Glu Ala Ala Leu Ser Asn Leu Ile
            740                 745                 750

Asn Ile Asn Ala Ala Ser Ala Ala Gly Ala Gln Gly Phe Trp Tyr Ala
                755                 760                 765

Ile Leu Phe Ile Cys Ile Val Trp His Val Lys Gly Trp Phe Pro Ala
    770                 775                 780

Ala Ala Ala Tyr Ala Ala Cys Gly Leu Trp Pro Leu Phe Leu Leu Leu
785                 790                 795                 800

Leu Met Leu Pro Glu Arg Ala Tyr Ala Tyr Asp Gln Glu Val Ala Gly
                805                 810                 815

Ser Leu Gly Gly Ala Ile Val Val Met Leu Thr Ile Leu Thr Leu Ser
            820                 825                 830

Pro His Tyr Lys Leu Trp Leu Ala Arg Gly Leu Trp Trp Ile Gln Tyr
            835                 840                 845

Phe Ile Ala Arg Thr Glu Ala Val Leu His Val Tyr Ile Pro Ser Phe
850                 855                 860

Asn Val Arg Gly Pro Arg Asp Ser Val Ile Val Leu Ala Val Leu Val
865                 870                 875                 880

Cys Pro His Leu Val Phe Asp Ile Thr Lys Tyr Leu Leu Ala Ile Leu
                885                 890                 895

Gly Pro Leu His Ile Leu Gln Ala Ser Leu Leu Arg Ile Pro Tyr Phe
            900                 905                 910

Val Arg Ala Gln Ala Leu Val Lys Ile Cys Ser Leu Leu Arg Gly Val
        915                 920                 925

Val Tyr Gly Lys Tyr Phe Gln Met Val Val Leu Lys Ala Gly Ala Leu
930                 935                 940

Thr Gly Thr Tyr Ile Tyr Asp His Leu Thr Pro Met Ser Asp Trp Ala
945                 950                 955                 960

Ala Thr Gly Leu Arg Asp Leu Ala Val Ala Leu Glu Pro Val Val Phe
                965                 970                 975

Thr Pro Met Glu Lys Lys Val Ile Val Trp Gly Ala Asp Thr Ala Ala
            980                 985                 990

Cys Gly Asp Ile Ile Arg Gly Leu  Pro Val Ser Ala Arg  Leu Gly Asn
```

-continued

```
         995                1000               1005
Glu Ile Leu Leu Gly Pro Ala Asp Thr Glu Thr Ser Lys Gly Trp
    1010            1015                1020

Arg Leu Leu Ala Pro Ile Thr Ala Tyr Ala Gln Gln Thr Arg Gly
    1025            1030                1035

Leu Phe Ser Thr Ile Val Thr Ser Leu Thr Gly Arg Asp Thr Asn
    1040            1045                1050

Glu Asn Cys Gly Glu Val Gln Val Leu Ser Thr Ala Thr Gln Ser
    1055            1060                1065

Phe Leu Gly Thr Ala Val Asn Gly Val Met Trp Thr Val Tyr His
    1070            1075                1080

Gly Ala Gly Ala Lys Thr Ile Ser Gly Pro Lys Gly Pro Val Asn
    1085            1090                1095

Gln Met Tyr Thr Asn Val Asp Gln Asp Leu Val Gly Trp Pro Ala
    1100            1105                1110

Pro Pro Gly Val Arg Ser Leu Ala Pro Cys Thr Cys Gly Ser Ala
    1115            1120                1125

Asp Leu Tyr Leu Val Thr Arg His Ala Asp Val Ile Pro Val Arg
    1130            1135                1140

Arg Arg Gly Asp Thr Arg Gly Ala Leu Leu Ser Pro Arg Pro Ile
    1145            1150                1155

Ser Thr Leu Lys Gly Ser Ser Gly Gly Pro Leu Leu Cys Pro Met
    1160            1165                1170

Gly His Ala Ala Gly Ile Phe Arg Ala Ala Val Cys Thr Arg Gly
    1175            1180                1185

Val Ala Lys Ala Val Asp Phe Val Pro Val Glu Ser Leu Glu Thr
    1190            1195                1200

Thr Met Arg Ser Pro Val Phe Thr Asp Asn Ser Thr Pro Pro Ala
    1205            1210                1215

Val Pro Gln Thr Tyr Gln Val Ala His Leu His Ala Pro Thr Gly
    1220            1225                1230

Ser Gly Lys Ser Thr Lys Val Pro Ala Ala Tyr Ala Ala Gln Gly
    1235            1240                1245

Tyr Lys Val Leu Val Leu Asn Pro Ser Val Ala Ala Thr Leu Gly
    1250            1255                1260

Phe Gly Val Tyr Met Ser Lys Ala Tyr Gly Ile Asp Pro Asn Ile
    1265            1270                1275

Arg Ser Gly Val Arg Thr Ile Thr Thr Gly Ala Pro Ile Thr Tyr
    1280            1285                1290

Ser Thr Tyr Gly Lys Phe Leu Ala Asp Gly Gly Cys Ser Gly Gly
    1295            1300                1305

Pro Tyr Asp Ile Ile Ile Cys Asp Glu Cys His Ser Thr Asp Ser
    1310            1315                1320

Thr Thr Ile Leu Gly Ile Gly Thr Val Leu Asp Gln Ala Glu Thr
    1325            1330                1335

Ala Gly Val Arg Leu Thr Val Leu Ala Thr Ala Thr Pro Pro Gly
    1340            1345                1350

Ser Val Thr Thr Pro His Ser Asn Ile Glu Glu Val Ala Leu Pro
    1355            1360                1365

Thr Thr Gly Glu Ile Pro Phe Tyr Gly Lys Ala Ile Pro Leu Glu
    1370            1375                1380

Leu Ile Lys Gly Gly Arg His Leu Ile Phe Cys His Ser Lys Lys
    1385            1390                1395
```

-continued

Lys Cys Asp Glu Leu Ala Arg Gln Leu Thr Ser Leu Gly Leu Asn
1400                1405                1410

Ala Val Ala Tyr Tyr Arg Gly Leu Asp Val Ser Val Ile Pro Thr
1415                1420                1425

Ser Gly Asp Val Val Cys Ala Thr Asp Ala Leu Met Thr Gly
1430                1435                1440

Phe Thr Gly Asp Phe Asp Ser Val Ile Asp Cys Asn Thr Ser Val
1445                1450                1455

Ile Gln Thr Val Asp Leu Ser Leu Asp Pro Thr Phe Ser Ile Glu
1460                1465                1470

Thr Thr Thr Val Pro Gln Asp Ala Val Ser Arg Ser Gln Arg Arg
1475                1480                1485

Gly Arg Thr Gly Arg Gly Arg Leu Gly Thr Tyr Arg Tyr Val Thr
1490                1495                1500

Pro Gly Glu Arg Pro Ser Gly Met Phe Asp Thr Ala Val Leu Cys
1505                1510                1515

Glu Cys Tyr Asp Ala Gly Cys Ala Trp Tyr Glu Leu Thr Pro Ala
1520                1525                1530

Glu Thr Thr Thr Arg Leu Lys Ala Tyr Phe Asp Thr Pro Gly Leu
1535                1540                1545

Pro Val Cys Gln Asp His Leu Glu Phe Trp Glu Ser Val Phe Thr
1550                1555                1560

Gly Leu Thr His Ile Asp Gly His Phe Leu Ser Gln Thr Lys Gln
1565                1570                1575

Ser Gly Glu Asn Phe Pro Tyr Leu Val Ala Tyr Gln Ala Thr Val
1580                1585                1590

Cys Ala Lys Ala Leu Ala Pro Pro Pro Ser Trp Asp Thr Met Trp
1595                1600                1605

Lys Cys Leu Ile Arg Leu Lys Pro Thr Leu His Gly Pro Thr Pro
1610                1615                1620

Leu Leu Tyr Arg Leu Gly Ser Val Gln Asn Glu Val Val Leu Thr
1625                1630                1635

His Pro Ile Thr Lys Tyr Ile Met Ala Cys Met Ser Ala Asp Leu
1640                1645                1650

Glu Val Val Thr Ser Thr Trp Val Leu Val Gly Gly Val Leu Ala
1655                1660                1665

Ala Leu Ala Ser Tyr Cys Leu Ser Val Gly Ser Val Val Ile Val
1670                1675                1680

Gly Arg Val Val Leu Ser Gly Gln Pro Ala Val Ile Pro Asp Arg
1685                1690                1695

Glu Val Leu Tyr Gln Gln Phe Asp Glu Met Glu Glu Cys Ser Lys
1700                1705                1710

His Leu Pro Leu Val Glu His Gly Leu Gln Leu Ala Glu Gln Phe
1715                1720                1725

Lys Gln Lys Ala Leu Gly Leu Leu Asn Phe Ala Gly Lys Gln Ala
1730                1735                1740

Gln Glu Ala Thr Pro Val Ile Gln Ser Asn Phe Ala Lys Leu Glu
1745                1750                1755

Gln Phe Trp Ala Lys His Met Trp Asn Phe Ile Ser Gly Ile Gln
1760                1765                1770

Tyr Leu Ala Gly Leu Ser Thr Leu Pro Gly Asn Pro Val Ile Ala
1775                1780                1785

-continued

```
Ser Leu Met Ser Phe Thr Ala Ala Val Thr Ser Pro Leu Thr Thr
    1790                1795                1800

Gln Gln Thr Leu Leu Phe Asn Ile Leu Gly Gly Trp Val Ala Ser
    1805                1810                1815

Gln Ile Ala Thr Pro Thr Ala Ser Thr Ala Phe Val Val Ser Gly
    1820                1825                1830

Leu Ala Gly Ala Ala Val Gly Ser Val Gly Leu Gly Lys Ile Leu
    1835                1840                1845

Val Asp Ile Leu Ala Gly Tyr Gly Ala Gly Val Ala Gly Ala Val
    1850                1855                1860

Val Thr Phe Lys Ile Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Thr Ile Leu Ser Ser Leu Thr Val
    1940                1945                1950

Thr Ser Leu Leu Arg Arg Leu His Lys Trp Ile Asn Glu Asp Cys
    1955                1960                1965

Ser Thr Pro Cys Ala Glu Ser Trp Leu Trp Glu Val Trp Asp Trp
    1970                1975                1980

Val Cys Thr Val Leu Ser Asp Phe Lys Thr Trp Leu Lys Ala Lys
    1985                1990                1995

Leu Leu Pro Leu Met Pro Gly Ile Pro Phe Leu Ser Cys Gln Arg
    2000                2005                2010

Gly Tyr Lys Gly Glu Trp Arg Gly Asp Gly Val Met His Thr Thr
    2015                2020                2025

Cys Pro Cys Gly Ala Asp Leu Ala Gly His Ile Lys Asn Gly Ser
    2030                2035                2040

Met Arg Ile Thr Gly Pro Lys Thr Cys Ser Asn Thr Trp His Gly
    2045                2050                2055

Thr Phe Pro Ile Asn Ala Tyr Thr Thr Gly Pro Gly Val Pro Ile
    2060                2065                2070

Pro Ala Pro Asn Tyr Lys Phe Ala Leu Trp Arg Val Ser Ala Glu
    2075                2080                2085

Asp Tyr Val Glu Val Arg Arg Val Gly Asp Phe His Tyr Val Thr
    2090                2095                2100

Gly Val Thr Gln Asp Asn Ile Lys Cys Pro Cys Gln Val Pro Ala
    2105                2110                2115

Pro Glu Phe Phe Thr Glu Val Asp Gly Ile Arg Leu His Arg His
    2120                2125                2130

Ala Pro Lys Cys Lys Pro Leu Leu Arg Asp Glu Val Ser Phe Ser
    2135                2140                2145

Val Gly Leu Asn Ser Phe Val Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Ser Ala Arg Arg Arg Leu Ala Arg Gly
```

```
              2180            2185            2190
Ser Arg Pro Ser Leu Ala Ser Ser Ser Ala Ser Gln Leu Ser Ala
    2195            2200            2205
Pro Ser Leu Lys Ala Thr Cys Thr Ala Pro His Asp Ser Pro Gly
    2210            2215            2220
Thr Asp Leu Leu Glu Ala Asn Leu Leu Trp Gly Ser Thr Ala Thr
    2225            2230            2235
Arg Val Glu Thr Asp Glu Lys Val Ile Ile Leu Asp Ser Phe Glu
    2240            2245            2250
Ser Cys Val Ala Glu Pro Asn Asp Asp Arg Glu Val Ser Val Ala
    2255            2260            2265
Ala Glu Ile Leu Arg Pro Thr Lys Lys Phe Pro Pro Ala Leu Pro
    2270            2275            2280
Ile Trp Ala Arg Pro Asp Tyr Asn Pro Pro Leu Thr Glu Thr Trp
    2285            2290            2295
Lys Gln Gln Asp Tyr Lys Pro Pro Thr Val His Gly Cys Ala Leu
    2300            2305            2310
Pro Pro Gly Lys Gln Pro Pro Val Pro Pro Arg Arg Lys Arg
    2315            2320            2325
Thr Val Gln Leu Thr Glu Ser Val Val Ser Thr Ala Leu Ala Glu
    2330            2335            2340
Leu Ala Ala Lys Thr Phe Gly Gln Ser Glu Pro Ser Ser Asp Arg
    2345            2350            2355
Asp Thr Asp Leu Thr Thr Pro Thr Glu Thr Thr Asp Ser Gly Pro
    2360            2365            2370
Ile Val Val Asp Asp Ala Ser Asp Asp Gly Ser Tyr Ser Ser Met
    2375            2380            2385
Pro Pro Leu Glu Gly Glu Pro Gly Asp Pro Asp Leu Thr Ser Asp
    2390            2395            2400
Ser Trp Ser Thr Val Ser Gly Ser Glu Asp Val Val Cys Cys Ser
    2405            2410            2415
Met Ser Tyr Ser Trp Thr Gly Ala Leu Ile Thr Pro Cys Ser Pro
    2420            2425            2430
Glu Glu Glu Lys Leu Pro Ile Asn Pro Leu Ser Asn Ser Leu Leu
    2435            2440            2445
Arg Tyr His Asn Lys Val Tyr Cys Thr Thr Ser Lys Ser Ala Ser
    2450            2455            2460
Gln Arg Ala Lys Lys Val Thr Phe Asp Arg Thr Gln Val Leu Asp
    2465            2470            2475
Ala His Tyr Asp Ser Val Leu Lys Asp Ile Lys Leu Ala Ala Ser
    2480            2485            2490
Lys Val Ser Ala Arg Leu Leu Thr Leu Glu Glu Ala Cys Gln Leu
    2495            2500            2505
Thr Pro Pro His Ser Ala Arg Ser Lys Tyr Gly Phe Gly Ala Lys
    2510            2515            2520
Glu Val Arg Ser Leu Ser Gly Arg Ala Val Asn His Ile Lys Ser
    2525            2530            2535
Val Trp Lys Asp Leu Leu Glu Asp Pro Gln Thr Pro Ile Pro Thr
    2540            2545            2550
Thr Ile Met Ala Lys Asn Glu Val Phe Cys Val Asp Pro Ala Lys
    2555            2560            2565
Gly Gly Lys Lys Pro Ala Arg Leu Ile Val Tyr Pro Asp Leu Gly
    2570            2575            2580
```

-continued

Val Arg Val Cys Glu Lys Met Ala Leu Tyr Asp Ile Thr Gln Lys
2585                2590                2595

Leu Pro Gln Ala Val Met Gly Ala Ser Tyr Gly Phe Gln Tyr Ser
2600                2605                2610

Pro Ala Gln Arg Val Glu Tyr Leu Leu Lys Ala Trp Ala Glu Lys
2615                2620                2625

Lys Asp Pro Met Gly Phe Ser Tyr Asp Thr Arg Cys Phe Asp Ser
2630                2635                2640

Thr Val Thr Glu Arg Asp Ile Arg Thr Glu Glu Ser Ile Tyr Gln
2645                2650                2655

Ala Cys Ser Leu Pro Glu Glu Ala Arg Thr Ala Ile His Ser Leu
2660                2665                2670

Thr Glu Arg Leu Tyr Val Gly Gly Pro Met Phe Asn Ser Lys Gly
2675                2680                2685

Gln Thr Cys Gly Tyr Arg Arg Cys Arg Ala Ser Gly Val Leu Thr
2690                2695                2700

Thr Ser Met Gly Asn Thr Ile Thr Cys Tyr Val Lys Ala Leu Ala
2705                2710                2715

Ala Cys Lys Ala Ala Gly Ile Val Ala Pro Thr Met Leu Val Cys
2720                2725                2730

Gly Asp Asp Leu Val Val Ile Ser Glu Ser Gln Gly Thr Glu Glu
2735                2740                2745

Asp Glu Arg Asn Leu Arg Ala Phe Thr Glu Ala Met Thr Arg Tyr
2750                2755                2760

Ser Ala Pro Pro Gly Asp Pro Pro Arg Pro Glu Tyr Asp Leu Glu
2765                2770                2775

Leu Ile Thr Ser Cys Ser Ser Asn Val Ser Val Ala Leu Gly Pro
2780                2785                2790

Arg Gly Arg Arg Arg Tyr Tyr Leu Thr Arg Asp Pro Thr Thr Pro
2795                2800                2805

Leu Ala Arg Ala Ala Trp Glu Thr Val Arg His Ser Pro Ile Asn
2810                2815                2820

Ser Trp Leu Gly Asn Ile Ile Gln Tyr Ala Pro Thr Ile Trp Val
2825                2830                2835

Arg Met Val Leu Met Thr His Phe Phe Ser Ile Leu Met Val Gln
2840                2845                2850

Asp Thr Leu Asp Gln Asn Leu Asn Phe Glu Met Tyr Gly Ser Val
2855                2860                2865

Tyr Ser Val Asn Pro Leu Asp Leu Pro Ala Ile Ile Glu Arg Leu
2870                2875                2880

His Gly Leu Asp Ala Phe Ser Met His Thr Tyr Ser His His Glu
2885                2890                2895

Leu Thr Arg Val Ala Ser Ala Leu Arg Lys Leu Gly Ala Pro Pro
2900                2905                2910

Leu Arg Val Trp Lys Ser Arg Ala Arg Ala Val Arg Ala Ser Leu
2915                2920                2925

Ile Ser Arg Gly Gly Lys Ala Ala Val Cys Gly Arg Tyr Leu Phe
2930                2935                2940

Asn Trp Ala Val Lys Thr Lys Leu Lys Leu Thr Pro Leu Pro Glu
2945                2950                2955

Ala Arg Leu Leu Asp Leu Ser Ser Trp Phe Thr Val Gly Ala Gly
2960                2965                2970

Gly Gly Asp Ile Phe His Ser Val Ser Arg Ala Arg Pro Arg Ser
    2975                2980                2985

Leu Leu Phe Gly Leu Leu Leu Phe Val Gly Val Gly Leu Phe
    2990                2995                3000

Leu Leu Pro Ala Arg
    3005

<210> SEQ ID NO 11
<211> LENGTH: 3014
<212> TYPE: PRT
<213> ORGANISM: Hepatitis C virus

<400> SEQUENCE: 11

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Ile Leu Ala Leu Leu Ser Cys Leu Thr Val Pro Thr Ser Ala Val
            180                 185                 190

Pro Tyr Arg Asn Ala Ser Gly Val Tyr His Val Thr Asn Asp Cys Pro
        195                 200                 205

Asn Ser Ser Ile Val Tyr Glu Ala Glu Asp Leu Ile Leu His Ala Pro
    210                 215                 220

Gly Cys Val Pro Cys Val Arg Gln Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Val Phe Leu Val Gly
        275                 280                 285

Gln Met Phe Thr Tyr Gly Pro Arg Arg His Asn Val Val Gln Asp Cys
    290                 295                 300

Asn Cys Ser Ile Tyr Ser Gly His Ile Thr Gly His Arg Met Ala Trp
305                 310                 315                 320

Asp Met Met Met Asn Trp Ser Pro Thr Thr Ala Leu Val Met Ala Gln
                325                 330                 335

-continued

```
Leu Leu Arg Ile Pro Gln Val Ile Asp Ile Ile Ala Gly Ala His
            340                 345                 350

Trp Gly Val Leu Phe Ala Ala Tyr Tyr Ala Ser Ala Ala Asn Trp
            355                 360                 365

Ala Lys Val Val Leu Val Leu Phe Leu Phe Ala Gly Val Asp Ala Ser
    370                 375                 380

Thr Arg Thr Val Gly Gly Ser Ala Ala Gln Gly Ala Arg Gly Leu Ala
385                 390                 395                 400

Ser Leu Phe Thr Pro Gly Pro Gln Gln Asn Leu Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Val Ala Gly Leu Leu Tyr Tyr His Lys Phe Asn
                435                 440                 445

Ser Thr Gly Cys Pro Gln Arg Met Ala Ser Cys Arg Pro Leu Ala Ala
    450                 455                 460

Phe Asp Gln Gly Trp Gly Thr Ile Ser Tyr Ala Ala Val Ser Gly Pro
465                 470                 475                 480

Ser Asp Asp Lys Pro Tyr Cys Trp His Tyr Pro Pro Arg Pro Cys Gly
                485                 490                 495

Ile Val Pro Ala Arg Gly Val Cys Gly Pro Val Tyr Cys Phe Thr Pro
                500                 505                 510

Ser Pro Val Val Gly Thr Thr Asp Arg Lys Gly Asn Pro Thr Tyr
    515                 520                 525

Ser Trp Gly Glu Asn Glu Thr Asp Ile Phe Leu Leu Asn Asn Thr Arg
                530                 535                 540

Pro Pro Thr Gly Asn Trp Phe Gly Cys Thr Trp Met Asn Ser Thr Gly
545                 550                 555                 560

Phe Val Lys Thr Cys Gly Ala Pro Pro Cys Asn Leu Gly Pro Thr Gly
                565                 570                 575

Asn Asn Ser Leu Lys Cys Pro Thr Asp Cys Phe Arg Lys His Pro Asp
                580                 585                 590

Ala Thr Tyr Thr Lys Cys Gly Ser Gly Pro Trp Leu Thr Pro Arg Cys
                595                 600                 605

Leu Val His Tyr Pro Tyr Arg Leu Trp His Tyr Pro Cys Thr Leu Asn
                610                 615                 620

Tyr Thr Ile Phe Lys Val Arg Met Tyr Ile Gly Gly Leu Glu His Arg
625                 630                 635                 640

Leu Glu Val Ala Cys Asn Trp Thr Arg Gly Glu Arg Cys Asp Leu Glu
                645                 650                 655

Asp Arg Asp Arg Ala Glu Leu Ser Pro Leu Leu His Thr Thr Thr Gln
                660                 665                 670

Trp Ala Ile Leu Pro Cys Ser Phe Thr Pro Thr Pro Ala Leu Ser Thr
                675                 680                 685

Gly Leu Ile His Leu His Gln Asn Ile Val Asp Thr Gln Tyr Leu Tyr
                690                 695                 700

Gly Leu Ser Ser Ser Ile Val Ser Trp Ala Val Lys Trp Glu Tyr Ile
705                 710                 715                 720

Val Leu Ala Phe Leu Leu Leu Ala Asp Ala Arg Ile Cys Thr Cys Leu
                725                 730                 735

Trp Ile Met Leu Leu Val Cys Gln Ala Glu Ala Ala Leu Glu Asn Val
                740                 745                 750
```

-continued

```
Ile Val Leu Asn Ala Ala Ala Ala Gly Thr His Gly Phe Phe Trp
            755             760             765
Gly Leu Leu Val Ile Cys Phe Ala Trp His Phe Lys Gly Arg Leu Val
        770             775             780
Pro Gly Ala Thr Tyr Leu Cys Leu Gly Ile Trp Pro Leu Leu Leu
785             790             795             800
Leu Phe Leu Leu Pro Gln Arg Ala Leu Ala Leu Asp Ser Ser Asp Gly
                805             810             815
Gly Thr Val Gly Cys Leu Val Leu Thr Ile Leu Thr Ile Phe Thr Leu
            820             825             830
Thr Pro Gly Tyr Lys Lys Met Val Val Leu Val Ile Trp Trp Leu Gln
        835             840             845
Tyr Phe Ile Ala Arg Val Glu Ala Phe Ile His Val Trp Val Pro Pro
850             855             860
Leu Gln Val Arg Gly Gly Arg Asp Ala Ile Ile Met Leu Thr Cys Leu
865             870             875             880
Phe His Pro Ala Leu Gly Phe Glu Val Thr Lys Ile Leu Leu Gly Ile
                885             890             895
Leu Gly Pro Leu Tyr Leu Leu Gln Tyr Ser Leu Ile Lys Leu Pro Tyr
            900             905             910
Phe Ile Arg Ala Arg Ala Leu Leu Arg Ala Cys Leu Leu Ala Lys His
        915             920             925
Leu Ala Cys Gly Arg Tyr Val Gln Ala Ala Leu Leu His Leu Gly Arg
930             935             940
Leu Thr Gly Thr Tyr Ile Tyr Asp His Leu Ala Pro Met Lys Asp Trp
945             950             955             960
Ala Ala Ser Gly Leu Arg Asp Leu Ala Val Ala Thr Glu Pro Ile Ile
                965             970             975
Phe Ser Pro Met Glu Thr Lys Val Ile Thr Trp Gly Ala Asp Thr Ala
            980             985             990
Ala Cys Gly Asp Ile Leu Ala Gly Leu Pro Val Ser Ala Arg Arg Gly
        995             1000            1005
His Glu Ile Phe Leu Gly Pro Ala Asp Asp Ile Arg Glu Ala Gly
    1010            1015            1020
Trp Arg Leu Leu Ala Pro Ile Thr Ala Tyr Ala Gln Gln Thr Arg
    1025            1030            1035
Gly Val Leu Gly Ala Ile Ile Val Ser Leu Thr Gly Arg Asp Lys
    1040            1045            1050
Asn Glu Ala Glu Gly Glu Val Gln Val Leu Ser Thr Ala Thr Gln
    1055            1060            1065
Thr Phe Leu Gly Thr Cys Ile Asn Gly Val Met Trp Thr Val Phe
    1070            1075            1080
His Gly Ala Gly Ser Lys Thr Leu Ala Gly Pro Lys Gly Pro Val
    1085            1090            1095
Val Gln Met Tyr Thr Asn Val Asp Lys Asp Leu Val Gly Trp Pro
    1100            1105            1110
Thr Pro Pro Gly Thr Arg Ser Leu Thr Pro Cys Thr Cys Gly Ser
    1115            1120            1125
Ala Asp Leu Tyr Leu Val Thr Arg His Ala Asp Val Val Pro Ala
    1130            1135            1140
Arg Arg Arg Gly Asp Thr Arg Ala Ser Leu Leu Ser Pro Arg Pro
    1145            1150            1155
Ile Ser Tyr Leu Lys Gly Ser Ser Gly Gly Pro Val Met Cys Pro
```

-continued

```
            1160                1165                1170

Ser  Gly  His  Val  Val  Gly  Val  Phe  Arg  Ala  Ala  Val  Cys  Thr  Arg
     1175                1180                1185

Gly  Val  Ala  Lys  Ala  Leu  Asp  Phe  Ile  Pro  Val  Glu  Asn  Leu  Glu
     1190                1195                1200

Thr  Thr  Met  Arg  Ser  Pro  Val  Phe  Thr  Asp  Asn  Ser  Thr  Pro  Pro
     1205                1210                1215

Ala  Val  Pro  His  Glu  Phe  Gln  Val  Gly  His  Leu  His  Ala  Pro  Thr
     1220                1225                1230

Gly  Ser  Gly  Lys  Ser  Thr  Lys  Val  Pro  Ala  Ala  Tyr  Ala  Ala  Gln
     1235                1240                1245

Gly  Tyr  Lys  Val  Leu  Val  Leu  Asn  Pro  Ser  Val  Ala  Ala  Thr  Leu
     1250                1255                1260

Gly  Phe  Gly  Ala  Tyr  Met  Ser  Arg  Ala  Tyr  Gly  Val  Asp  Pro  Asn
     1265                1270                1275

Ile  Arg  Thr  Gly  Val  Arg  Thr  Val  Thr  Thr  Gly  Ala  Ala  Ile  Thr
     1280                1285                1290

Tyr  Ser  Thr  Tyr  Gly  Lys  Phe  Leu  Ala  Asp  Gly  Gly  Cys  Ser  Gly
     1295                1300                1305

Gly  Ala  Tyr  Asp  Val  Ile  Ile  Cys  Asp  Glu  Cys  His  Ser  Gln  Asp
     1310                1315                1320

Ala  Thr  Thr  Ile  Leu  Gly  Ile  Gly  Thr  Val  Leu  Asp  Gln  Ala  Glu
     1325                1330                1335

Thr  Ala  Gly  Ala  Arg  Leu  Val  Val  Leu  Ala  Thr  Ala  Thr  Pro  Pro
     1340                1345                1350

Gly  Ser  Val  Thr  Thr  Pro  His  Pro  Asn  Ile  Glu  Glu  Val  Ala  Leu
     1355                1360                1365

Pro  Ser  Glu  Gly  Glu  Ile  Pro  Phe  Tyr  Gly  Arg  Ala  Ile  Pro  Leu
     1370                1375                1380

Ala  Leu  Ile  Lys  Gly  Gly  Arg  His  Leu  Ile  Phe  Cys  His  Ser  Lys
     1385                1390                1395

Lys  Lys  Cys  Asp  Glu  Leu  Ala  Lys  Gln  Leu  Thr  Ser  Gln  Gly  Val
     1400                1405                1410

Asn  Ala  Val  Ala  Tyr  Tyr  Arg  Gly  Leu  Asp  Val  Ala  Val  Ile  Pro
     1415                1420                1425

Ala  Thr  Gly  Asp  Val  Val  Val  Cys  Ser  Thr  Asp  Ala  Leu  Met  Thr
     1430                1435                1440

Gly  Phe  Thr  Gly  Asp  Phe  Asp  Ser  Val  Ile  Asp  Cys  Asn  Thr  Thr
     1445                1450                1455

Val  Thr  Gln  Thr  Val  Asp  Leu  Ser  Leu  Asp  Pro  Thr  Phe  Thr  Ile
     1460                1465                1470

Glu  Thr  Thr  Thr  Val  Pro  Gln  Asp  Ala  Val  Ser  Arg  Ser  Gln  Arg
     1475                1480                1485

Arg  Gly  Arg  Thr  Gly  Arg  Gly  Arg  His  Gly  Ile  Tyr  Arg  Tyr  Val
     1490                1495                1500

Ser  Ser  Gly  Glu  Arg  Pro  Ser  Gly  Ile  Phe  Asp  Ser  Val  Val  Leu
     1505                1510                1515

Cys  Glu  Cys  Tyr  Asp  Ala  Gly  Cys  Ala  Trp  Tyr  Asp  Leu  Thr  Pro
     1520                1525                1530

Ala  Glu  Thr  Thr  Val  Arg  Leu  Arg  Ala  Tyr  Leu  Asn  Thr  Pro  Gly
     1535                1540                1545

Leu  Pro  Val  Phe  Gln  Asp  His  Leu  Glu  Phe  Trp  Glu  Gly  Val  Phe
     1550                1555                1560
```

```
Thr Gly Leu Thr Asn Ile Asp Ala His Met Leu Ser Gln Thr Lys
    1565             1570             1575

Gln Gly Gly Glu Asn Phe Pro Tyr Leu Val Ala Tyr Gln Ala Thr
    1580             1585             1590

Val Cys Val Arg Ala Lys Ala Pro Pro Pro Ser Trp Asp Thr Met
    1595             1600             1605

Trp Lys Cys Met Leu Arg Leu Lys Pro Thr Leu Thr Gly Pro Thr
    1610             1615             1620

Pro Leu Leu Tyr Arg Leu Gly Ala Val Gln Asn Glu Ile Thr Leu
    1625             1630             1635

Thr His Pro Ile Thr Lys Tyr Ile Met Ala Cys Met Ser Ala Asp
    1640             1645             1650

Leu Glu Val Ile Thr Ser Thr Trp Val Leu Val Gly Gly Val Val
    1655             1660             1665

Ala Ala Leu Ala Ser Tyr Cys Leu Thr Val Gly Ser Val Ala Ile
    1670             1675             1680

Val Gly Arg Ile Ile Leu Ser Gly Arg Pro Ala Ile Ile Pro Asp
    1685             1690             1695

Arg Glu Val Leu Tyr Gln Gln Phe Asp Glu Met Glu Glu Cys Ser
    1700             1705             1710

Ala Ser Leu Pro Tyr Met Asp Glu Ala Arg Ala Ile Ala Glu Gln
    1715             1720             1725

Phe Lys Glu Lys Val Leu Gly Leu Ile Gly Thr Ala Gly Gln Lys
    1730             1735             1740

Ala Glu Thr Leu Lys Pro Ala Ala Thr Ser Met Trp Asn Arg Ala
    1745             1750             1755

Glu Gln Phe Trp Ala Lys His Met Trp Asn Phe Val Ser Gly Ile
    1760             1765             1770

Gln Tyr Leu Ala Gly Leu Ser Thr Leu Pro Gly Asn Pro Ala Val
    1775             1780             1785

Ala Thr Leu Met Ser Phe Thr Ala Ala Val Thr Ser Pro Leu Thr
    1790             1795             1800

Thr Gln Gln Thr Leu Leu Phe Asn Ile Leu Gly Gly Trp Val Ala
    1805             1810             1815

Ser Gln Ile Ala Pro Pro Thr Ala Ala Thr Ala Phe Val Val Ser
    1820             1825             1830

Gly Leu Ala Gly Ala Ala Val Gly Ser Ile Gly Leu Gly Arg Val
    1835             1840             1845

Leu Ile Asp Ile Leu Ala Gly Tyr Gly Ala Gly Val Ala Gly Ala
    1850             1855             1860

Leu Val Ala Phe Lys Ile Met Cys Gly Glu Lys Pro Thr Ala Glu
    1865             1870             1875

Asp Leu Val Asn Leu Leu Pro Ser Ile Leu Cys Pro Gly Ala Leu
    1880             1885             1890

Val Val Gly Val Ile Cys Ala Ala Val Leu Arg Arg His Ile Gly
    1895             1900             1905

Pro Gly Glu Gly Ala Val Gln Trp Met Asn Arg Leu Ile Ala Phe
    1910             1915             1920

Ala Ser Arg Gly Asn His Val Ser Pro Thr His Tyr Val Pro Glu
    1925             1930             1935

Thr Asp Ala Ser Ala Lys Val Thr Gln Leu Leu Ser Ser Leu Thr
    1940             1945             1950
```

```
Val Thr Ser Leu Leu Lys Arg Leu His Thr Trp Ile Gly Glu Asp
1955                1960                1965

Tyr Ser Thr Pro Cys Asp Gly Thr Trp Leu Arg Ala Ile Trp Asp
1970                1975                1980

Trp Val Cys Thr Ala Leu Thr Asp Phe Lys Ala Trp Leu Gln Ala
1985                1990                1995

Lys Leu Leu Pro Gln Leu Pro Gly Val Pro Phe Leu Ser Cys Gln
2000                2005                2010

Arg Gly Tyr Lys Gly Val Trp Arg Gly Asp Gly Val Asn Ser Thr
2015                2020                2025

Lys Cys Pro Cys Gly Ala Thr Ile Ser Gly His Val Lys Asn Gly
2030                2035                2040

Thr Met Arg Ile Val Gly Pro Lys Leu Cys Ser Asn Thr Trp His
2045                2050                2055

Gly Thr Phe Pro Ile Asn Ala Thr Thr Thr Gly Pro Ser Val Pro
2060                2065                2070

Ala Pro Ala Pro Asn Tyr Lys Phe Ala Leu Trp Arg Val Gly Ala
2075                2080                2085

Ala Asp Tyr Ala Glu Val Arg Arg Val Gly Asp Tyr His Tyr Ile
2090                2095                2100

Thr Gly Val Thr Gln Asp Asn Leu Lys Cys Pro Cys Gln Val Pro
2105                2110                2115

Ser Pro Glu Phe Phe Thr Glu Leu Asp Gly Val Arg Ile His Arg
2120                2125                2130

Tyr Ala Pro Pro Cys Asn Pro Leu Leu Arg Glu Glu Val Cys Phe
2135                2140                2145

Ser Val Gly Leu His Ser Phe Val Val Gly Ser Gln Leu Pro Cys
2150                2155                2160

Glu Pro Glu Pro Asp Val Thr Val Leu Thr Ser Met Leu Ser Asp
2165                2170                2175

Pro Ala His Ile Thr Ala Glu Thr Ala Lys Arg Arg Leu Asp Arg
2180                2185                2190

Gly Ser Pro Pro Ser Leu Ala Ser Ser Ser Ala Ser Gln Leu Ser
2195                2200                2205

Ala Pro Ser Leu Lys Ala Thr Cys Thr Thr Gln Gly His His Pro
2210                2215                2220

Asp Ala Asp Leu Ile Glu Ala Asn Leu Leu Trp Arg Gln Cys Met
2225                2230                2235

Gly Gly Asn Ile Thr Arg Val Glu Ala Glu Asn Lys Val Val Ile
2240                2245                2250

Leu Asp Ser Phe Glu Pro Leu Lys Ala Asp Asp Asp Arg Glu
2255                2260                2265

Ile Ser Val Ser Ala Asp Cys Phe Arg Arg Gly Pro Ala Phe Pro
2270                2275                2280

Pro Ala Leu Pro Val Trp Ala Arg Pro Gly Tyr Asp Pro Pro Leu
2285                2290                2295

Leu Glu Thr Trp Lys Gln Pro Asp Tyr Asp Pro Pro Gln Val Ser
2300                2305                2310

Gly Cys Pro Leu Pro Pro Ala Gly Leu Pro Pro Val Pro Pro Pro
2315                2320                2325

Arg Arg Lys Arg Lys Pro Val Val Leu Ser Asp Ser Asn Val Ser
2330                2335                2340

Gln Val Leu Ala Asp Leu Ala His Ala Arg Phe Lys Ala Asp Thr
```

```
            2345                2350                2355
Gln Ser Ile Glu Gly Gln Asp Ser Ala Val Gly Thr Ser Ser Gln
        2360                2365                2370
Pro Asp Ser Gly Pro Glu Glu Lys Arg Asp Asp Ser Asp Ala
        2375                2380                2385
Ala Ser Tyr Ser Ser Met Pro Pro Leu Glu Gly Glu Pro Gly Asp
        2390                2395                2400
Pro Asp Leu Ser Ser Gly Ser Trp Ser Thr Val Ser Asp Glu Asp
        2405                2410                2415
Ser Val Val Cys Cys Ser Met Ser Tyr Ser Trp Thr Gly Ala Leu
        2420                2425                2430
Ile Thr Pro Cys Ser Pro Glu Glu Lys Leu Pro Ile Asn Pro
        2435                2440                2445
Leu Ser Asn Ser Leu Leu Arg Tyr His Asn Lys Val Tyr Cys Thr
        2450                2455                2460
Thr Ser Lys Ser Ala Ser Gln Arg Ala Lys Lys Val Thr Phe Asp
        2465                2470                2475
Arg Thr Gln Val Leu Asp Ala His Tyr Asp Ser Val Leu Lys Asp
        2480                2485                2490
Ile Lys Leu Ala Ala Ser Lys Val Ser Ala Arg Leu Leu Thr Leu
        2495                2500                2505
Glu Glu Ala Cys Gln Leu Thr Pro Pro His Ser Ala Arg Ser Lys
        2510                2515                2520
Tyr Gly Phe Gly Ala Lys Glu Val Arg Ser Leu Ser Gly Arg Ala
        2525                2530                2535
Val Asn His Ile Lys Ser Val Trp Lys Asp Leu Leu Glu Asp Pro
        2540                2545                2550
Gln Thr Pro Ile Pro Thr Thr Ile Met Ala Lys Asn Glu Val Phe
        2555                2560                2565
Cys Val Asp Pro Ala Lys Gly Gly Lys Lys Pro Ala Arg Leu Ile
        2570                2575                2580
Val Tyr Pro Asp Leu Gly Val Arg Val Cys Glu Lys Met Ala Leu
        2585                2590                2595
Tyr Asp Ile Thr Gln Lys Leu Pro Gln Ala Val Met Gly Ala Ser
        2600                2605                2610
Tyr Gly Phe Gln Tyr Ser Pro Ala Gln Arg Val Glu Tyr Leu Leu
        2615                2620                2625
Lys Ala Trp Ala Glu Lys Lys Asp Pro Met Gly Phe Ser Tyr Asp
        2630                2635                2640
Thr Arg Cys Phe Asp Ser Thr Val Thr Glu Arg Asp Ile Arg Thr
        2645                2650                2655
Glu Glu Ser Ile Tyr Gln Ala Cys Ser Leu Pro Glu Glu Ala Arg
        2660                2665                2670
Thr Ala Ile His Ser Leu Thr Glu Arg Leu Tyr Val Gly Gly Pro
        2675                2680                2685
Met Phe Asn Ser Lys Gly Gln Thr Cys Gly Tyr Arg Arg Cys Arg
        2690                2695                2700
Ala Ser Gly Val Leu Thr Thr Ser Met Gly Asn Thr Ile Thr Cys
        2705                2710                2715
Tyr Val Lys Ala Leu Ala Ala Cys Lys Ala Ala Gly Ile Val Ala
        2720                2725                2730
Pro Thr Met Leu Val Cys Gly Asp Asp Leu Val Val Ile Ser Glu
        2735                2740                2745
```

Ser Gln Gly Thr Glu Glu Asp Glu Arg Asn Leu Arg Ala Phe Thr
    2750                2755                2760

Glu Ala Met Thr Arg Tyr Ser Ala Pro Pro Gly Asp Pro Pro Arg
    2765                2770                2775

Pro Glu Tyr Asp Leu Glu Leu Ile Thr Ser Cys Ser Ser Asn Val
    2780                2785                2790

Ser Val Ala Leu Gly Pro Arg Gly Arg Arg Tyr Tyr Leu Thr
    2795                2800                2805

Arg Asp Pro Thr Thr Pro Leu Ala Arg Ala Ala Trp Glu Thr Val
    2810                2815                2820

Arg His Ser Pro Ile Asn Ser Trp Leu Gly Asn Ile Ile Gln Tyr
    2825                2830                2835

Ala Pro Thr Ile Trp Val Arg Met Val Leu Met Thr His Phe Phe
    2840                2845                2850

Ser Ile Leu Met Val Gln Asp Thr Leu Asp Gln Asn Leu Asn Phe
    2855                2860                2865

Glu Met Tyr Gly Ser Val Tyr Ser Val Asn Pro Leu Asp Leu Pro
    2870                2875                2880

Ala Ile Ile Glu Arg Leu His Gly Leu Asp Ala Phe Ser Met His
    2885                2890                2895

Thr Tyr Ser His His Glu Leu Thr Arg Val Ala Ser Ala Leu Arg
    2900                2905                2910

Lys Leu Gly Ala Pro Pro Leu Arg Val Trp Lys Ser Arg Ala Arg
    2915                2920                2925

Ala Val Arg Ala Ser Leu Ile Ser Arg Gly Gly Lys Ala Ala Val
    2930                2935                2940

Cys Gly Arg Tyr Leu Phe Asn Trp Ala Val Lys Thr Lys Leu Lys
    2945                2950                2955

Leu Thr Pro Leu Pro Glu Ala Arg Leu Leu Asp Leu Ser Ser Trp
    2960                2965                2970

Phe Thr Val Gly Ala Gly Gly Gly Ile Phe His Ser Val Ser
    2975                2980                2985

Arg Ala Arg Pro Arg Ser Leu Leu Phe Gly Leu Leu Leu Leu Phe
    2990                2995                3000

Val Gly Val Gly Leu Phe Leu Leu Pro Ala Arg
    3005                3010

<210> SEQ ID NO 12
<211> LENGTH: 3020
<212> TYPE: PRT
<213> ORGANISM: Hepatitis C virus

<400> SEQUENCE: 12

Met Ser Thr Leu Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Gln Gly Arg His Trp Ala Gln Pro Gly
65                  70                  75                  80

Tyr Pro Trp Pro Leu Tyr Gly Asn Glu Gly Cys Gly Trp Ala Gly Trp

```
                       85                  90                  95
Leu Leu Ser Pro Arg Gly Ser Arg Pro His Trp Gly Pro Asn Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Val Val Gly Ala Pro Leu
                130                 135                 140

Gly Gly Val Ala Ala Leu Ala His Gly Val Arg Ala Ile Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser Ala Leu
                180                 185                 190

Thr Tyr Gly Asn Ser Ser Gly Leu Tyr His Leu Thr Asn Asp Cys Pro
                195                 200                 205

Asn Ser Ser Ile Val Leu Glu Ala Asp Ala Met Ile Leu His Leu Pro
                210                 215                 220

Gly Cys Leu Pro Cys Val Arg Val Asn Asn Asn Gln Ser Ile Cys Trp
225                 230                 235                 240

His Ala Val Ser Pro Thr Leu Ala Ile Pro Asn Ala Ser Thr Pro Ala
                245                 250                 255

Thr Gly Phe Arg Arg His Val Asp Leu Leu Ala Gly Ala Ala Val Val
                260                 265                 270

Cys Ser Ser Leu Tyr Ile Gly Asp Leu Cys Gly Ser Leu Phe Leu Ala
                275                 280                 285

Gly Gln Leu Phe Thr Phe Gln Pro Arg Arg His Trp Thr Val Gln Asp
                290                 295                 300

Cys Asn Cys Ser Ile Tyr Thr Gly His Val Thr Gly His Arg Met Ala
305                 310                 315                 320

Trp Asp Met Met Met Asn Trp Ser Pro Thr Thr Thr Leu Val Leu Ser
                325                 330                 335

Ser Ile Leu Arg Val Pro Glu Ile Cys Ala Ser Val Ile Phe Gly Gly
                340                 345                 350

His Trp Gly Ile Leu Leu Ala Val Ala Tyr Phe Gly Met Ala Gly Asn
                355                 360                 365

Trp Leu Lys Val Leu Ala Val Leu Phe Leu Phe Ala Gly Val Glu Ala
                370                 375                 380

Thr Thr Ile Ile Gly His Gln Val Gly Arg Thr Thr Gly Gly Leu Ala
385                 390                 395                 400

Ser Leu Phe Ser Ile Gly Pro Arg Gln Asn Leu Gln Leu Ile Asn Thr
                405                 410                 415

Asn Gly Ser Trp His Ile Asn Arg Thr Ala Leu Asn Cys Asn Asp Ser
                420                 425                 430

Leu Gln Thr Gly Phe Ile Thr Ser Leu Phe Tyr Ala Lys Asn Val Asn
                435                 440                 445

Ser Ser Gly Cys Pro Glu Arg Met Ala Ala Cys Lys Pro Leu Ala Asp
                450                 455                 460

Phe Arg Gln Gly Trp Gly Gln Ile Thr Tyr Lys Val Asn Ile Ser Gly
465                 470                 475                 480

Pro Ser Asp Asp Arg Pro Tyr Cys Trp His Tyr Ala Pro Arg Pro Cys
                485                 490                 495

Asp Val Val Ser Ala Arg Thr Val Cys Gly Pro Val Tyr Cys Phe Thr
                500                 505                 510
```

```
Pro Ser Pro Val Val Gly Thr Thr Asp Lys Leu Gly Ile Pro Thr
    515                 520                 525

Tyr Asn Trp Gly Glu Asn Glu Thr Asp Val Phe Met Leu Glu Ser Leu
    530                 535                 540

Arg Pro Pro Thr Gly Gly Trp Phe Gly Cys Thr Trp Met Asn Ser Thr
545                 550                 555                 560

Gly Phe Thr Lys Thr Cys Gly Ala Pro Pro Cys Gln Ile Val Pro Gly
                565                 570                 575

Asp Tyr Asn Ser Ser Ala Asn Glu Leu Leu Cys Pro Thr Asp Cys Phe
                580                 585                 590

Arg Lys His Pro Glu Ala Thr Tyr Gln Arg Cys Gly Ser Gly Pro Trp
                595                 600                 605

Ile Thr Pro Arg Cys Leu Val Asp Tyr Pro Tyr Arg Leu Trp His Tyr
                610                 615                 620

Pro Cys Thr Val Asn Phe Thr Leu His Lys Val Arg Met Phe Val Gly
625                 630                 635                 640

Gly Ile Glu His Arg Phe Asp Ala Ala Cys Asn Trp Thr Arg Gly Glu
                645                 650                 655

Arg Cys Asp Leu His Asp Arg Asp Arg Ile Glu Met Ser Pro Leu Leu
                660                 665                 670

Phe Ser Thr Thr Gln Leu Ala Ile Leu Pro Cys Ser Phe Ser Thr Met
        675                 680                 685

Pro Ala Leu Ser Thr Gly Leu Ile His Leu His Gln Asn Ile Val Asp
690                 695                 700

Val Gln Tyr Leu Tyr Gly Val Ser Ser Val Thr Ser Trp Val Val
705                 710                 715                 720

Lys Trp Glu Tyr Ile Val Leu Val Phe Leu Val Leu Ala Asp Ala Arg
                725                 730                 735

Ile Cys Thr Cys Leu Trp Leu Met Leu Leu Ile Thr Asn Val Glu Ala
                740                 745                 750

Ala Val Glu Arg Leu Val Val Leu Asn Ala Ala Ser Ala Ala Gly Thr
        755                 760                 765

Ala Gly Trp Trp Trp Ala Val Leu Phe Leu Cys Cys Ala Trp Tyr Val
        770                 775                 780

Lys Gly Arg Leu Val Pro Ala Cys Thr Tyr Met Ala Leu Gly Met Trp
785                 790                 795                 800

Pro Leu Leu Leu Thr Ile Leu Ala Leu Pro Arg Arg Ala Tyr Ala Met
                805                 810                 815

Asp Asn Glu Gln Ala Ala Ser Leu Gly Ala Val Gly Leu Leu Val Leu
                820                 825                 830

Thr Ile Phe Thr Ile Thr Pro Met Tyr Lys Lys Leu Leu Thr Cys Ser
                835                 840                 845

Ile Trp Trp Asn Gln Tyr Phe Leu Ala Arg Ala Glu Ala Met Ile His
                850                 855                 860

Glu Trp Val Pro Asp Leu Arg Val Arg Gly Arg Asp Pro Ile Ile
865                 870                 875                 880

Leu Leu Thr Cys Leu Leu His Pro Gln Leu Gly Phe Glu Val Thr Lys
                885                 890                 895

Ile Leu Leu Ala Ile Leu Ala Pro Leu Tyr Ile Leu Gln Tyr Ser Leu
                900                 905                 910

Leu Lys Val Pro Tyr Phe Val Arg Ala His Val Leu Leu Arg Ala Cys
                915                 920                 925
```

```
Leu Leu Val Arg Arg Leu Ala Gly Gly Lys Tyr Val Gln Ala Cys Leu
930                 935                 940

Leu Arg Leu Gly Ala Trp Thr Gly Thr Phe Val Tyr Asp His Leu Ala
945                 950                 955                 960

Pro Leu Ser Asp Trp Ala Ser Asp Gly Leu Arg Asp Leu Ala Val Ala
                965                 970                 975

Ile Glu Pro Val Ile Phe Ser Pro Met Glu Lys Lys Ile Ile Thr Trp
                980                 985                 990

Gly Ala Asp Thr Ala Ala Cys Gly Asp Ile Leu Ser Gly Leu Pro Val
            995                 1000                1005

Ser Ala Arg Leu Gly Asn Leu Val Leu Leu Gly Pro Ala Asp Asp
    1010                1015                1020

Met Gln Arg Gly Gly Trp Lys Leu Leu Ala Pro Ile Thr Ala Tyr
    1025                1030                1035

Ala Gln Gln Thr Arg Gly Leu Val Gly Thr Ile Val Thr Ser Leu
    1040                1045                1050

Thr Gly Arg Asp Lys Asn Glu Val Glu Gly Glu Val Gln Val Val
    1055                1060                1065

Ser Thr Ala Thr Gln Ser Phe Leu Ala Thr Ser Ile Asn Gly Val
    1070                1075                1080

Met Trp Thr Val Tyr His Gly Ala Gly Ser Lys Thr Leu Ala Gly
    1085                1090                1095

Pro Lys Gly Pro Val Cys Gln Met Tyr Thr Asn Val Asp Lys Asp
    1100                1105                1110

Leu Val Gly Trp Pro Ser Pro Gly Ala Arg Ser Leu Thr Pro
    1115                1120                1125

Cys Thr Cys Gly Ser Ser Asp Leu Tyr Leu Val Thr Arg Glu Ala
    1130                1135                1140

Asp Val Ile Pro Ala Arg Arg Arg Gly Asp Asn Arg Ala Ala Leu
    1145                1150                1155

Leu Ser Pro Arg Pro Ile Ser Thr Leu Lys Gly Ser Ser Gly Gly
    1160                1165                1170

Pro Ile Met Cys Pro Ser Gly His Val Val Gly Leu Phe Arg Ala
    1175                1180                1185

Ala Val Cys Thr Arg Gly Val Ala Lys Ser Leu Asp Phe Ile Pro
    1190                1195                1200

Val Glu Asn Met Glu Thr Thr Met Arg Ser Pro Ser Phe Thr Asp
    1205                1210                1215

Asn Ser Thr Pro Pro Ala Val Pro Gln Thr Tyr Gln Val Gly Tyr
    1220                1225                1230

Leu His Ala Pro Thr Gly Ser Gly Lys Ser Thr Arg Val Pro Ala
    1235                1240                1245

Ala Tyr Ala Ser Gln Gly Tyr Lys Val Leu Val Leu Asn Pro Ser
    1250                1255                1260

Val Ala Ala Thr Leu Ser Phe Gly Ser Tyr Met Arg Gln Ala Tyr
    1265                1270                1275

Gly Val Glu Pro Asn Ile Arg Thr Gly Val Arg Thr Val Thr Thr
    1280                1285                1290

Gly Gly Ala Ile Thr Tyr Ser Thr Tyr Gly Lys Phe Leu Ala Asp
    1295                1300                1305

Gly Gly Cys Ser Gly Gly Ala Tyr Asp Ile Ile Ile Cys Asp Glu
    1310                1315                1320

Cys His Ser Thr Asp Pro Thr Thr Val Leu Gly Ile Gly Thr Val
```

```
              1325                1330                1335

Leu Asp Gln Ala Glu Thr Ala Gly Val Arg Leu Thr Val Leu Ala
        1340                1345                1350

Thr Ala Thr Pro Pro Gly Ser Val Thr Val Pro His Pro Asn Ile
        1355                1360                1365

Thr Glu Thr Ala Leu Pro Thr Thr Gly Glu Ile Pro Phe Tyr Gly
        1370                1375                1380

Lys Gly Ile Pro Leu Glu Tyr Ile Lys Gly Gly Arg His Leu Ile
        1385                1390                1395

Phe Cys His Ser Lys Lys Lys Cys Asp Glu Leu Ala Gly Lys Leu
        1400                1405                1410

Lys Ser Leu Gly Leu Asn Ala Val Ala Phe Tyr Arg Gly Val Asp
        1415                1420                1425

Val Ser Val Ile Pro Thr Ser Gly Asp Val Val Cys Ala Thr
        1430                1435                1440

Asp Ala Leu Met Thr Gly Tyr Thr Gly Asp Phe Asp Ser Val Ile
        1445                1450                1455

Asp Cys Asn Val Ala Val Thr Gln Val Val Asp Leu Ser Leu Asp
        1460                1465                1470

Pro Thr Phe Ser Ile Glu Thr Thr Ile Val Pro Gln Asp Ala Val
        1475                1480                1485

Ser Arg Ser Gln Arg Arg Gly Arg Thr Gly Arg Gly Lys Pro Gly
        1490                1495                1500

Val Tyr Arg Phe Val Ser Gln Gly Glu Arg Pro Ser Gly Met Phe
        1505                1510                1515

Asp Thr Val Val Leu Cys Glu Ala Tyr Asp Thr Gly Cys Ala Trp
        1520                1525                1530

Tyr Glu Leu Thr Pro Ser Glu Thr Thr Val Arg Leu Arg Ala Tyr
        1535                1540                1545

Leu Asn Thr Pro Gly Leu Pro Leu Cys Gln Asp His Leu Glu Phe
        1550                1555                1560

Trp Glu Gly Val Phe Thr Gly Leu Thr His Ile Asp Ala His Phe
        1565                1570                1575

Leu Ser Gln Thr Lys Gln Gly Gly Glu Asn Phe Ala Tyr Leu Val
        1580                1585                1590

Ala Tyr Gln Ala Thr Val Cys Ala Arg Ala Lys Ala Pro Pro Pro
        1595                1600                1605

Ser Trp Asp Thr Met Trp Lys Cys Leu Ile Arg Leu Lys Pro Thr
        1610                1615                1620

Leu Thr Gly Pro Thr Pro Leu Leu Tyr Arg Leu Gly Ala Val Gln
        1625                1630                1635

Asn Glu Ile Ile Thr Thr His Pro Ile Thr Lys Tyr Ile Met Thr
        1640                1645                1650

Cys Met Ser Ala Asp Leu Glu Val Ile Thr Ser Thr Trp Val Leu
        1655                1660                1665

Val Gly Gly Val Leu Ala Ala Leu Ala Ser Tyr Cys Leu Ser Val
        1670                1675                1680

Gly Cys Val Val Ile Cys Gly Arg Val Thr Leu Thr Gly Lys Pro
        1685                1690                1695

Ala Val Val Pro Asp Arg Glu Ile Leu Tyr Gln Gln Phe Asp Glu
        1700                1705                1710

Met Glu Glu Cys Ser Arg His Ile Pro Tyr Leu Ala Glu Gly Gln
        1715                1720                1725
```

```
Gln Ile Ala Glu Gln Phe Arg Gln Lys Val Leu Gly Leu Leu Gln
    1730            1735                1740

Ala Ser Ala Lys Gln Ala Glu Glu Leu Lys Pro Ala Val His Ala
    1745            1750                1755

Ala Trp Pro Arg Met Glu Glu Phe Trp Arg Lys His Met Trp Asn
    1760            1765                1770

Phe Val Ser Gly Ile Gln Tyr Leu Ala Gly Leu Ser Thr Leu Pro
    1775            1780                1785

Gly Asn Pro Ala Val Ala Ser Met Met Ser Phe Thr Ala Ser Leu
    1790            1795                1800

Thr Ser Pro Leu Arg Thr Ser Gln Thr Leu Leu Leu Asn Ile Leu
    1805            1810                1815

Gly Gly Trp Ile Ala Thr Gln Val Ala Pro Pro Ala Ser Thr
    1820            1825                1830

Ala Phe Val Val Ser Gly Leu Ala Gly Ala Thr Val Gly Ser Ile
    1835            1840                1845

Gly Leu Gly Arg Val Leu Val Asp Val Leu Ala Gly Tyr Gly Ala
    1850            1855                1860

Gly Val Ser Gly Ala Leu Val Ala Phe Lys Ile Met Ser Gly Glu
    1865            1870                1875

Cys Pro Thr Thr Glu Asp Met Val Asn Leu Leu Pro Ala Leu Leu
    1880            1885                1890

Ser Pro Gly Ala Leu Val Val Gly Val Val Cys Ala Ala Ile Leu
    1895            1900                1905

Arg Arg His Val Gly Pro Ala Glu Gly Ala Asn Gln Trp Met Asn
    1910            1915                1920

Arg Leu Ile Ala Phe Ala Ser Arg Gly Asn His Val Ser Pro Thr
    1925            1930                1935

His Tyr Val Pro Glu Thr Asp Ala Ser Lys Asn Val Thr Gln Ile
    1940            1945                1950

Leu Thr Ser Leu Thr Ile Thr Ser Leu Leu Arg Arg Leu His Gln
    1955            1960                1965

Trp Val Asn Glu Asp Thr Ala Thr Pro Cys Ala Thr Ser Trp Leu
    1970            1975                1980

Arg Asp Val Trp Asp Trp Val Cys Thr Val Leu Ser Asp Phe Arg
    1985            1990                1995

Val Trp Leu Lys Ala Lys Leu Leu Pro Arg Leu Pro Gly Ile Pro
    2000            2005                2010

Phe Leu Ser Cys Gln Thr Gly Tyr Arg Gly Val Trp Ala Gly Asp
    2015            2020                2025

Gly Val Cys His Thr Thr Cys Thr Cys Gly Ala Val Ile Ala Gly
    2030            2035                2040

His Val Lys Asn Gly Thr Met Lys Ile Thr Gly Pro Lys Thr Cys
    2045            2050                2055

Ser Asn Thr Trp His Gly Thr Phe Pro Ile Asn Ala Thr Thr Thr
    2060            2065                2070

Gly Pro Ser Thr Pro Arg Pro Ala Pro Asn Tyr Gln Arg Ala Leu
    2075            2080                2085

Trp Arg Val Ser Ala Glu Asp Tyr Val Glu Val Arg Arg Leu Gly
    2090            2095                2100

Asp Cys His Tyr Val Val Gly Val Thr Ala Glu Gly Leu Lys Cys
    2105            2110                2115
```

```
Pro Cys Gln Val Pro Ala Pro Glu Phe Phe Thr Glu Val Asp Gly
    2120            2125            2130

Val Arg Ile His Arg Tyr Ala Pro Pro Cys Lys Pro Leu Leu Arg
    2135            2140            2145

Asp Glu Val Thr Phe Ser Val Gly Leu Ser Ser Tyr Ala Ile Gly
    2150            2155            2160

Ser Gln Leu Pro Cys Glu Pro Glu Pro Asp Val Thr Val Val Thr
    2165            2170            2175

Ser Met Leu Thr Asp Pro Thr His Ile Thr Ala Glu Thr Ala Ala
    2180            2185            2190

Arg Arg Leu Lys Arg Gly Ser Pro Pro Ser Leu Ala Ser Ser Ser
    2195            2200            2205

Ala Ser Gln Leu Ser Ala Pro Ser Leu Lys Ala Thr Cys Thr Thr
    2210            2215            2220

Pro Lys Asp His Pro Asp Met Glu Leu Ile Glu Ala Asn Leu Leu
    2225            2230            2235

Trp Arg Gln Glu Met Gly Gly Asn Ile Thr Arg Val Glu Ser Glu
    2240            2245            2250

Asn Lys Val Val Ile Leu Asp Ser Phe Glu Pro Leu Thr Ala Glu
    2255            2260            2265

Tyr Asp Glu Arg Glu Ile Ser Val Ser Ala Glu Cys His Arg Pro
    2270            2275            2280

Pro Arg Arg Lys Phe Pro Pro Ala Leu Pro Ile Trp Ala Arg Pro
    2285            2290            2295

Asp Tyr Asn Pro Pro Leu Ile Gln Ala Trp Gln Met Pro Gly Tyr
    2300            2305            2310

Glu Pro Pro Val Val Ser Gly Cys Ala Val Ala Pro Pro Lys Pro
    2315            2320            2325

Ala Pro Ile Pro Pro Arg Arg Lys Arg Leu Val His Leu Asp
    2330            2335            2340

Glu Ser Thr Val Ser His Ala Leu Ala Gln Leu Ala Asp Lys Val
    2345            2350            2355

Phe Val Glu Ser Ser Ser Asp Pro Gly Pro Ser Ser Asp Ser Gly
    2360            2365            2370

Leu Ser Ile Ala Ser Pro Val Pro Pro Ala Pro Thr Thr Pro Asp
    2375            2380            2385

Asp Ala Cys Ser Glu Ala Gly Ser Tyr Ser Ser Met Pro Pro Leu
    2390            2395            2400

Glu Gly Glu Pro Gly Asp Pro Asp Leu Ser Ser Gly Ser Trp Ser
    2405            2410            2415

Thr Val Ser Asp Gln Asp Asp Val Val Cys Cys Ser Met Ser Tyr
    2420            2425            2430

Ser Trp Thr Gly Ala Leu Ile Thr Pro Cys Ser Pro Glu Glu Glu
    2435            2440            2445

Lys Leu Pro Ile Asn Pro Leu Ser Asn Ser Leu Leu Arg Tyr His
    2450            2455            2460

Asn Lys Val Tyr Cys Thr Thr Ser Lys Ser Ala Ser Gln Arg Ala
    2465            2470            2475

Lys Lys Val Thr Phe Asp Arg Thr Gln Val Leu Asp Ala His Tyr
    2480            2485            2490

Asp Ser Val Leu Lys Asp Ile Lys Leu Ala Ala Ser Lys Val Ser
    2495            2500            2505

Ala Arg Leu Leu Thr Leu Glu Glu Ala Cys Gln Leu Thr Pro Pro
```

```
                    2510                2515                2520
His Ser Ala Arg Ser Lys Tyr Gly Phe Gly Ala Lys Glu Val Arg
    2525                2530                2535

Ser Leu Ser Gly Arg Ala Val Asn His Ile Lys Ser Val Trp Lys
    2540                2545                2550

Asp Leu Leu Glu Asp Pro Gln Thr Pro Ile Pro Thr Thr Ile Met
    2555                2560                2565

Ala Lys Asn Glu Val Phe Cys Val Asp Pro Ala Lys Gly Gly Lys
    2570                2575                2580

Lys Pro Ala Arg Leu Ile Val Tyr Pro Asp Leu Gly Val Arg Val
    2585                2590                2595

Cys Glu Lys Met Ala Leu Tyr Asp Ile Thr Gln Lys Leu Pro Gln
    2600                2605                2610

Ala Val Met Gly Ala Ser Tyr Gly Phe Gln Tyr Ser Pro Ala Gln
    2615                2620                2625

Arg Val Glu Tyr Leu Leu Lys Ala Trp Ala Glu Lys Lys Asp Pro
    2630                2635                2640

Met Gly Phe Ser Tyr Asp Thr Arg Cys Phe Asp Ser Thr Val Thr
    2645                2650                2655

Glu Arg Asp Ile Arg Thr Glu Glu Ser Ile Tyr Gln Ala Cys Ser
    2660                2665                2670

Leu Pro Glu Glu Ala Arg Thr Ala Ile His Ser Leu Thr Glu Arg
    2675                2680                2685

Leu Tyr Val Gly Gly Pro Met Phe Asn Ser Lys Gly Gln Thr Cys
    2690                2695                2700

Gly Tyr Arg Arg Cys Arg Ala Ser Gly Val Leu Thr Thr Ser Met
    2705                2710                2715

Gly Asn Thr Ile Thr Cys Tyr Val Lys Ala Leu Ala Ala Cys Lys
    2720                2725                2730

Ala Ala Gly Ile Val Ala Pro Thr Met Leu Val Cys Gly Asp Asp
    2735                2740                2745

Leu Val Val Ile Ser Glu Ser Gln Gly Thr Glu Glu Asp Glu Arg
    2750                2755                2760

Asn Leu Arg Ala Phe Thr Glu Ala Met Thr Arg Tyr Ser Ala Pro
    2765                2770                2775

Pro Gly Asp Pro Pro Arg Pro Glu Tyr Asp Leu Glu Leu Ile Thr
    2780                2785                2790

Ser Cys Ser Ser Asn Val Ser Val Ala Leu Gly Pro Arg Gly Arg
    2795                2800                2805

Arg Arg Tyr Tyr Leu Thr Arg Asp Pro Thr Thr Pro Leu Ala Arg
    2810                2815                2820

Ala Ala Trp Glu Thr Val Arg His Ser Pro Ile Asn Ser Trp Leu
    2825                2830                2835

Gly Asn Ile Ile Gln Tyr Ala Pro Thr Ile Trp Val Arg Met Val
    2840                2845                2850

Leu Met Thr His Phe Phe Ser Ile Leu Met Val Gln Asp Thr Leu
    2855                2860                2865

Asp Gln Asn Leu Asn Phe Glu Met Tyr Gly Ser Val Tyr Ser Val
    2870                2875                2880

Asn Pro Leu Asp Leu Pro Ala Ile Ile Glu Arg Leu His Gly Leu
    2885                2890                2895

Asp Ala Phe Ser Met His Thr Tyr Ser His His Glu Leu Thr Arg
    2900                2905                2910
```

```
Val Ala Ser Ala Leu Arg Lys Leu Gly Ala Pro Pro Leu Arg Val
    2915                2920                2925

Trp Lys Ser Arg Ala Arg Ala Val Arg Ala Ser Leu Ile Ser Arg
    2930                2935                2940

Gly Gly Lys Ala Ala Val Cys Gly Arg Tyr Leu Phe Asn Trp Ala
    2945                2950                2955

Val Lys Thr Lys Leu Lys Leu Thr Pro Leu Pro Glu Ala Arg Leu
    2960                2965                2970

Leu Asp Leu Ser Ser Trp Phe Thr Val Gly Ala Gly Gly Gly Gly
    2975                2980                2985

Ile Phe His Ser Val Ser Arg Ala Arg Pro Arg Ser Leu Leu Phe
    2990                2995                3000

Gly Leu Leu Leu Leu Phe Val Gly Val Gly Leu Phe Leu Leu Pro
    3005                3010                3015

Ala Arg
    3020

<210> SEQ ID NO 13
<211> LENGTH: 9603
<212> TYPE: DNA
<213> ORGANISM: Hepatitis C virus

<400> SEQUENCE: 13
acctgctctc tatgagagca acactccacc atgaaccgct cccctgtgag gaactactgt      60
cttcacgcag aaagcgtcta gccatggcgt tagtatgagt gttgtacagc ctccaggacc     120 cccctcccg ggagagccat agtggtctgc ggaaccggtg agtacaccgg aatcgccggg      180
atgaccgggt cctttcttgg attaacccgc tcaatgcccg gaaatttggg cgtgcccccg     240
caagactgct agccgagtag tgttgggtcg cgaaaggcct tgtggtactg cctgataggg     300
tgcttgcgag tgccccggga ggtctcgtag accgtgcacc atgagcacga atcctaaacc     360
tcaaagaaaa accaaacgta acaccaaccg ccgcccaatg acgttaagt tcccgggtgg      420 tggccagatc gttggcggag tttacttgtt gccgcgcagg ggccccagat gggtgtgcg     480 cgcgactcgg aagacttcgg agcggtcgca acctcgtgga agacgccaac ctatccccaa     540
ggcgcgtcga cccgagggaa ggtcctgggc acaaccagga tatccatggc ctctttacgg     600
taatgagggt tgtgggtggg caggatggct cttgtccccc cgtggctctc gaccgtcttg     660 ggcccaaat gatccccggc ggaggtcccg caatttgggt aaggtcatcg atacctaac       720 ctgcggcttc gccgacctca tgggatacat cccgctcgta ggcgccccg tgggtggcgt      780 cgccagggcc ctggcacatg tgtcagggc tttggaggac gggatcaatt atgcaacagg     840
gaatctcccc ggttgctcct tttctatctt cctcttggca cttctttcgt gcctgactgt     900
ccccgcttcg gccgttaact atcgcaatgt ctcgggcatc taccatgtca ccaatgactg     960
cccgaattca agcatagtgt atgaggccga ccatcacatc ttgcaccttc aggttgcgt    1020 gccctgcgtg agagagggga atcagtcacg ctgctgggtg gcccttactc ctaccgtcgc   1080
agcgccatac atcggcgcac cgcttgagtc cttacggagt catgtggatt tgatggtggg   1140
ggccgccact gtttgctcgg gtctttacat cggggacctg tgtggcggct tgttcctagt   1200
tggccagatg ttttcattcc gaccacggcg ccactggacc acccaggatt gcaattgttc   1260
catctacaca gggcacatta caggccacag aatggcctgg gacatgatga tgaactggag   1320
tccaacaacc accttagttc tcgcccaggt catgaggatc ccaaccactc tggcagactt   1380
```

```
actctctgga ggccactggg gtgtcctcgt gggagtggcc tatttcagca tgcaggccaa   1440
ttgggccaaa gtcatcttgg tcctattcct ctttgcaggg gttgatgccg agactcacgt   1500
gtctggggca gcagtcggcc ggagtaccgc cggcttggct aacctctttt cttctgggtc   1560
taagcagaat ttacagctca tcaacagcaa tgggagctgg catataaata ggactgccct   1620
taactgcaat gacagcttaa acactgggtt cttggctagc ttgttctaca cccacaagtt   1680
taacagctca gggtgttccg aacggctcgc gtgctgcaag agccttgaca gctacggcca   1740
aggctggggc ccactcgggg tcgctaacat cagcggctcg tctgatgaca ggccttattg   1800
ctggcactac gcgcctcggc cgtgcggat tgtgccagca tccagtgtgt gtggcccccgt   1860
gtattgtttc actcccagcc ctgtcgtggt cggtactact gatcacgtcg gggtccctac   1920
ttacacctgg ggggagaatg agagtgatgt cttccttttg aactcgacca gaccgccgca   1980
tggtgcgtgg tttggatgcg tgtggatgaa cagtaccggg ttcaccaaaa cctgtggcgc   2040
ccctccatgc gaggttaaca ccaataatgg gacctggcac tgccccaccg attgcttcag   2100
gaagcatccg gagactacct acgccaagtg cggatcaggg ccttggatca caccgcgctg   2160
cctgattgat tacccgtacc ggctgtggca tttcccgtgc accgccaact tctccgtctt   2220
taacatcagg acatttgtcg gcggtataga gcatcggatg caagcggcat gcaactggac   2280
caggggggaa gtctgtggct tggagcacag ggatcgcgta gagctatcac ccctgctcct   2340
taccactaca gcgtggcaga tcctcccctg ctctttcacc actttacctg ccctctccac   2400
cggcttgatc cacctccacc aaaatatcgt ggacgtccag tacctctatg tgttgggtc    2460
tgcagtggta tcttgggccc ttaagtggga atatgtggtg ctcgcgttcc tgcttctcgc   2520
ggacgcgaga gtctctgcct gcctatggat gatgtttatg gtaagtcaag ttgaggcggc   2580
tctgtccaac ctgattaaca tcaatgctgc ttcagccgct ggtgcccaag gcttctggta   2640
cgccatcctc ttcatctgca ttgtctggca tgtcaagggc tggttcccag ctgctgctgc   2700
ctacgcagcc tgcgggctgt ggcccctgtt tctcctgctt ctgatgctgc tgagagggc    2760
ttatgcatac gaccaggaag tggcagggtc ccttggcggc gccatcgttg tcatgctgac   2820
cattctgaca ctgtctccgc actacaagtt atggctggct aggggattgt ggtggatcca   2880
acatttata gctaggaccg aggctgtgct gcatgtctat attccatcct tcaacgtgcg    2940
cgggcctcgc gactcagtga ttgttcttgc agtcctggtc tgtccacacc tagtatttga   3000
catcacaaaa tatcttctgg ccatcttagg gcccctccgc atactccagg cctcgctcct   3060
acgcatccct tactttgtga gggcacaagc gctggttaag atctgcagct tgttgcgtgg   3120
ggtagtttat ggcaagtact tccaaatggt cgtgcttaaa gcaggggccc tgactggtac   3180
ttacatctat gaccacctta ctcccatgtc agattgggcc gctacgggcc tccgcgattt   3240
ggcggtggcc ctagagccag ttgtgttcac gcccatggag aagaaagtca tcgtctgggg   3300
cgctgacacc gctgcgtgcg gagacatcat aagggggatta cctgtttcgg ccaggttggg   3360
caatgaaatc ttgctcggac cagccgatac agaaacatca aagggggtgga gactccttgc   3420
ccccatcaca gcatacgcgc agcagacccg cggcttgttc agcaccatcg taacgagcct   3480
cactggcagg gacaccaatg agaattgtgg cgaagtgcag gtcttatcca ccgctacgca   3540
gtccttcctg ggtactgcgg ttaacggcgt gatgtggacc gtctaccacg ggcgggtgc    3600
caagaccatc agcggcccga agggacctgt caatcaaatg tacactaatg ttgaccaaga   3660
cttggtgggg tggccagcac ccccggagt  cagatctctt gctccgtgca cctgcggctc   3720
ggcagacttg tatctagtca ccaggcacgc agatgtaata cccgtgcgca ggagaggaga   3780
```

```
caccagagga gctctcttga gccctagacc aatatccact cttaagggat cttccggagg   3840
tccgctgctg tgccccatgg gacacgccgc cggcatattc cgtgcggcgg tgtgtactcg   3900
aggggtagcc aaggcggtag acttcgtccc ggttgaatct cttgagacta ccatgagatc   3960
accagtgttc actgacaact caacacctcc agcagtgccc cagacctacc aggtcgcgca   4020
cctacacgca ccaacaggaa gtggcaagag caccaaagtc ccggcggcgt atgctgccca   4080
aggctataaa gtgctagtgc tcaatccttc ggttgcggcc acactgggtt ttggggtata   4140
catgtccaag gcatatggca tcgacccgaa catccggtcg ggagtcagga ccatcaccac   4200
gggtgcgcca atcacgtact caacgtatgg taagttcctg gctgatggag gttgcagcgg   4260
agggccatac gacataatca tctgtgacga gtgccattcc actgactcca caacgatcct   4320
tggcataggc acagtcctgg accaagcgga gaccgctgga gtgcgcctca ccgtgctcgc   4380
gactgctact ccgccagggt cagtgactac acctcattcc aacatagagg aggtcgccct   4440
gccaacaacg ggggaaatcc ccttttacgg caaggcgatc cctctggagc tgattaaggg   4500
gggcagacat ctcatcttct gccactcaaa gaaaaagtgt gatgaactgg ccagacaact   4560
gacatctctt ggtctgaatg ccgtagccta ctacagaggc ttagacgttt cggtgattcc   4620
cacgtctggg gacgtcgtgg tatgcgccac ggacgccctc atgacgggtt ttaccggcga   4680
ctttgactca gtgatagact gcaatacatc tgtgatacag actgttgacc tcagcttgga   4740
ccccaccttc tccatagaga ctacaaccgt tccccaggac gcggtatccc gcagccagcg   4800
gagaggccgc actggtaggg ggaggttggg cacataccgg tatgtcaccc cgggagagag   4860
accatcaggc atgtttgaca ctgcagtgct ttgcgagtgc tacgatgccg ggtgtgcctg   4920
gtacgagctg acacctgctg aaaccacaac aaggctgaaa gcttacttcg acacaccagg   4980
ccttcctgtg tgccaagacc atctggagtt ctgggagagc gtctttacag ggttaaccca   5040
catagacggt catttcctat cccagaccaa gcaatcgggt gagaatttcc cgtatcttgt   5100
tgcttaccaa gccacggtgt gcgccaaggc tctggcgcct ccaccaagct gggacaccat   5160
gtggaagtgc ctaattcgcc ttaagcccac cctgcacggg cccacacccc tcctctacag   5220
actggggtct gtgcagaatg aagtggtgct cacccatccc atcaccaaat acatcatggc   5280
ttgcatgtca gctgatctcg aggtagtgac aagtacgtgg gtcttggtgg gcggcgtcct   5340
ggcagctctg gcttcttact gtctttcagt gggcagcgta gtgattgttg ggagagtcgt   5400
cctgtcgggc caacctgctg tcattcccga tcgcgaagtg ctctaccaac agttcgacga   5460
aatggaggag tgttccaaac acctcccact agtcgagcac gggttacaac tggctgagca   5520
gttcaagcag aaggccttag gtctcctaaa tttcgctggc aagcaagccc aagaggcaac   5580
accagtgatc cagtctaact tcgctaaact tgagcagttt ggggcgaagc acatgtggaa   5640
tttcatcagc ggcattcaat atctcgctgg actgtctacc ttgccaggca atcctgtcat   5700
tgcttccctc atgtccttta ctgctgctgt tacaagccct ctgaccaccc aacaaacccct   5760 ccttttttaac atcttggggg gatgggtggc ctcgcagatt gcgactccga cggcttctac   5820
cgcattcgtc gtgagcggct tggcggggc ggcagttggc agtgtgggcc ttggcaaaat   5880
tttggtggac attctcgccg gttacggcgc cggcgtagct ggcgctgtgg ttaccttcaa   5940
gatcatgagc ggcgagatgc cttccacaga ggacttggta aatttgctcc cggccattct   6000
atcgcccgga gcattggtag tggggtggt atgcgcggcg attttgcgcc gccacgtggg   6060
cccgggcgaa ggggctgtgc agtggatgaa ccgtctaatt gcgttcgcat cgcgaggcaa   6120
```

```
tcacgtgtct cccacgcatt acgtccctga gtccgacgcg gcagcccgcg tgaccaccat    6180
actatcatcc ctcactgtga catcccttct cagacgcctc cacaagtgga tcaatgaaga    6240
ttgctccacc ccatgtgccg aatcttggct atgggaggta tgggattggg tctgcaccgt    6300
gctgagtgac ttcaagacgt ggctaaaagc caagttgctg cccctcatgc caggcatccc    6360
cttcctctca tgccagaggg gctataaggg agagtggcgc ggagatggcg tgatgcatac    6420
cacatgcccc tgcggagcag atctggcagg tcacatcaag aacggctcga tgagaatcac    6480
cgggccgaaa acctgcagca acacatggca tggtaccttc cccatcaatg cttacaccac    6540
aggccctggt gtacccatcc cggcgccgaa ctacaagttc gcgctttgga gggtgtccgc    6600
cgaggactac gtggaggttc gcagagtggg tgatttccat tatgtcaccg gggtaacaca    6660
agacaacatc aagtgcccct gccaagttcc ggccccagag ttcttcacgg aagtggacgg    6720
catcaggcta caccgccacg ccccgaagtg caaaccctt  ctgcgggacg aagtgtcgtt    6780
ctcagtagga ctcaattcgt tcgtagtggg atcacaactc ccatgcgagc cagagccgga    6840
cgtggcagtg ctaacatcca tgctgacaga cccatcacac ataacggcgg aatcggcgcg    6900
tcggagattg gctcgagggt cacgaccctc gctagctagt tcctcggcga gtcagctttc    6960
cgccccgtct ctcaaggcca cgtgtaccgc tccccatgac tcccctggta ctgatctcct    7020
cgaggctaac ctcttgtggg ggtctaccgc taccagggtt gagacggacg agaaggtaat    7080
aatactagac tcttttgagt catgtgtggc tgagccaaat gatgacaggg aagtctcggt    7140
tgccgcggaa atcctgcgtc cgaccaagaa gttccctcca gcactaccga tctgggcccg    7200
gccggattac aatccacctc ttaccgagac gtggaagcag caggactaca agcctccgac    7260
cgtccacggg tgcgctctgc ctcccggcaa gcagcccccc gttcctcctc ccaggaggaa    7320
acggacggta cagctcactg agtccgttgt ttctaccgct ttggcagagc tggacgcaaa    7380
gacctttggc cagtcagagc cgagcgcaga ccgtgataca gaccttacca ccccaactga    7440
gaccacagac tcgggcccca tcgtcgtgga tgatgcattc gatgacggat cttattcgtc    7500
aatgcctcca ctagagggg  agcccggtga cccggacttg acatcagact cttggtccac    7560
tgttagcgga tcgaggacg  tcgtgtgctg ctccatgtca tactcctgga ccggggctct    7620
aataactccc tgtagccccg aagaggaaaa gttgccaatc aacccttga  gtaactcgct    7680
gttgcgatac cataacaagg tgtactgtac aacatcaaag agcgcctcac agagggctaa    7740
aaaggtaact tttgacagga cgcaagtgct cgacgcccat tatgactcag tcttaaagga    7800
catcaagcta gcggcttcca aggtcagcgc aaggctcctc accttggagg aggcgtgcca    7860
gttgactcca ccccattctg caagatccaa gtatggattc ggggccaagg aggtccgcag    7920
cttgtccggg agggccgtta accacatcaa gtccgtgtgg aaggacctcc tggaagaccc    7980
acaaacacca attcccacaa ccatcatggc caaaaatgag gtgttctgcg tggaccccgc    8040
caagggggt aagaaaccag ctcgcctcat cgtttaccct gacctcggcg tccgggtctg    8100
cgagaaaatg gccctctatg acattacaca aaagcttcct caggcggtaa tgggagcttc    8160
ctatggcttc cagtactccc ctgcccaacg ggtggagtat ctcttgaaag catgggcgga    8220
aaagaaggac cccatgggtt tttcgtatga taccgatgc  ttcgactcaa ccgtcactga    8280
gagagacatc aggaccgagg agtccatata ccaggcctgc tccctgcccg aggaggcccg    8340
cactgccata cactcgctga ctgagagact ttacgtagga gggcccatgt tcaacagcaa    8400
gggtcaaacc tgcggttaca gacgttgccg cgccagcggg gtgctaacca ctagcatggg    8460
taacaccatc acatgctatg tgaaagccct agcggcctgc aaggctgcgg ggatagttgc    8520
```

-continued

```
gcccacaatg ctggtatgcg gcgatgacct agtagtcatc tcagaaagcc aggggactga  8580
ggaggacgag cggaacctga gagccttcac ggaggccatg accaggtact ctgcccctcc  8640
tggtgatccc cccagaccgg aatatgacct ggagctaata acatcctgtt cctcaaatgt  8700
gtctgtggcg ttgggcccgc ggggccgccg cagatactac ctgaccagag acccaaccac  8760
tccactcgcc cgggctgcct gggaaacagt tagacactcc cctatcaatt catggctggg  8820
aaacatcatc cagtatgctc caaccatatg ggttcgcatg gtcctaatga cacacttctt  8880
ctccattctc atggtccaag acaccctgga ccagaacctc aactttgaga tgtatggatc  8940
agtatactcc gtgaatcctt tggaccttcc agccataatt gagaggttac acgggcttga  9000
cgccttttct atgcacacat actctcacca cgaactgacg cgggtggctt cagccctcag  9060
aaaacttggg gcgccacccc tcagggtgtg aagagtcgg gctcgcgcag tcagggcgtc  9120
cctcatctcc cgtggaggga agcggccgt ttgcggccga tatctcttca attgggcggt  9180
gaagaccaag ctcaaactca ctccattgcc ggaggcgcgc ctactggact tatccagttg  9240
gttcaccgtc ggcgccggcg ggggcgacat ttttcacagc gtgtcgcgcg cccgaccccg  9300
ctcattactc ttcggcctac tcctactttt cgtaggggta ggcctcttcc tactccccgc  9360
tcggtagagc ggcacacact aggtacactc catagctaac tgttcctttt tttttttttt  9420
tttttttttt tttttttttt tttttttttc tttttttttt ttttccctct ttcttccctt  9480
ctcatcttat tctactttct ttcttggtgg ctccatctta gccctagtca cggctagctg  9540
tgaaaggtcc gtgagccgca tgactgcaga gagtgccgta actggtctct ctgcagatca  9600
tgt                                                                9603
```

<210> SEQ ID NO 14
<211> LENGTH: 3008
<212> TYPE: PRT
<213> ORGANISM: Hepatitis C virus

<400> SEQUENCE: 14

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Leu Glu Asp
145                 150                 155                 160

Gly Ile Asn Tyr Ala Thr Gly Asn Leu Pro Gly Cys Ser Phe Ser Ile
                165                 170                 175
```

-continued

```
Phe Leu Leu Ala Leu Leu Ser Cys Leu Thr Val Pro Ala Ser Ala Val
            180                 185                 190

Asn Tyr Arg Asn Val Ser Gly Ile Tyr His Val Thr Asn Asp Cys Pro
        195                 200                 205

Asn Ser Ser Ile Val Tyr Glu Ala Asp His His Ile Leu His Leu Pro
    210                 215                 220

Gly Cys Val Pro Cys Val Arg Glu Gly Asn Gln Ser Arg Cys Trp Val
225                 230                 235                 240

Ala Leu Thr Pro Thr Val Ala Pro Tyr Ile Gly Ala Pro Leu Glu
                245                 250                 255

Ser Leu Arg Ser His Val Asp Leu Met Val Gly Ala Ala Thr Val Cys
            260                 265                 270

Ser Gly Leu Tyr Ile Gly Asp Leu Cys Gly Gly Leu Phe Leu Val Gly
        275                 280                 285

Gln Met Phe Ser Phe Arg Pro Arg His Trp Thr Thr Gln Asp Cys
    290                 295                 300

Asn Cys Ser Ile Tyr Thr Gly His Ile Thr Gly His Arg Met Ala Trp
305                 310                 315                 320

Asp Met Met Met Asn Trp Ser Pro Thr Thr Leu Val Leu Ala Gln
                325                 330                 335

Val Met Arg Ile Pro Thr Thr Leu Ala Asp Leu Leu Ser Gly Gly His
            340                 345                 350

Trp Gly Val Leu Val Gly Val Ala Tyr Phe Ser Met Gln Ala Asn Trp
        355                 360                 365

Ala Lys Val Ile Leu Val Leu Phe Leu Phe Ala Gly Val Asp Ala Glu
    370                 375                 380

Thr His Val Ser Gly Ala Ala Val Gly Arg Ser Thr Ala Gly Leu Ala
385                 390                 395                 400

Asn Leu Phe Ser Ser Gly Ser Lys Gln Asn Leu Gln Leu Ile Asn Ser
                405                 410                 415

Asn Gly Ser Trp His Ile Asn Arg Thr Ala Leu Asn Cys Asn Asp Ser
            420                 425                 430

Leu Asn Thr Gly Phe Leu Ala Ser Leu Phe Tyr Thr His Lys Phe Asn
        435                 440                 445

Ser Ser Gly Cys Ser Glu Arg Leu Ala Cys Cys Lys Ser Leu Asp Ser
    450                 455                 460

Tyr Gly Gln Gly Trp Gly Pro Leu Gly Val Ala Asn Ile Ser Gly Ser
465                 470                 475                 480

Ser Asp Asp Arg Pro Tyr Cys Trp His Tyr Ala Pro Arg Pro Cys Gly
                485                 490                 495

Ile Val Pro Ala Ser Ser Val Cys Gly Pro Val Tyr Cys Phe Thr Pro
            500                 505                 510

Ser Pro Val Val Gly Thr Thr Asp His Val Gly Val Pro Thr Tyr
        515                 520                 525

Thr Trp Gly Glu Asn Glu Ser Asp Val Phe Leu Leu Asn Ser Thr Arg
    530                 535                 540

Pro Pro His Gly Ala Trp Phe Gly Cys Val Trp Met Asn Ser Thr Gly
545                 550                 555                 560

Phe Thr Lys Thr Cys Gly Ala Pro Pro Cys Glu Val Asn Thr Asn Asn
                565                 570                 575

Gly Thr Trp His Cys Pro Thr Asp Cys Phe Arg Lys His Pro Glu Thr
            580                 585                 590
```

-continued

Thr Tyr Ala Lys Cys Gly Ser Gly Pro Trp Ile Thr Pro Arg Cys Leu
        595             600             605

Ile Asp Tyr Pro Tyr Arg Leu Trp His Phe Pro Cys Thr Ala Asn Phe
610             615             620

Ser Val Phe Asn Ile Arg Thr Phe Val Gly Ile Glu His Arg Met
625             630             635             640

Gln Ala Ala Cys Asn Trp Thr Arg Gly Glu Val Cys Gly Leu Glu His
                645             650             655

Arg Asp Arg Val Glu Leu Ser Pro Leu Leu Thr Thr Thr Ala Trp
            660             665             670

Gln Ile Leu Pro Cys Ser Phe Thr Thr Leu Pro Ala Leu Ser Thr Gly
        675             680             685

Leu Ile His Leu His Gln Asn Ile Val Asp Val Gln Tyr Leu Tyr Gly
        690             695             700

Val Gly Ser Ala Val Val Ser Trp Ala Leu Lys Trp Glu Tyr Val Val
705             710             715             720

Leu Ala Phe Leu Leu Leu Ala Asp Ala Arg Val Ser Ala Cys Leu Trp
                725             730             735

Met Met Phe Met Val Ser Gln Val Glu Ala Ala Leu Ser Asn Leu Ile
            740             745             750

Asn Ile Asn Ala Ala Ser Ala Ala Gly Ala Gln Gly Phe Trp Tyr Ala
        755             760             765

Ile Leu Phe Ile Cys Ile Val Trp His Val Lys Gly Trp Phe Pro Ala
        770             775             780

Ala Ala Ala Tyr Ala Ala Cys Gly Leu Trp Pro Leu Phe Leu Leu Leu
785             790             795             800

Leu Met Leu Pro Glu Arg Ala Tyr Ala Tyr Asp Gln Glu Val Ala Gly
            805             810             815

Ser Leu Gly Gly Ala Ile Val Val Met Leu Thr Ile Leu Thr Leu Ser
            820             825             830

Pro His Tyr Lys Leu Trp Leu Ala Arg Gly Leu Trp Trp Ile Gln His
        835             840             845

Phe Ile Ala Arg Thr Glu Ala Val Leu His Val Tyr Ile Pro Ser Phe
850             855             860

Asn Val Arg Gly Pro Arg Asp Ser Val Ile Val Leu Ala Val Leu Val
865             870             875             880

Cys Pro His Leu Val Phe Asp Ile Thr Lys Tyr Leu Leu Ala Ile Leu
                885             890             895

Gly Pro Leu Arg Ile Leu Gln Ala Ser Leu Leu Arg Ile Pro Tyr Phe
            900             905             910

Val Arg Ala Gln Ala Leu Val Lys Ile Cys Ser Leu Leu Arg Gly Val
            915             920             925

Val Tyr Gly Lys Tyr Phe Gln Met Val Val Leu Lys Ala Gly Ala Leu
        930             935             940

Thr Gly Thr Tyr Ile Tyr Asp His Leu Thr Pro Met Ser Asp Trp Ala
945             950             955             960

Ala Thr Gly Leu Arg Asp Leu Ala Val Ala Leu Glu Pro Val Val Phe
            965             970             975

Thr Pro Met Glu Lys Lys Val Ile Val Trp Gly Ala Asp Thr Ala Ala
            980             985             990

Cys Gly Asp Ile Ile Arg Gly Leu Pro Val Ser Ala Arg Leu Gly Asn
        995             1000            1005

Glu Ile Leu Leu Gly Pro Ala Asp Thr Glu Thr Ser Lys Gly Trp

```
                1010                1015                1020

Arg  Leu  Leu  Ala  Pro  Ile  Thr  Ala  Tyr  Ala  Gln  Gln  Thr  Arg  Gly
          1025                1030                1035

Leu  Phe  Ser  Thr  Ile  Val  Thr  Ser  Leu  Thr  Gly  Arg  Asp  Thr  Asn
          1040                1045                1050

Glu  Asn  Cys  Gly  Glu  Val  Gln  Val  Leu  Ser  Thr  Ala  Thr  Gln  Ser
          1055                1060                1065

Phe  Leu  Gly  Thr  Ala  Val  Asn  Gly  Val  Met  Trp  Thr  Val  Tyr  His
          1070                1075                1080

Gly  Ala  Gly  Ala  Lys  Thr  Ile  Ser  Gly  Pro  Lys  Gly  Pro  Val  Asn
          1085                1090                1095

Gln  Met  Tyr  Thr  Asn  Val  Asp  Gln  Asp  Leu  Val  Gly  Trp  Pro  Ala
          1100                1105                1110

Pro  Pro  Gly  Val  Arg  Ser  Leu  Ala  Pro  Cys  Thr  Cys  Gly  Ser  Ala
          1115                1120                1125

Asp  Leu  Tyr  Leu  Val  Thr  Arg  His  Ala  Asp  Val  Ile  Pro  Val  Arg
          1130                1135                1140

Arg  Arg  Gly  Asp  Thr  Arg  Gly  Ala  Leu  Leu  Ser  Pro  Arg  Pro  Ile
          1145                1150                1155

Ser  Thr  Leu  Lys  Gly  Ser  Ser  Gly  Gly  Pro  Leu  Leu  Cys  Pro  Met
          1160                1165                1170

Gly  His  Ala  Ala  Gly  Ile  Phe  Arg  Ala  Ala  Val  Cys  Thr  Arg  Gly
          1175                1180                1185

Val  Ala  Lys  Ala  Val  Asp  Phe  Val  Pro  Val  Glu  Ser  Leu  Glu  Thr
          1190                1195                1200

Thr  Met  Arg  Ser  Pro  Val  Phe  Thr  Asp  Asn  Ser  Thr  Pro  Pro  Ala
          1205                1210                1215

Val  Pro  Gln  Thr  Tyr  Gln  Val  Ala  His  Leu  His  Ala  Pro  Thr  Gly
          1220                1225                1230

Ser  Gly  Lys  Ser  Thr  Lys  Val  Pro  Ala  Ala  Tyr  Ala  Ala  Gln  Gly
          1235                1240                1245

Tyr  Lys  Val  Leu  Val  Leu  Asn  Pro  Ser  Val  Ala  Ala  Thr  Leu  Gly
          1250                1255                1260

Phe  Gly  Val  Tyr  Met  Ser  Lys  Ala  Tyr  Gly  Ile  Asp  Pro  Asn  Ile
          1265                1270                1275

Arg  Ser  Gly  Val  Arg  Thr  Ile  Thr  Thr  Gly  Ala  Pro  Ile  Thr  Tyr
          1280                1285                1290

Ser  Thr  Tyr  Gly  Lys  Phe  Leu  Ala  Asp  Gly  Gly  Cys  Ser  Gly  Gly
          1295                1300                1305

Pro  Tyr  Asp  Ile  Ile  Ile  Cys  Asp  Glu  Cys  His  Ser  Thr  Asp  Ser
          1310                1315                1320

Thr  Thr  Ile  Leu  Gly  Ile  Gly  Thr  Val  Leu  Asp  Gln  Ala  Glu  Thr
          1325                1330                1335

Ala  Gly  Val  Arg  Leu  Thr  Val  Leu  Ala  Thr  Ala  Thr  Pro  Pro  Gly
          1340                1345                1350

Ser  Val  Thr  Thr  Pro  His  Ser  Asn  Ile  Glu  Glu  Val  Ala  Leu  Pro
          1355                1360                1365

Thr  Thr  Gly  Glu  Ile  Pro  Phe  Tyr  Gly  Lys  Ala  Ile  Pro  Leu  Glu
          1370                1375                1380

Leu  Ile  Lys  Gly  Gly  Arg  His  Leu  Ile  Phe  Cys  His  Ser  Lys  Lys
          1385                1390                1395

Lys  Cys  Asp  Glu  Leu  Ala  Arg  Gln  Leu  Thr  Ser  Leu  Gly  Leu  Asn
          1400                1405                1410
```

```
Ala Val Ala Tyr Tyr Arg Gly Leu Asp Val Ser Val Ile Pro Thr
    1415            1420                1425

Ser Gly Asp Val Val Cys Ala Thr Asp Ala Leu Met Thr Gly
    1430            1435                1440

Phe Thr Gly Asp Phe Asp Ser Val Ile Asp Cys Asn Thr Ser Val
    1445            1450                1455

Ile Gln Thr Val Asp Leu Ser Leu Asp Pro Thr Phe Ser Ile Glu
    1460            1465                1470

Thr Thr Thr Val Pro Gln Asp Ala Val Ser Arg Ser Gln Arg Arg
    1475            1480                1485

Gly Arg Thr Gly Arg Gly Arg Leu Gly Thr Tyr Arg Tyr Val Thr
    1490            1495                1500

Pro Gly Glu Arg Pro Ser Gly Met Phe Asp Thr Ala Val Leu Cys
    1505            1510                1515

Glu Cys Tyr Asp Ala Gly Cys Ala Trp Tyr Glu Leu Thr Pro Ala
    1520            1525                1530

Glu Thr Thr Thr Arg Leu Lys Ala Tyr Phe Asp Thr Pro Gly Leu
    1535            1540                1545

Pro Val Cys Gln Asp His Leu Glu Phe Trp Glu Ser Val Phe Thr
    1550            1555                1560

Gly Leu Thr His Ile Asp Gly His Phe Leu Ser Gln Thr Lys Gln
    1565            1570                1575

Ser Gly Glu Asn Phe Pro Tyr Leu Val Ala Tyr Gln Ala Thr Val
    1580            1585                1590

Cys Ala Lys Ala Leu Ala Pro Pro Pro Ser Trp Asp Thr Met Trp
    1595            1600                1605

Lys Cys Leu Ile Arg Leu Lys Pro Thr Leu His Gly Pro Thr Pro
    1610            1615                1620

Leu Leu Tyr Arg Leu Gly Ser Val Gln Asn Glu Val Val Leu Thr
    1625            1630                1635

His Pro Ile Thr Lys Tyr Ile Met Ala Cys Met Ser Ala Asp Leu
    1640            1645                1650

Glu Val Val Thr Ser Thr Trp Val Leu Val Gly Gly Val Leu Ala
    1655            1660                1665

Ala Leu Ala Ser Tyr Cys Leu Ser Val Gly Ser Val Val Ile Val
    1670            1675                1680

Gly Arg Val Val Leu Ser Gly Gln Pro Ala Val Ile Pro Asp Arg
    1685            1690                1695

Glu Val Leu Tyr Gln Gln Phe Asp Glu Met Glu Glu Cys Ser Lys
    1700            1705                1710

His Leu Pro Leu Val Glu His Gly Leu Gln Leu Ala Glu Gln Phe
    1715            1720                1725

Lys Gln Lys Ala Leu Gly Leu Leu Asn Phe Ala Gly Lys Gln Ala
    1730            1735                1740

Gln Glu Ala Thr Pro Val Ile Gln Ser Asn Phe Ala Lys Leu Glu
    1745            1750                1755

Gln Phe Trp Ala Lys His Met Trp Asn Phe Ile Ser Gly Ile Gln
    1760            1765                1770

Tyr Leu Ala Gly Leu Ser Thr Leu Pro Gly Asn Pro Val Ile Ala
    1775            1780                1785

Ser Leu Met Ser Phe Thr Ala Ala Val Thr Ser Pro Leu Thr Thr
    1790            1795                1800
```

```
Gln Gln Thr Leu Leu Phe Asn Ile Leu Gly Gly Trp Val Ala Ser
    1805                1810                1815

Gln Ile Ala Thr Pro Thr Ala Ser Thr Ala Phe Val Val Ser Gly
    1820                1825                1830

Leu Ala Gly Ala Ala Val Gly Ser Val Gly Leu Gly Lys Ile Leu
    1835                1840                1845

Val Asp Ile Leu Ala Gly Tyr Gly Ala Gly Val Ala Gly Ala Val
    1850                1855                1860

Val Thr Phe Lys Ile Met Ser Gly Glu Met Pro Ser Thr Glu Asp
    1865                1870                1875

Leu Val Asn Leu Leu Pro Ala Ile Leu Ser Pro Gly Ala Leu Val
    1880                1885                1890

Val Gly Val Val Cys Ala Ala Ile Leu Arg Arg His Val Gly Pro
    1895                1900                1905

Gly Glu Gly Ala Val Gln Trp Met Asn Arg Leu Ile Ala Phe Ala
    1910                1915                1920

Ser Arg Gly Asn His Val Ser Pro Thr His Tyr Val Pro Glu Ser
    1925                1930                1935

Asp Ala Ala Ala Arg Val Thr Thr Ile Leu Ser Ser Leu Thr Val
    1940                1945                1950

Thr Ser Leu Leu Arg Arg Leu His Lys Trp Ile Asn Glu Asp Cys
    1955                1960                1965

Ser Thr Pro Cys Ala Glu Ser Trp Leu Trp Glu Val Trp Asp Trp
    1970                1975                1980

Val Cys Thr Val Leu Ser Asp Phe Lys Thr Trp Leu Lys Ala Lys
    1985                1990                1995

Leu Leu Pro Leu Met Pro Gly Ile Pro Phe Leu Ser Cys Gln Arg
    2000                2005                2010

Gly Tyr Lys Gly Glu Trp Arg Gly Asp Gly Val Met His Thr Thr
    2015                2020                2025

Cys Pro Cys Gly Ala Asp Leu Ala Gly His Ile Lys Asn Gly Ser
    2030                2035                2040

Met Arg Ile Thr Gly Pro Lys Thr Cys Ser Asn Thr Trp His Gly
    2045                2050                2055

Thr Phe Pro Ile Asn Ala Tyr Thr Thr Gly Pro Gly Val Pro Ile
    2060                2065                2070

Pro Ala Pro Asn Tyr Lys Phe Ala Leu Trp Arg Val Ser Ala Glu
    2075                2080                2085

Asp Tyr Val Glu Val Arg Arg Val Gly Asp Phe His Tyr Val Thr
    2090                2095                2100

Gly Val Thr Gln Asp Asn Ile Lys Cys Pro Cys Gln Val Pro Ala
    2105                2110                2115

Pro Glu Phe Phe Thr Glu Val Asp Gly Ile Arg Leu His Arg His
    2120                2125                2130

Ala Pro Lys Cys Lys Pro Leu Leu Arg Asp Glu Val Ser Phe Ser
    2135                2140                2145

Val Gly Leu Asn Ser Phe Val Val Gly Ser Gln Leu Pro Cys Glu
    2150                2155                2160

Pro Glu Pro Asp Val Ala Val Leu Thr Ser Met Leu Thr Asp Pro
    2165                2170                2175

Ser His Ile Thr Ala Glu Ser Ala Arg Arg Arg Leu Ala Arg Gly
    2180                2185                2190

Ser Arg Pro Ser Leu Ala Ser Ser Ser Ala Ser Gln Leu Ser Ala
```

-continued

|      | 2195 |      |      | 2200 |      |      | 2205 |      |      |
|------|------|------|------|------|------|------|------|------|------|
| Pro  | Ser  | Leu  | Lys  | Ala  | Thr  | Cys  | Thr  | Ala  | Pro  | His  | Asp  | Ser  | Pro  | Gly  |
|      | 2210 |      |      |      | 2215 |      |      | 2220 |      |

Pro Ser Leu Lys Ala Thr Cys Thr Ala Pro His Asp Ser Pro Gly
    2210            2215            2220

Thr Asp Leu Leu Glu Ala Asn Leu Leu Trp Gly Ser Thr Ala Thr
    2225            2230            2235

Arg Val Glu Thr Asp Glu Lys Val Ile Ile Leu Asp Ser Phe Glu
    2240            2245            2250

Ser Cys Val Ala Glu Pro Asn Asp Asp Arg Glu Val Ser Val Ala
    2255            2260            2265

Ala Glu Ile Leu Arg Pro Thr Lys Lys Phe Pro Pro Ala Leu Pro
    2270            2275            2280

Ile Trp Ala Arg Pro Asp Tyr Asn Pro Pro Leu Thr Glu Thr Trp
    2285            2290            2295

Lys Gln Gln Asp Tyr Lys Pro Pro Thr Val His Gly Cys Ala Leu
    2300            2305            2310

Pro Pro Gly Lys Gln Pro Val Pro Pro Arg Arg Lys Arg
    2315            2320            2325

Thr Val Gln Leu Thr Glu Ser Val Val Ser Thr Ala Leu Ala Glu
    2330            2335            2340

Leu Asp Ala Lys Thr Phe Gly Gln Ser Glu Pro Ser Ala Asp Arg
    2345            2350            2355

Asp Thr Asp Leu Thr Thr Pro Thr Glu Thr Thr Asp Ser Gly Pro
    2360            2365            2370

Ile Val Val Asp Asp Ala Phe Asp Asp Gly Ser Tyr Ser Ser Met
    2375            2380            2385

Pro Pro Leu Glu Gly Glu Pro Gly Asp Pro Asp Leu Thr Ser Asp
    2390            2395            2400

Ser Trp Ser Thr Val Ser Gly Ser Glu Asp Val Val Cys Cys Ser
    2405            2410            2415

Met Ser Tyr Ser Trp Thr Gly Ala Leu Ile Thr Pro Cys Ser Pro
    2420            2425            2430

Glu Glu Glu Lys Leu Pro Ile Asn Pro Leu Ser Asn Ser Leu Leu
    2435            2440            2445

Arg Tyr His Asn Lys Val Tyr Cys Thr Thr Ser Lys Ser Ala Ser
    2450            2455            2460

Gln Arg Ala Lys Lys Val Thr Phe Asp Arg Thr Gln Val Leu Asp
    2465            2470            2475

Ala His Tyr Asp Ser Val Leu Lys Asp Ile Lys Leu Ala Ala Ser
    2480            2485            2490

Lys Val Ser Ala Arg Leu Leu Thr Leu Glu Glu Ala Cys Gln Leu
    2495            2500            2505

Thr Pro Pro His Ser Ala Arg Ser Lys Tyr Gly Phe Gly Ala Lys
    2510            2515            2520

Glu Val Arg Ser Leu Ser Gly Arg Ala Val Asn His Ile Lys Ser
    2525            2530            2535

Val Trp Lys Asp Leu Leu Glu Asp Pro Gln Thr Pro Ile Pro Thr
    2540            2545            2550

Thr Ile Met Ala Lys Asn Glu Val Phe Cys Val Asp Pro Ala Lys
    2555            2560            2565

Gly Gly Lys Lys Pro Ala Arg Leu Ile Val Tyr Pro Asp Leu Gly
    2570            2575            2580

Val Arg Val Cys Glu Lys Met Ala Leu Tyr Asp Ile Thr Gln Lys
    2585            2590            2595

```
Leu Pro Gln Ala Val Met Gly Ala Ser Tyr Gly Phe Gln Tyr Ser
    2600            2605                2610
Pro Ala Gln Arg Val Glu Tyr Leu Leu Lys Ala Trp Ala Glu Lys
    2615            2620                2625
Lys Asp Pro Met Gly Phe Ser Tyr Asp Thr Arg Cys Phe Asp Ser
    2630            2635                2640
Thr Val Thr Glu Arg Asp Ile Arg Thr Glu Ser Ile Tyr Gln
    2645            2650                2655
Ala Cys Ser Leu Pro Glu Glu Ala Arg Thr Ala Ile His Ser Leu
    2660            2665                2670
Thr Glu Arg Leu Tyr Val Gly Gly Pro Met Phe Asn Ser Lys Gly
    2675            2680                2685
Gln Thr Cys Gly Tyr Arg Arg Cys Arg Ala Ser Gly Val Leu Thr
    2690            2695                2700
Thr Ser Met Gly Asn Thr Ile Thr Cys Tyr Val Lys Ala Leu Ala
    2705            2710                2715
Ala Cys Lys Ala Ala Gly Ile Val Ala Pro Thr Met Leu Val Cys
    2720            2725                2730
Gly Asp Asp Leu Val Val Ile Ser Glu Ser Gln Gly Thr Glu Glu
    2735            2740                2745
Asp Glu Arg Asn Leu Arg Ala Phe Thr Glu Ala Met Thr Arg Tyr
    2750            2755                2760
Ser Ala Pro Pro Gly Asp Pro Pro Arg Pro Glu Tyr Asp Leu Glu
    2765            2770                2775
Leu Ile Thr Ser Cys Ser Ser Asn Val Ser Val Ala Leu Gly Pro
    2780            2785                2790
Arg Gly Arg Arg Arg Tyr Tyr Leu Thr Arg Asp Pro Thr Thr Pro
    2795            2800                2805
Leu Ala Arg Ala Ala Trp Glu Thr Val Arg His Ser Pro Ile Asn
    2810            2815                2820
Ser Trp Leu Gly Asn Ile Ile Gln Tyr Ala Pro Thr Ile Trp Val
    2825            2830                2835
Arg Met Val Leu Met Thr His Phe Phe Ser Ile Leu Met Val Gln
    2840            2845                2850
Asp Thr Leu Asp Gln Asn Leu Asn Phe Glu Met Tyr Gly Ser Val
    2855            2860                2865
Tyr Ser Val Asn Pro Leu Asp Leu Pro Ala Ile Ile Glu Arg Leu
    2870            2875                2880
His Gly Leu Asp Ala Phe Ser Met His Thr Tyr Ser His His Glu
    2885            2890                2895
Leu Thr Arg Val Ala Ser Ala Leu Arg Lys Leu Gly Ala Pro Pro
    2900            2905                2910
Leu Arg Val Trp Lys Ser Arg Ala Arg Ala Val Arg Ala Ser Leu
    2915            2920                2925
Ile Ser Arg Gly Gly Lys Ala Ala Val Cys Gly Arg Tyr Leu Phe
    2930            2935                2940
Asn Trp Ala Val Lys Thr Lys Leu Lys Leu Thr Pro Leu Pro Glu
    2945            2950                2955
Ala Arg Leu Leu Asp Leu Ser Ser Trp Phe Thr Val Gly Ala Gly
    2960            2965                2970
Gly Gly Asp Ile Phe His Ser Val Ser Arg Ala Arg Pro Arg Ser
    2975            2980                2985
```

-continued

```
Leu Leu  Phe Gly Leu Leu Leu  Leu Phe Val Gly Val  Gly Leu Phe
    2990             2995             3000

Leu Leu  Pro Ala Arg
    3005
```